(12) United States Patent
Guyenot et al.

(10) Patent No.: US 7,896,915 B2
(45) Date of Patent: Mar. 1, 2011

(54) MEDICAL DEVICE FOR TREATING A HEART VALVE INSUFFICIENCY

(75) Inventors: Volker Guyenot, Jena (DE); Thomas Peschel, Jena (DE); Christoph Damm, Jena (DE); Hans-Reiner Figulla, Jena (DE); Markus Ferrari, Jena (DE); Johannes Jung, Pforzheim (DE)

(73) Assignee: JenaValve Technology, Inc., Wilmington, DE (US)

( * ) Notice: Subject to any disclaimer, the term of this patent is extended or adjusted under 35 U.S.C. 154(b) by 291 days.

(21) Appl. No.: 11/785,072

(22) Filed: Apr. 13, 2007

(65) Prior Publication Data

US 2008/0255660 A1    Oct. 16, 2008

(51) Int. Cl.
*A61F 2/24* (2006.01)
(52) U.S. Cl. .................... 623/2.14; 623/1.24; 623/2.17; 623/2.18
(58) Field of Classification Search ................ 623/2.14, 623/2.17, 2.18, 1.15, 1.16, 1.24
See application file for complete search history.

(56) References Cited

U.S. PATENT DOCUMENTS

| | | | |
|---|---|---|---|
| 5,002,566 A | 3/1991 | Carpentier et al. |
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |

(Continued)

FOREIGN PATENT DOCUMENTS

AU    2006308187 A1    5/2007

(Continued)

OTHER PUBLICATIONS

File history for German Patent DE 195 46 692 filed Dec. 14, 1995 and patented Jul. 11, 2002.

(Continued)

*Primary Examiner*—Corrine M McDermott
*Assistant Examiner*—Matthew Schall
(74) *Attorney, Agent, or Firm*—Finnegan, Henderson, Farabow, Garrett & Dunner, L.L.P.

(57) ABSTRACT

A medical device for treating a heart valve insufficiency, with an endoprosthesis which can be introduced into a patient's body and expanded to secure a heart valve prosthesis in the patient's aorta. In an embodiment, the endoprosthesis has at plurality of positioning arches configured to be positioned with respect to a patient's aorta and a plurality of retaining arches to support a heart valve prosthesis. The endoprosthesis includes a first collapsed mode during the process of introducing it into the patient's body and a second expanded mode when it is implanted.

53 Claims, 48 Drawing Sheets

U.S. PATENT DOCUMENTS

| | | |
|---|---|---|
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 A | 9/1999 | Lam et al. |
| 6,001,126 A | 12/1999 | Nguyen-Thien-Nhon |
| 5,061,277 A | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2* | 4/2007 | Figulla et al. ................ 623/2.1 |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 2001/0011187 A1 | 8/2001 | Pavcnik et al. |
| 2001/0039450 A1 | 11/2001 | Pavcnik et al. |
| 2001/0044652 A1* | 11/2001 | Moore ...................... 623/1.16 |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1* | 6/2003 | Spenser et al. ............. 623/1.11 |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075726 A1* | 4/2005 | Svanidze et al. ........... 623/2.14 |
| 2005/0075776 A1 | 4/2005 | Cho |
| 2005/0096726 A1 | 5/2005 | Sequin et al. |

| | | | | | | |
|---|---|---|---|---|---|---|
| 2005/0096736 A1 | 5/2005 | Osse et al. | | 2008/0004688 A1 | 1/2008 | Spenser et al. |
| 2005/0098547 A1 | 5/2005 | Cali et al. | | 2008/0021546 A1 | 1/2008 | Patz et al. |
| 2005/0113910 A1 | 5/2005 | Paniagua et al. | | 2008/0033534 A1 | 2/2008 | Cook et al. |
| 2005/0119728 A1 | 6/2005 | Sarac | | 2008/0065011 A1 | 3/2008 | Marchand et al. |
| 2005/0119736 A1 | 6/2005 | Zilla et al. | | 2008/0071361 A1 | 3/2008 | Tuval et al. |
| 2005/0137687 A1 | 6/2005 | Salahieh et al. | | 2008/0071362 A1 | 3/2008 | Tuval et al. |
| 2005/0137688 A1 | 6/2005 | Salahieh et al. | | 2008/0071363 A1 | 3/2008 | Tuval et al. |
| 2005/0137690 A1 | 6/2005 | Salahieh et al. | | 2008/0071366 A1 | 3/2008 | Tuval et al. |
| 2005/0137697 A1 | 6/2005 | Salahieh et al. | | 2008/0071368 A1 | 3/2008 | Tuval et al. |
| 2005/0137698 A1 | 6/2005 | Salahieh et al. | | 2008/0071369 A1 | 3/2008 | Tuval et al. |
| 2005/0137702 A1 | 6/2005 | Haug et al. | | 2008/0077236 A1 | 3/2008 | Letac et al. |
| 2005/0143804 A1 | 6/2005 | Haverkost | | 2008/0086205 A1 | 4/2008 | Gordy et al. |
| 2005/0143807 A1 | 6/2005 | Pavcnik et al. | | 2008/0097586 A1 | 4/2008 | Pavcnik et al. |
| 2005/0149166 A1 | 7/2005 | Schaeffer et al. | | 2008/0102439 A1 | 5/2008 | Tian et al. |
| 2005/0150775 A1 | 7/2005 | Zhang et al. | | 2008/0133003 A1 | 6/2008 | Seguin et al. |
| 2005/0171597 A1 | 8/2005 | Boatman et al. | | 2008/0140189 A1 | 6/2008 | Nguyen et al. |
| 2005/0171598 A1 | 8/2005 | Schaeffer | | 2008/0154355 A1 | 6/2008 | Benichou et al. |
| 2005/0192665 A1 | 9/2005 | Spenser et al. | | 2008/0200977 A1 | 8/2008 | Paul et al. |
| 2005/0197695 A1 | 9/2005 | Stacchino et al. | | 2008/0215143 A1 | 9/2008 | Seguin |
| 2005/0222668 A1 | 10/2005 | Schaeffer et al. | | 2008/0255661 A1 | 10/2008 | Straubinger et al. |
| 2005/0228496 A1 | 10/2005 | Mensah et al. | | 2008/0262602 A1 | 10/2008 | Wilk et al. |
| 2005/0234546 A1 | 10/2005 | Nugent et al. | | 2008/0269878 A1 | 10/2008 | Iobbi |
| 2005/0267560 A1 | 12/2005 | Bates | | 2008/0275549 A1 | 11/2008 | Rowe |
| 2006/0009842 A1 | 1/2006 | Huynh et al. | | | | |
| 2006/0025857 A1 | 2/2006 | Bergheim et al. | | FOREIGN PATENT DOCUMENTS | | |
| 2006/0047343 A1 | 3/2006 | Oviatt et al. | | | | |
| 2006/0058864 A1 | 3/2006 | Schaeffer et al. | | AU | 2006310681 A1 | 5/2007 |
| 2006/0074484 A1 | 4/2006 | Huber | | CA | 2436258 A1 | 1/2005 |
| 2006/0111770 A1 | 5/2006 | Pavcnik et al. | | CA | 2595233 | 7/2006 |
| 2006/0142846 A1 | 6/2006 | Pavcnik et al. | | CA | 2627555 | 5/2007 |
| 2006/0149360 A1 | 7/2006 | Schwammenthal et al. | | DE | 195 46 692 A1 | 6/1997 |
| 2006/0155366 A1 | 7/2006 | LaDuca et al. | | DE | 19546692 A1 | 6/1997 |
| 2006/0167543 A1 | 7/2006 | Bailey et al. | | DE | 20003874 U1 | 6/2000 |
| 2006/0193885 A1 | 8/2006 | Neethling et al. | | DE | 19857887 A1 | 7/2000 |
| 2006/0210597 A1 | 9/2006 | Hiles | | DE | 10010073 A1 | 9/2001 |
| 2006/0229718 A1 | 10/2006 | Marquez | | DE | 10010074 A1 | 10/2001 |
| 2006/0229719 A1 | 10/2006 | Marquez et al. | | DE | 101 21 210 A1 | 11/2002 |
| 2006/0246584 A1 | 11/2006 | Covelli | | DE | 19546692 C2 | 11/2002 |
| 2006/0259134 A1 | 11/2006 | Schwammenthal et al. | | DE | 10010073 B4 | 12/2002 |
| 2006/0259136 A1 | 11/2006 | Nguyen et al. | | DE | 10301026 A1 | 2/2004 |
| 2006/0265056 A1 | 11/2006 | Nguyen et al. | | DE | 10302447 A1 | 7/2004 |
| 2006/0287717 A1 | 12/2006 | Rowe et al. | | DE | 10335948 B3 | 2/2005 |
| 2006/0287719 A1 | 12/2006 | Rowe et al. | | DE | 10010074 B4 | 4/2005 |
| 2006/0290027 A1 | 12/2006 | O'Connor et al. | | DE | 19857887 B4 | 5/2005 |
| 2006/0293745 A1 | 12/2006 | Carpentier et al. | | DE | 10 2005 051 849 A1 | 5/2007 |
| 2007/0005129 A1 | 1/2007 | Damm et al. | | DE | 10 2005 052 628 A1 | 5/2007 |
| 2007/0005131 A1 | 1/2007 | Taylor | | DE | 202007005491 U1 | 7/2007 |
| 2007/0005132 A1 | 1/2007 | Simionescu et al. | | EP | 0084395 A1 | 7/1983 |
| 2007/0020248 A1 | 1/2007 | Everaerts et al. | | EP | 0458877 | 8/1990 |
| 2007/0021826 A1 | 1/2007 | Case et al. | | EP | 0402036 B1 | 12/1990 |
| 2007/0027535 A1 | 2/2007 | Purdy, Jr. et al. | | EP | 0402176 B1 | 12/1990 |
| 2007/0038291 A1 | 2/2007 | Case et al. | | EP | 0458877 B1 | 4/1991 |
| 2007/0038295 A1 | 2/2007 | Case et al. | | EP | 0515324 A1 | 11/1992 |
| 2007/0043435 A1 | 2/2007 | Seguin et al. | | EP | 0547135 B1 | 6/1993 |
| 2007/0050014 A1 | 3/2007 | Johnson | | EP | 0871414 | 9/1995 |
| 2007/0088431 A1 | 4/2007 | Bourang et al. | | EP | 0 592 410 B1 | 10/1995 |
| 2007/0093887 A1 | 4/2007 | Case et al. | | EP | 0756498 | 10/1995 |
| 2007/0100435 A1 | 5/2007 | Case et al. | | EP | 0 592 410 B1 | 11/1995 |
| 2007/0100440 A1 | 5/2007 | Figulla et al. | | EP | 0786970 | 5/1996 |
| 2007/0112422 A1 | 5/2007 | Dehdashtian | | EP | 0729364 B1 | 9/1996 |
| 2007/0123700 A1 | 5/2007 | Ueda et al. | | EP | 0756498 B1 | 5/1997 |
| 2007/0123979 A1 | 5/2007 | Perier et al. | | EP | 0778775 B1 | 6/1997 |
| 2007/0142906 A1 | 6/2007 | Figulla et al. | | EP | 0786970 | 8/1997 |
| 2007/0162103 A1 | 7/2007 | Case et al. | | EP | 0888142 | 9/1997 |
| 2007/0173932 A1 | 7/2007 | Cali et al. | | EP | 0971649 | 10/1998 |
| 2007/0179592 A1 | 8/2007 | Schaeffer | | EP | 0928615 A1 | 7/1999 |
| 2007/0185565 A1 | 8/2007 | Schwammenthal et al. | | EP | 1051204 | 7/1999 |
| 2007/0203576 A1 | 8/2007 | Lee et al. | | EP | 1089676 | 12/1999 |
| 2007/0213813 A1 | 9/2007 | Von Segesser et al. | | EP | 0986348 B1 | 3/2000 |
| 2007/0239271 A1 | 10/2007 | Nguyen | | EP | 1117446 | 4/2000 |
| 2007/0244551 A1 | 10/2007 | Stobie | | EP | 1 164 976 | 8/2000 |
| 2007/0260327 A1 | 11/2007 | Case et al. | | EP | 1158937 | 9/2000 |
| 2007/0288087 A1 | 12/2007 | Fearnot et al. | | EP | 1 251 805 B1 | 10/2000 |

| | | |
|---|---|---|
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1281375 A2 | 2/2003 |
| EP | 1408882 | 2/2003 |
| EP | 1 435 878 | 4/2003 |
| EP | 1 435 879 | 4/2003 |
| EP | 1 017 868 B1 | 9/2003 |
| EP | 1354569 A1 | 10/2003 |
| EP | 1494616 | 10/2003 |
| EP | 1 441 672 | 1/2004 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1469797 B1 | 11/2005 |
| EP | 1835948 | 6/2006 |
| EP | 1863545 | 9/2006 |
| EP | 1893132 | 11/2006 |
| EP | 1901681 | 11/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| JP | 2008539305 | 11/2008 |
| WO | WO-90/09102 | 8/1990 |
| WO | WO 95/11055 A1 | 4/1995 |
| WO | WO 95/24873 | 9/1995 |
| WO | WO-95/28183 | 10/1995 |
| WO | WO-96/13227 | 5/1996 |
| WO | WO-97/32615 | 9/1997 |
| WO | WO 98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A1 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2006/076890 | 7/2008 |
| WO | WO 2008/079962 A1 | 7/2008 |
| WO | WO 2008/101083 A2 | 8/2008 |
| WO | WO 2008/125153 A1 | 10/2008 |

WO  WO 2008/138584 A1  11/2008

OTHER PUBLICATIONS

Aortenklappenbioprothese erfolgreich in der Entwicklung, (1 page) May 16, 2003.

Translation of Aortenklappenbioprothese erfolgreich in der Entwicklung (2 pages).

Screen shots from http://www.fraunhofer.de/presse/filme/2006/index.jsp (2 pages), 2006.

Liang, Ma, et al., "Double-crowned valved stents for off-pump mitral valve replacement," European Journal of Cardio-Thoracic Surgery, 194-198 (5 pages), Jun. 13, 2005.

Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.

Translation of DE 19546692 A1 (4 pages).

Translation of EP 1469797 B1 (16 pages).

U.S. Appl. No. 12/084,421, filed May 1, 2008.

* cited by examiner

MEDICAL DEVICE FOR TREATING A HEART VALVE INSUFFICIENCY

BACKGROUND

This invention relates to a medical device for treating a heart valve insufficiency, with an endoprosthesis which can be introduced into a patient's body with minimal invasion and automatically expanded in order to position and secure a heart valve prosthesis in the patient's aorta, which endoprosthesis has at least three positioning arches for automatically positioning the medical device in the patient's aorta and a retaining segment with retaining arches for accommodating a heart valve prosthesis, and the endoprosthesis assumes a first pre-definable mode during the process of introducing it into the patient's body and a second pre-definable mode in the state when the medical device is implanted, and when the medical device is in a collapsed state when the endoprosthesis is in the first mode and in an expanded state when the endoprosthesis is in the second mode.

The operating principle of such a device is known from medical technology. Biological or mechanical valve models are currently available as a means of replacing human heart valves, which are securely stitched in the heart valve base through an opening in the thorax during surgery once the diseased heart valve has been removed. In order to undertake this intervention, the patient's circulation must be supported by a heart and lung machine and the heart is arrested whilst the heart valve prosthesis is being implanted. This is a risky surgical intervention which places the patient at risk accordingly and which involves a long post-operative phase of treatment. In multi-morbid patients in particular, the risk of carrying out such intervention is no longer justifiable.

In more recent times, treatment methods which are minimally invasive have been developed, which are distinctive due to the fact that the intervention can be carried out with a local anaesthetic. This option is based on the use of a self-expanding stent with a collapsible heart valve prosthesis, which is implanted in the human body by means of an appropriate catheter system. A self-expanding heart valve prosthesis of this type can be fed by means of a catheter system through a main artery or vein to the implantation site at the heart. Once the implantation site is reached, the stent, which is made up of several self-expanding stent segments which can be angled relative to one another, is successively unfolded. Once unfolded, the heart valve prosthesis can be anchored in the respective blood vessel at least in the vicinity of the heart with the assistance of anchoring hooks for example. The actual heart valve prosthesis is then disposed directly in the proximal region of the stent or endoprosthesis.

Patent publication DE 100 10 074 A1, for example, discloses a device for securing and anchoring heart valve prostheses, which essentially comprises shaped wire elements connected to one another. In this instance, different arches are used as a means of reliably securing and anchoring the heart valve prosthesis. To this end, the device described in this specification has three identical pairs of arches respectively disposed at a distance of 120° apart. These arches are connected to one another by fixed body joints, and the fixed body joints assume the function of pivot bearings. Arches bent in the opposite direction are also provided, which form lever arms which are of identical length as far as possible, to enable a reliable seating of the arches, even in the event of peristaltic movements of the heart and blood vessel, and afford a reliable seal for an implanted and secured heart valve prosthesis.

With the known solution, however, there is still a risk of heart valves being incorrectly implanted. In particular, this is attributable to the fact that the heart valve prosthesis must be exactly positioned and longitudinally oriented. In particular, it requires enormous skill on the part of the surgeon performing the treatment—if it is possible at all—to position a stent which has a heart valve prosthesis at its proximal end and to do so accurately enough in the vicinity of the patient's diseased heart valve to ensure both correct lateral positioning accuracy and a correct longitudinal position of the heart valve prosthesis as far as possible.

Amongst other things, incorrect implantation of a heart valve prosthesis that is not optimally positioned can lead to inadequate sealing or valve insufficiency, which places considerable stress on the ventricle. If a heart valve prosthesis is implanted too far above the actual heart valve plane, for example, this can cause the outlets of the coronary vessels (coronaries) to close, thus leading to fatal coronary ischaemia due to heart infarction. This being the case, it is absolutely vital that both the lateral positioning accuracy and longitudinal positioning accuracy of a heart valve prosthesis meet requirements.

In the case of conventional implantation techniques whereby self-expandable heart valve prostheses are fed to the implantation site at the heart through a main artery of the patient requiring minimal invasion, for example, the prosthesis is usually introduced by means of a guide wire and with the aid of catheters, in which case it is standard practice to use a balloon catheter for this intervention. Although it is possible to monitor and control the introduction process during such an intervention, for example with the aid of an X-ray system (heart catheter laboratory=HCL) or with the aid of ultrasound (trans-oesophageal echocardiagram=TEE), the heart valve prosthesis is still of relatively large dimensions in spite of being collapsed whilst it is being introduced and it is often not possible to obtain the required positioning accuracy due to restricted ability to manoeuvre, and in particular to ensure correct longitudinal positioning of the heart valve prosthesis to be implanted with the fixing elements attached to it accordingly. Especially if there is a risk that the coronary vessels might close, implanting the heart valve prosthesis in a position angularly offset from the optimum implantation site represents a particular risk for the patient.

When designing a heart valve prosthesis, allowance must specifically be made for the considerable forces which act on the prosthesis, including during the filling phase of the heart cycle (diastole), and reliable anchoring is necessary in order to prevent the implanted heart valve prosthesis from becoming detached.

Accordingly, it must be possible to manoeuvre the heart valve prosthesis in the relevant access vessel as efficiently as possible during the implantation process in order to ensure optimum positioning accuracy on the one hand, and on the other hand, the implanted heart valve prosthesis must be firmly anchored at the implantation site in order effectively to prevent the prosthesis from shifting subsequently.

The underlying problem addressed by this invention is the fact that known devices used for the transvascular implantation of heart valve prostheses are often not suitable for implanting a heart valve prosthesis easily to the required degree of positioning accuracy. Furthermore, until now, it has only been possible to correct an incorrectly positioned heart valve prosthesis that has already been partially implanted with great difficulty—if at all.

SUMMARY

Against this background, the objective of the invention is to improve a medical device for treating heart valve insufficiency of the type outlined above so that maneuvering of the device is optimised during the implantation process on the one hand, and whilst achieving optimum positioning accuracy and anchoring of the implanted heart valve prosthesis on the other hand, thereby permitting a routine treatment of heart valve insufficiency without subjecting the patient to excessive stress.

This objective is achieved by means of a medical device of the type outlined above due to the fact that the endoprosthesis of the medical device is of an integral structure cut from a metal tube, and every end portion of the positioning arch at the distal end of the endoprosthesis is joined to the terminal portion of the associated retaining arch.

Accordingly, a medical device is proposed which essentially comprises a self-expandable endoprosthesis (hereafter referred to simply as stent), and this stent has a valve-supporting retaining segment for accommodating a heart valve prosthesis. The stent design is distinctive due to the fact that at least three positioning arches are provided, which project radially outwards and are open when the endoprosthesis assumes the second pre-definable mode, in which the original (old) heart valves of the heart valve to be replaced engage, thereby resulting in an automatic fixing and positioning of the medical device as regards the axial rotation on the one hand and the horizontal position on the other hand.

Since the endoprosthesis (stent) of the medical device has an integral structure cut from a metal tube incorporating the positioning arches on the one hand and the retaining segment with the retaining arches on the other hand, the endoprosthesis and hence also the medical device can be made particularly inexpensively and in large numbers. Specifically, it would be conceivable to cut the stent structure from a metal tube by means of a laser, after which the structure is subjected to an appropriate shaping and heat treatment process so that the endoprosthesis and hence also the medical device can be transferred from the collapsed sate during implantation to the expanded state at the implantation site. This shaping and heat treatment process is advantageously operated in steps in order to prevent damage to the stent structure.

Since the endoprosthesis of the medical device is of an integral structure cut from a metal tube as proposed by the invention and a retaining arch is associated with every positioning arch and every end portion of the positioning arch at the distal end of the endoprosthesis is joined to the terminal portion of the associated retaining arch, there is no need to provide fixed body joints or similar connecting devices. On the other hand, the endoprosthesis of the medical device proposed by the invention is a stent which, on the one hand, offers a positioning function due to the positioning arches with a minimal longitudinal extension and, on the other hand, offers a function of retaining a heart valve prosthesis due to the retaining arches.

As will be seen, when transferring the endoprosthesis from the first pre-definable mode to the second pre-definable mode by widening the cross-section of the entire stent, the retaining arches on the one hand and the positioning arches on the other hand are opened out in the radial direction. The second mode of the endoprosthesis is advantageously selected so that as the retaining and positioning arches open up, they hit against the vessel wall of the aorta and form a positive connection with it, thereby anchoring the medical device firmly at the implantation site.

Due to the fact that the structure of the endoprosthesis imparts a particularly short shape to the medical device, the medical device is particularly easy to manoeuvre in the collapsed state, which is of particular advantage if the implantation route to the heart valve to be replaced leads through the arch of the aorta. The minimum length of the medical device is made possible in particular by the special structure of the endoprosthesis due to the fact that every end portion of the positioning arch at the distal end is joined to the end portion of the associated retaining arch, and both the positioning arch and the retaining arch extend to the proximal retaining region of the medical device or endoprosthesis. The retaining segment for accommodating the heart valve prosthesis therefore lies at the proximal retaining region of the endoprosthesis.

Advantageous embodiments of the medical device are specified in the dependent claims, especially as regards the endoprosthesis (stent).

In one particular embodiment of the endoprosthesis used with the medical device proposed by the invention, every positioning arch and its associated retaining arch is respectively of an essentially U-shaped or V-shaped structure, which is closed towards the proximal end of the endoprosthesis. By particular preference, every positioning arch is cut from the material blank of the metal tube which is accommodated by the essentially U-shaped or V-shaped structure of the associated retaining arch. In this preferred embodiment of the stent structure, therefore, the respective retaining arches of the retaining segment form the proximal retaining region of the endoprosthesis and the respective positioning arches are of a design symmetrical with the retaining arches but lie slightly in front of the distal retaining region of the medical device. The respective distal ends of the positioning arches are joined to the respective distal ends of the co-operating retaining arches in the distal retaining region of the medical device or endoprosthesis. When the medical device is in the expanded state, not only the proximal retaining region with the heart valve prosthesis fitted to it and the positioning arches disposed between the proximal and the distal retaining regions of the medical device open out, but also the joining points between the respective positioning arches and retaining arches at the distal end of the medical device, so that a radially acting force is also applied to the vessel wall via the distal retaining region of the medical device, which further assists anchoring of the medical device at the implantation site.

Since the medical device is in a (an expanded) state in which the distal and proximal retaining region as well as the positioning arches are radially opened out when the endoprosthesis assumes the second mode, the expanded medical device has as shorter length than it does in its collapsed state. To enable the length of the medical device in its expanded state to be set beforehand, it would be conceivable to connect the respective distal end portions of the positioning arches to the distal end portions of the associated retaining arches using a connecting web extending essentially in the longitudinal direction of the endoprosthesis rather than directly. The length of the medical device in the expanded state can therefore be adapted by selecting the length of this connecting web accordingly. However, it is preferable, especially with a view to ensuring good manoeuvrability of the medical device during the implantation process, i.e. when the endoprosthesis is in its first (collapsed) mode, if the connecting web between the respective end portions of the positioning arches and retaining arches is selected so that it is as short as possible.

In one particularly preferred embodiment of the medical device, the endoprosthesis has other fixing means at its distal end, which can be engaged with an introduction catheter system. In a preferred embodiment of the fixing means, it would be conceivable for the latter to have a respective anchoring eye disposed between two adjacent positioning arches, in which case the respective arms of the adjacent positioning arches on the one hand and the respective arms of the retaining arches associated with the adjacent positioning arches on the other hand are connected to the anchoring eye. It would likewise be conceivable for the respective arms of the adjacent positioning arches to be directly and the respective arms of the retaining arches associated with the adjacent positioning arches to be indirectly connected via a connecting web extending essentially in the longitudinal direction of the endoprosthesis. Generally speaking, the purpose of the fixing means provided on the distal end of the endoprosthesis is to accommodate appropriate mechanisms on the introduction catheter system and these mechanisms are of a design complementing that of the fixing means of the endoprosthesis. The engagement between the catheter system on the one hand and the fixing means on the distal end of the endoprosthesis on the other hand can be released by means of an external manipulation in order to release the medical device at the implantation site, thereby ensuring that the medical device expands and is thus reliably anchored. Naturally, however, other fixing means could also be used.

As mentioned above, because of the special structure of the endoprosthesis, it is possible to use a self-expandable medical device which is distinctive due to its short overall length in the collapsed state, thereby ensuring improved manoeuvrability during the implantation process, whilst simultaneously affording a self-positioning function in the pockets of the old heart valve with the aid of the positioning arches so that the endoprosthesis is reliably anchored by the proximal and distal retaining regions of the endoprosthesis pressing radially against the vessel wall in the expanded state.

As an alternative to the preferred embodiment of the medical device outlined above, in which the respective arms of the adjacent positioning arches are joined directly and the respective arms of the retaining arches associated with the adjacent positioning arches are joined indirectly to the fixing eye by means of a connecting web extending essentially in the longitudinal direction of the endoprosthesis, it would however also be conceivable for the respective arms of the adjacent positioning arches to be joined to the fixing eye indirectly via a connecting web extending essentially in the longitudinal direction of the endoprosthesis, in which case the respective arms of the retaining arches associated with the adjacent positioning arches are joined to the fixing eye indirectly via a connecting web extending essentially in the longitudinal direction of the endoprosthesis, and the connecting web of the retaining arches merges into the connecting web of the positioning arches at the end portion of the positioning arches. Providing the respective connecting webs for connecting the arms of the positioning arches to the fixing eye and for connecting the arms of the retaining arches to the end portion of the positioning arches offers a particularly simple but effective way of adapting the length of the endoprosthesis to respective requirements and does so because the respective lengths of the connecting webs can be selected accordingly.

In a preferred embodiment of the solution proposed by the invention, in order to ensure that the distal retaining region of the endoprosthesis can be retained at the implantation site in its expanded state particularly reliably, the endoprosthesis is provided with fixing eyes or similar at its distal retaining region, and these fixing eyes, which are preferably disposed between two adjacent positioning arches, are respectively provided with at least one barb, the tip of which points in the direction of the proximal end of the endoprosthesis. In this preferred embodiment, therefore, the endoprosthesis is secured at the implantation site due to the radial force exerted on the vessel wall by the endoprosthesis and in particular by the distal retaining region of the endoprosthesis, but also due to the barb hooking into the vessel wall. As regards the barb, it would naturally also be possible to use other appropriate design options.

As an alternative to or in addition to the barbs, which are preferably provided on the fixing eyes, another conceivable way of securing the endoprosthesis reliably at the implantation site is for the respective arms of the retaining arches of the endoprosthesis to be respectively provided with an anchoring support in the shape of a bow, which projects out from the relevant arm of the retaining arch when the endoprosthesis is in the expanded state, the tip of which points in the direction of the distal end of the endoprosthesis. This embodiment therefore provides additional fixing means for the endoprosthesis and accordingly additionally secures the medical device to prevent it from becoming dislocated.

In a preferred embodiment of the anchoring support, it would be conceivable for the anchoring support to be of an essentially U-shaped or V-shaped structure which is closed at the distal end of the endoprosthesis or the distal end of the medical device, in which case the distal region of the anchoring support constitutes the tip of the anchoring support and the respective arms of the anchoring support are joined to the respective arms of two adjacent retaining arches at the proximal end of the anchoring support.

Alternatively, in another preferred embodiment, the respective arms of the retaining arches have continuous slots or elongate holes extending in the longitudinal direction of the retaining arches, the purpose of which is to enable and assist the expansion of the endoprosthesis from the collapsed state into the expanded state because these slots or elongate holes are preferably designed to permit a particularly easy cross-sectional expansion of the stent (endoprosthesis) whilst simultaneously reducing the length. Such slots or elongate holes have the additional advantage of saving on material.

In the case of the latter embodiment in which the respective retaining arches incorporate slots extending in the longitudinal direction of the retaining arches designed to influence the shape of the endoprosthesis in the second mode, it would be conceivable for the respective retaining arches to be additionally provided with reinforcing portions which interrupt the slots extending in the longitudinal direction of the retaining arches and which prevent components of the retaining arches from projecting outwards when the endoprosthesis is in the expanded state, which is of particular advantage in preventing explanation of the medical device.

In a preferred embodiment, the endoprosthesis has an external diameter of approximately 5.0 mm and a length of between 33.0 mm and 40.0 mm, preferably between 34.0 and 39.0 mm, and even more preferably between 34.37 mm and 38.37 mm, in its first mode, which means that the medical device can be introduced by means of a 21 F introduction system, for example, and heart valve prostheses with a diameter of 21 mm to 28 mm may be used. The length specifications given above are currently preferred values, on the basis of which the medical device is suitable for the majority of patients to be treated.

In order to obtain a particularly reliable anchoring of the implanted medical device in its expanded state, the endoprosthesis is subjected to a shaping and heat treatment process during its manufacture so that when the endoprosthesis is in the finished state, it has a slightly concave shape tapering in the direction of the proximal retaining region of the endoprosthesis in its second mode.

In other words, this means that the proximal retaining region of the endoprosthesis, i.e. the region to which the heart valve prosthesis is attached, has a slightly narrower diameter than the distal retaining region. It has effectively been found that if the distal retaining region of the endoprosthesis in the second mode has an approximately 10% to 25% bigger diameter than the proximal retaining region of the endoprosthesis, radial forces are generated at the distal retaining region of the endoprosthesis in particular which enable the medical device to be securely retained in the vessel without causing damage to the vessel wall, and due allowance is also made for the peristaltic movements of the heart and vessel wall. The slightly lower radial force expended by the proximal retaining region of the endoprosthesis not only serves as a means of anchoring the medical device in the aorta but in particular also opens out the heart valve prosthesis fitted on the proximal retaining region of the endoprosthesis and imparts to it a reliable seal with respect to the vessel wall. Naturally, however, it would also be conceivable for the concave shape to be more or less pronounced when the endoprosthesis assumes the second mode.

In particular, however, it is preferable if the retaining region of the endoprosthesis has a diameter of between 22 mm and 33 mm, and preferably between 25 mm and 31 mm, in the second mode. This being the case, it would be conceivable for the endoprosthesis to be made in two or more differently dimensioned sizes, in which case an optimum size of endoprosthesis could be selected depending on the patient, and the exact dimensions of the endoprosthesis are adapted to the patient to be treated—starting from a pre-defined stent size—by an appropriate finishing treatment of the endoprosthesis (stent), in particular by tempering.

In one, particularly preferred embodiment of the medical device, not only does it have the endoprosthesis (stent) but also a heart valve prosthesis, preferably a bio-heart valve prosthesis, which is attached to the retaining segment of the endoprosthesis by means of a thread or similar, in which case orifices are provided in the retaining arches of the endoprosthesis through which the thread or similar is inserted. Accordingly, it would also be conceivable for the heart valve prosthesis to be connected to the retaining segment of the endoprosthesis immediately prior to the medical intervention. As a result, the medical device can be made in a modular design, which is of particular advantage in terms of transporting and storing the medical device.

As regards the preferred material used for the endoprosthesis of the medical device, a shape memory material is used, which is designed so that the endoprosthesis is transformed from a temporary shape to a permanent shape by means of an external stimulus, in which case the endoprosthesis assumes the temporary shape in the first mode (when the medical device is in the collapsed state) and the endoprosthesis assumes the permanent shape in the second mode (when the medical device is in the expanded state). Especially if a shape memory material such as Nitinol is used, i.e. an equal atomic alloy of nickel and titanium, the implantation process will be particularly gentle during the operation of implanting the medical device.

During production of an endoprosthesis made from a shape memory material, after the stent structure has been cut from the metal tube, it is deformed and fixed in the desired permanent shape, a process which is known as programming. This operation may be performed on the one hand by heating, deforming and then cooling the stent structure. Alternatively, the stent structure may also be deformed at low temperature by an operation known as cold stretching. As a result, the permanent shape is memorised whilst the temporary shape actually prevails. If the stent structure is then subjected to an external stimulus, the shape memory effect is triggered and the memorised permanent shape is restored.

In a particularly preferred embodiment, the external stimulus is a settable switching temperature. It is therefore conceivable for the endoprosthesis material to be heated to a temperature higher than the switching temperature in order to trigger the shape memory effect and thus restore the memorised permanent shape of the endoprosthesis. By selecting the chemical composition of the shape memory material accordingly, a specific switching temperature can be fixed beforehand.

This being the case, the switching temperature is set so that it falls within the range of room temperature and the body temperature of the patient. This is of particular advantage in applications where the medical device is to be implanted in a patient's body. Accordingly, when implanting the medical device, it is merely necessary to ensure that the instrument is not heated and thus triggers the shape memory effect of the endoprosthesis material until it is in the implanted state on the patient's body (36° C.).

BRIEF DESCRIPTION OF THE DRAWINGS

Preferred embodiments of an endoprosthesis of a medical device proposed by the invention will be described in more detail below with reference to the appended drawings.

Of these.

DETAILED DESCRIPTION

Figure 1A:
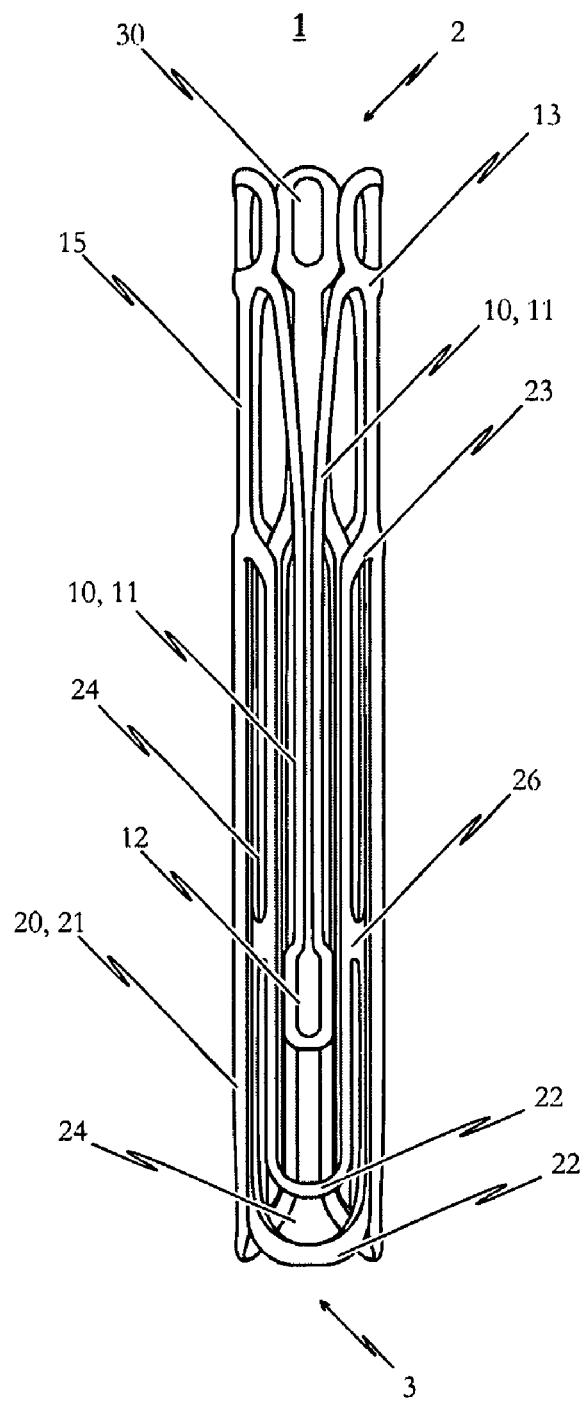
FIG. 1a illustrates a first, preferred embodiment of a self-expandable endoprosthesis for the medical device proposed by the invention in its first predefined mode in which the medical device is in its collapsed state.
Figure 1B:
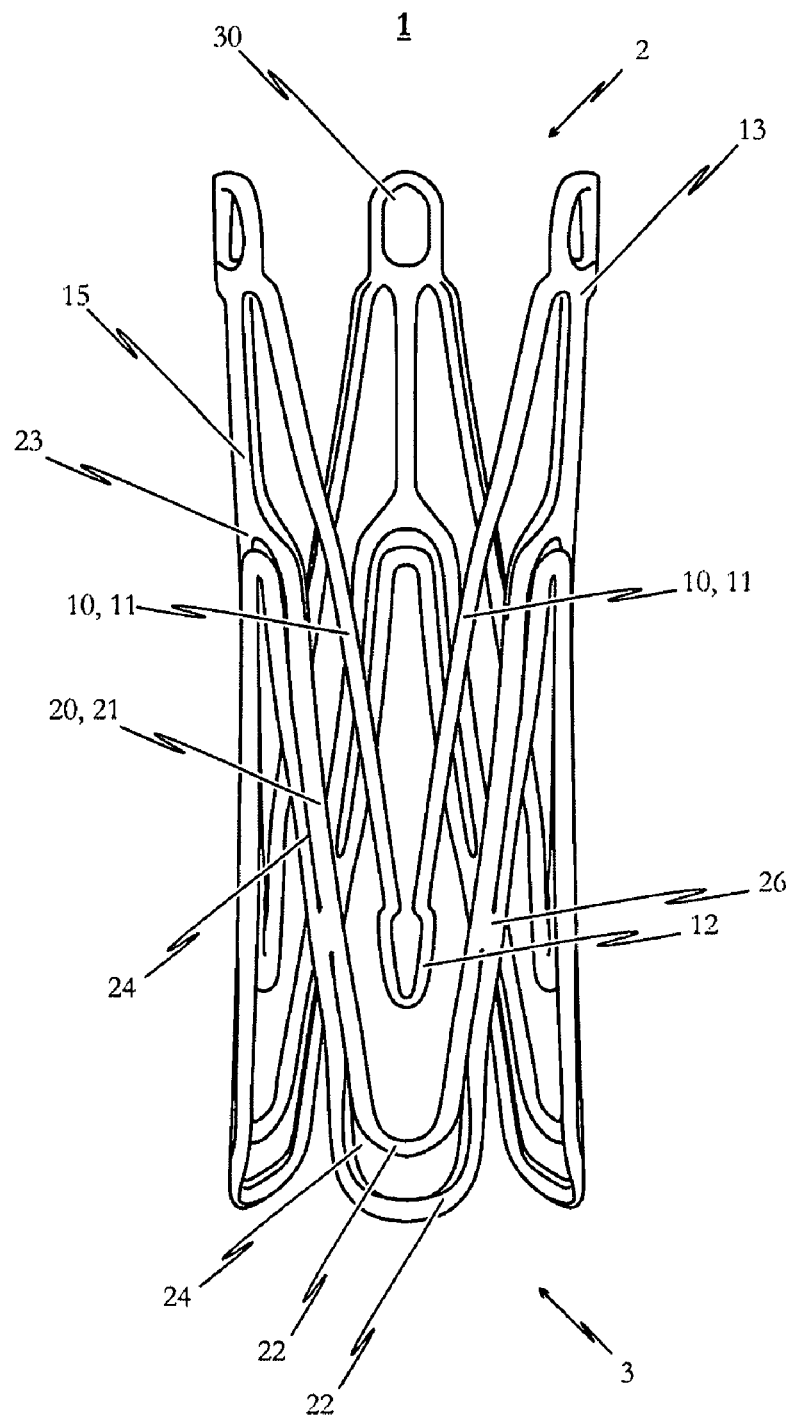
FIG. 1b shows the endoprosthesis illustrated in FIG. 1a but in a state between its first pre-definable mode and its second mode in which the medical device is in its expanded state.
Figure 1C:
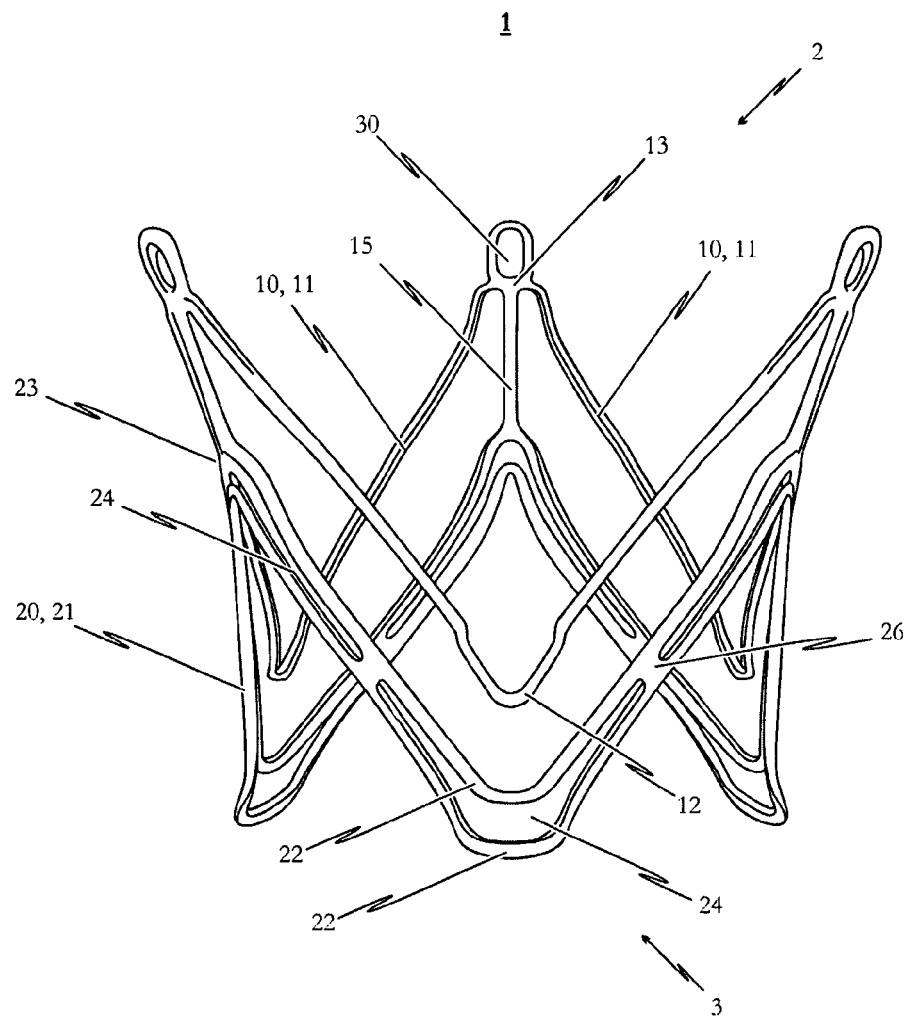
FIG. 1c shows the endoprosthesis illustrated in FIG. 1a but in its second mode in which the medical device is in its expanded state.
Figure 1D:
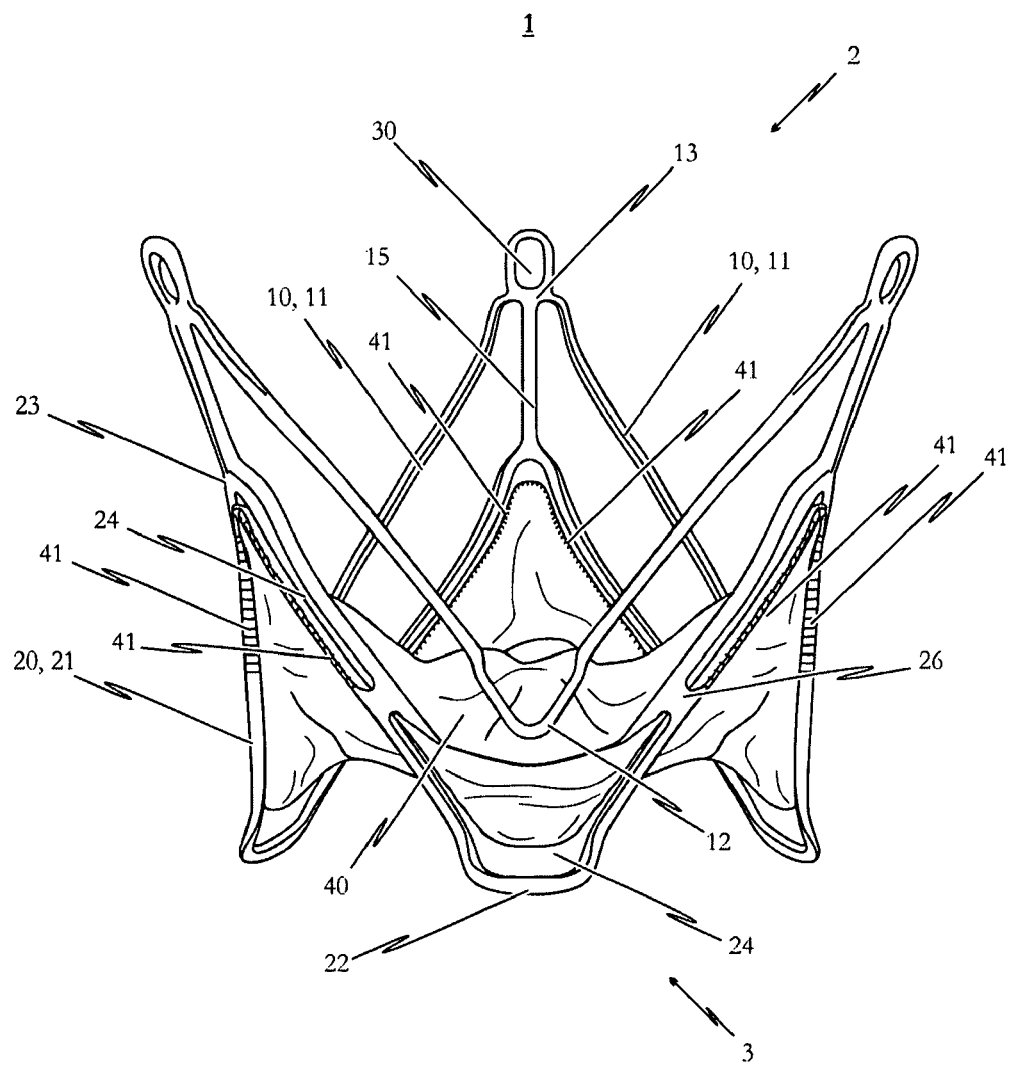
FIG. 1d shows a first, preferred embodiment of the medical device proposed by the invention in its expanded state, with an endoprosthesis of the type illustrated in FIG. 1c with a heart valve prosthesis attached to it and opened out.
Figure 1E:
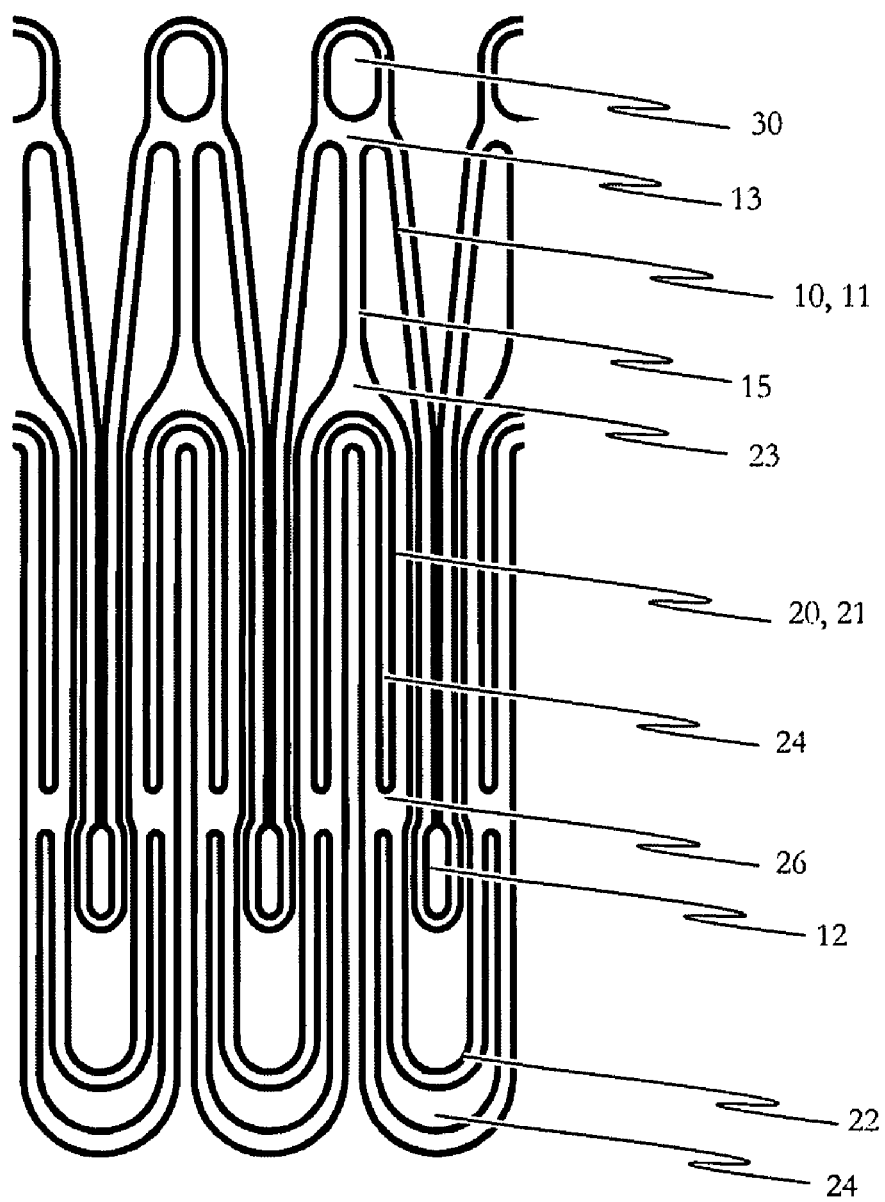
FIG. 1e is a flat projection of a cutting pattern which can be used for the production of the first, preferred, self-expandable endoprosthesis in order to cut the endoprosthesis illustrated in FIG. 1a integrally from a metal tube.

A first preferred embodiment of the self-expandable endoprosthesis 1 for the medical device proposed by the invention will be described first of all with reference to FIG. 1a to 1e. FIG. 1a illustrates the endoprosthesis 1 in its first pre-definable mode in which the medical device (not explicitly illustrated) is in a collapsed state and can therefore be introduced into a patient's body with minimal invasion by means of a catheter system. FIG. 1c illustrates the endoprosthesis 1 in its second mode in which the medical device is in its expanded state. FIG. 1b illustrates the endoprosthesis 1 in a state between the first mode (see FIG. 1a) and the second mode (see FIG. 1c). FIG. 1d illustrates a first preferred embodiment of the medical device proposed by the invention in its expanded state with an endoprosthesis of the type illustrated to FIG. 1c and a heart valve prosthesis attached to it and secured.

The endoprosthesis 1 based on the first preferred embodiment is distinctive due to the fact that it has a structure which is cut integrally from a metal tube. The cutting pattern used to produce the stent design is illustrated in a flat projection in FIG. 1e. Specifically, the endoprosthesis 1 comprises a total of three positioning arches 10, which assume the function of automatically positioning the medical device in the patient's aorta. The positioning arches 10 have a rounded head portion 12, which engages in the pockets of the insufficient heart valve to be replaced by the medical device when the medical device is positioned at the implantation site. Providing three positioning arches 10 in total ensures that the requisite positioning accuracy can be obtained in the direction of rotation.

The head portions 12 of the positioning arches 10 pointing respectively towards the proximal end 3 of the endoprosthesis 1 are appropriately rounded so that the vessel wall is not damaged when the positioning arches 10 engage in the pockets of the heart valve to be replaced. Extending from the head portion 12 of the positioning arch 10 to the distal end 2 of the endoprosthesis 1 are two positioning webs or arms 11 in total for each positioning arch 10, which merge into an eye-shaped element 30 at the distal end 2 of the endoprosthesis 1. This eye-shaped element 30 serves as a fixing means for attaching the endoprosthesis 1 and hence the medical device to an introduction catheter system.

Specifically, the respective fixing eyes 30 are disposed between the two arms 11 of two mutually adjacent positioning arches 10. Opening into the transition portion 13 between the two arms 11 of two mutually adjacent positioning arches 10 incorporating the fixing eye 30 is a connecting web 15 extending essentially in the longitudinal direction of the endoprosthesis 1. At the proximal end, the connecting web 15 merges into the respective retaining arms 21 of two mutually adjacent retaining arches 20.

As a result of this stent design, an axially symmetrical structure is obtained, whereby a retaining arch 20 is associated with each positioning arch 10. The endoprosthesis 1 in the preferred embodiment illustrated in FIGS. 1a to 1c therefore has a total of three retaining arms 20, which form the base for a retaining segment of the endoprosthesis 1 for accommodating a heart valve prosthesis 40 (illustrated in FIG. 1d, for example). Providing the respective connecting webs 15 between the distally lying transition portions 23 of two mutually adjacent retaining arches 20 and the transition portions 13 of two mutually adjacent positioning arches 10 results in a stent structure whereby the respective arms 11 of a positioning arch 10 extend essentially parallel with the respective arms 21 of a retaining arch 20 associated with the positioning arch 10.

When the endoprosthesis 1 is in the state illustrated in FIG. 1a in which it assumes its first mode, the respective arms 11 of the positioning arches 10 directly bound the respective arms 21 of the associated retaining arches 20.

Particular attention should be paid to FIG. 1c in which the endoprosthesis 1 based on the first preferred embodiment is illustrated in its second mode. Particularly worth mentioning in respect of this diagram is the fact that every positioning arch 10 and its associated retaining arch 20 has an essentially U-shaped or V-shaped structure which is closed towards the proximal end 3 of the endoprosthesis 1. Specifically, every positioning arch 10 is cut from the material portion of the metal tube which is accommodated in the essentially U-shaped or V-shaped structure of the associated retaining arch 20, as may be seen from the cutting pattern illustrated in FIG. 1e.

As may be seen by comparing FIGS. 1a and 1c, during the transition from the first mode into the second mode, the endoprosthesis becomes shorter in the longitudinal direction whilst the cross-section simultaneously becomes wider, in particular at the distal and the proximal retaining regions 2, 3. When the endoprosthesis 1 is in the expanded state, the respective positioning arches 10 are specifically opened out to a more pronounced degree in the radial direction than is the case at the distal retaining region 2 of the stent 1. The positioning arches 10 which assume the function of positioning the medical device in the implanted state by engaging in the pockets of the old heart valve to be replaced can therefore project farther out in the radial direction and can be inserted in the heart valve pockets of the heart valve to be replaced in a particularly easy manner.

FIG. 1d illustrates a first preferred embodiment of the medical device proposed by the invention in its expanded state, with an endoprosthesis 1 of the type illustrated in FIG. 1c and a heart valve prosthesis 40 attached to with the aid of a thread 41 and opened out. As illustrated, opening out the proximal retaining region 3 of the endoprosthesis 1 in which the heart valve prosthesis 40 is disposed causes the heart valve prosthesis 40 to open out, whilst a radial force is simultaneously applied to the vessel wall (not illustrated) by the proximal end portions 22 of the retaining arches 21, thereby affording a reliable seal of the heart valve prosthesis 40 with respect to the vessel wall.

Although the force exerted by the retaining arches 21 in the radial direction onto the vessel wall causes the medical device to be secured at the implantation site to a certain extent, the distal retaining region 2 is expanded by a further 10% to 25% in the radial direction than is the case at the proximal retaining region 3 of the endoprosthesis 1 when the medical device is in the expanded state in order to obtain a permanently stable implantation of the medical device, especially in view of the unavoidable peristaltic movement of the vessel wall and the relatively high fluid pressures which prevail. As a result, a slightly concave shape is imparted to the endoprosthesis 1, which tapers in the direction of the proximal retaining region 3 of the endoprosthesis 1, thereby ensuring that the medical device is firmly anchored in the vessel due to the distal retaining region 2 of the endoprosthesis 1 pressing against the vessel wall.

In the embodiment illustrated, the respective arms 21 of the retaining arches 20 have uninterrupted slots or elongate holes 24, the purpose of which is to enable or assist expansion of the endoprosthesis 1 from the collapsed state into the expanded state, because these slots or elongate holes 24 make it easy to widen the cross-section of the stent 1 whilst simultaneously reducing its length. Naturally, however, it would also be conceivable for these slots or elongate holes 24 to accommodate a thread 41 or similar used to attach the heart valve prosthesis 40 (illustrated in FIG. 1d) to the proximal region 3 of the endoprosthesis 1.

The solution proposed by the invention is a medical device of a modular design essentially comprising the two separately manufactured components, endoprosthesis 1 and heart valve prosthesis 40, and the endoprosthesis 1 assumes the function of positioning and securing the heart valve prosthesis 40 in the patient's aorta. It may be preferable if the two components (endoprosthesis 1 and heart valve prosthesis 40) are not connected to one another until immediately prior to performing the surgical intervention; this is of advantage in terms of transporting and storing the endoprosthesis 1 as such since the endoprosthesis 1 is a relatively robust component from a mechanical point of view and in particular can be stored for a longer period. This applies in particular if the endoprosthesis 1 is stored in its second mode, i.e. in the expanded state, and is not switched to its first (collapsed) mode until immediately prior to undertaking the surgical intervention.

The state of the endoprosthesis 1 illustrated in FIG. 1a in which the endoprosthesis 1 is in its first mode and the medical device is in its collapsed state is the so-called "temporary" mode of the endoprosthesis structure made from a memory shape material. When an external stimulus acts on the endoprosthesis body illustrated in FIG. 1a, the shape memory effect is triggered and the fixed permanent shape memorised during production of the endoprosthesis 1 illustrated in FIG. 1c is restored. This external stimulus is preferably a settable switching temperature and the body must be heated to a temperature higher than the switching temperature in order to trigger the shape memory effect and thus restore the memorised permanent shape of the endoprosthesis 1. By selecting the chemical composition of the material used for the endoprosthesis 1 accordingly, a specific switching temperature can be fixed beforehand; in the case of the preferred embodiment of the solution proposed by the invention, it lies in a range of between 20° C. and the body temperature of the patient.

When the medical device is being implanted, it would therefore be conceivable for the medical device to be cooled accordingly during the introduction process. When the medical device has been moved to the desired implantation site, in other words in front of the native heart valve, preferably by means of an appropriate introduction system, cooling can be interrupted so that the endoprosthesis 1 of the medical device is heated to the body temperature (36° C.) of the patient, thereby triggering the shape memory effect of the endoprosthesis material. Having triggered the self-expanding property of the endoprosthesis 1, radial forces are generated which act on the individual components of the endoprosthesis 1 and in particular on the respective positioning arches 10, 11 and retaining arches 20, 21 of the endoprosthesis 1. Since the endoprosthesis 1 of the medical device is still disposed in the introduction catheter system as before, the radial forces which build up once the critical switch temperature is exceeded and act on the individual components of the endoprosthesis 1 are still compensated by the introduction port of the introduction catheter system so that—in spite of the shape memory effect having been triggered—the endoprosthesis 1 of the medical device is forcibly retained in its first (collapsed) mode.

By releasing the endoprosthesis 1 from the introduction catheter system in appropriate steps, it is then possible to release the positioning arches 10, 111 of the endoprosthesis 1 through the introduction port of the introduction catheter system first, as a result of which it opens up due to the radial forces acting in the radial direction. The opened positioning arches 10, 11 can then be positioned in the pockets of the native heart valve.

The remaining components of the endoprosthesis 1 and the medical device can then be released through the introduction port of the introduction catheter system. As this happens, the retaining arches 20, 21 open in the radial direction and the heart valve prosthesis 40 attached to the retaining arches 20, 21 by means of a thread 41, etc., for example, thus unfolds in the manner of an umbrella. The radial forces acting on the retaining arches 20, 21 but also on the distal retaining region 2 of the endoprosthesis 1 cause the endoprosthesis 1 to be pressed in the radial direction against the vessel wall, which guarantees a reliable anchoring of the medical device at the implantation site on the one hand and ensures a reliable seal of the heart valve prosthesis 40 at the proximal retaining region 3 of the endoprosthesis 1 on the other hand.

Figure 2A:
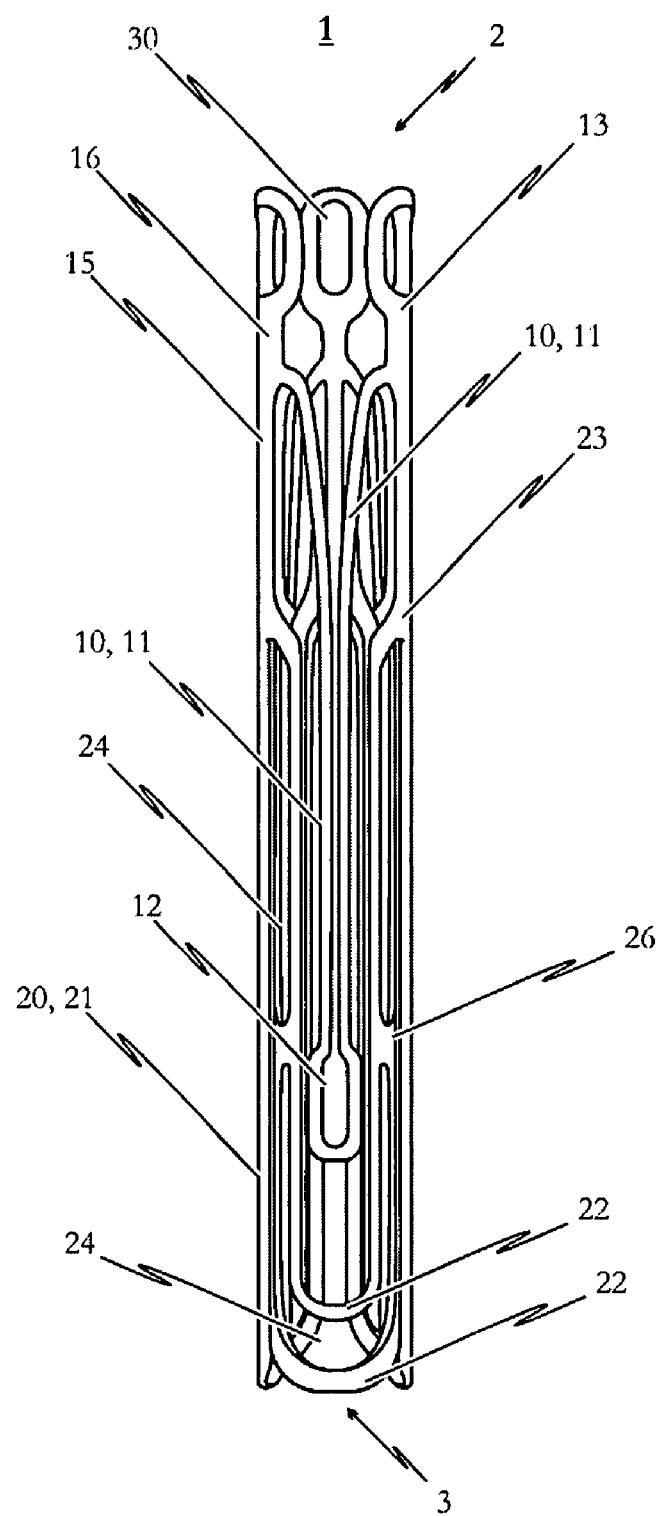
FIG. 2a shows a second, preferred embodiment of a self-expandable endoprosthesis for the medical device proposed by the invention in its first, pre-determined mode in which the medical device is in its collapsed state.
Figure 2B:
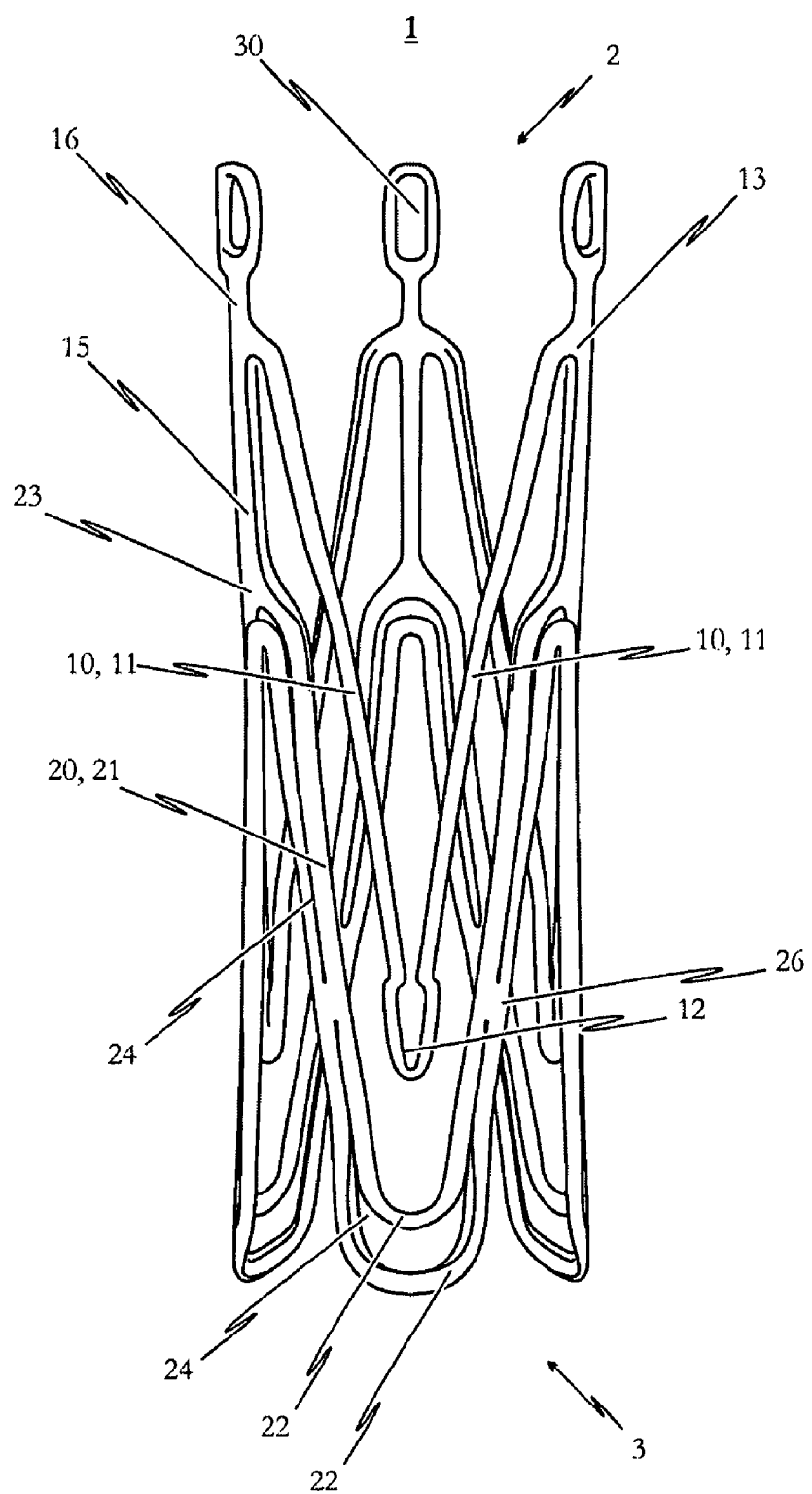
FIG. 2b shows the endoprosthesis illustrated in FIG. 2a in a state between its first, pre-definable mode and its second mode in which the medical device is in its expanded state.
Figure 2C:
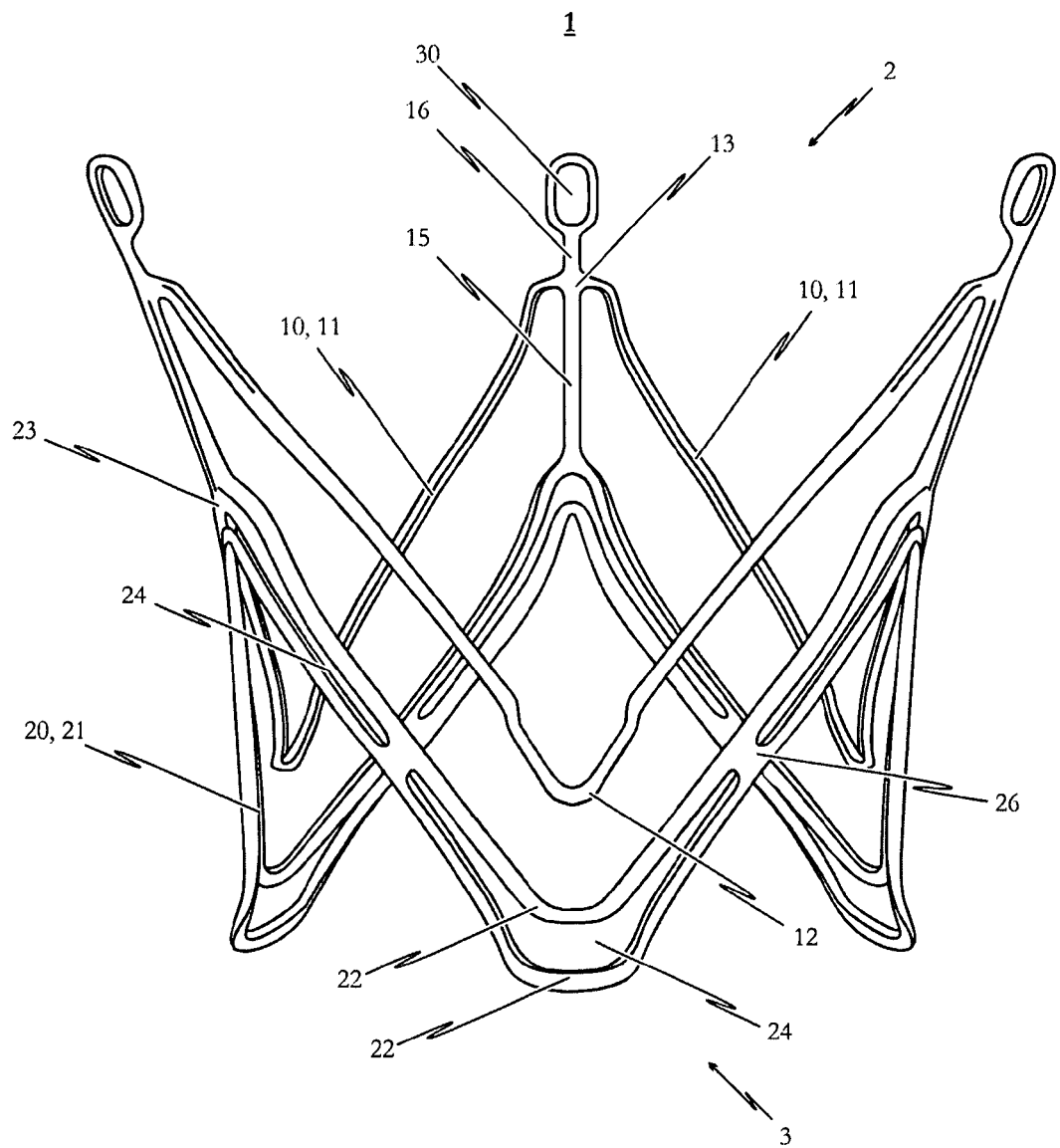
FIG. 2c shows the endoprosthesis illustrated in FIG. 2a in its second mode in which the medical device is in its expanded state.

FIGS. 2a to 2c illustrate a second preferred embodiment of a self-expandable endoprosthesis 1 for the medical device proposed by the invention in its first, pre-definable mode (see FIG. 2a) in its second pre-definable mode (see FIG. 2c) as well as in a state in between (see FIG. 2b).

Figure 2D:
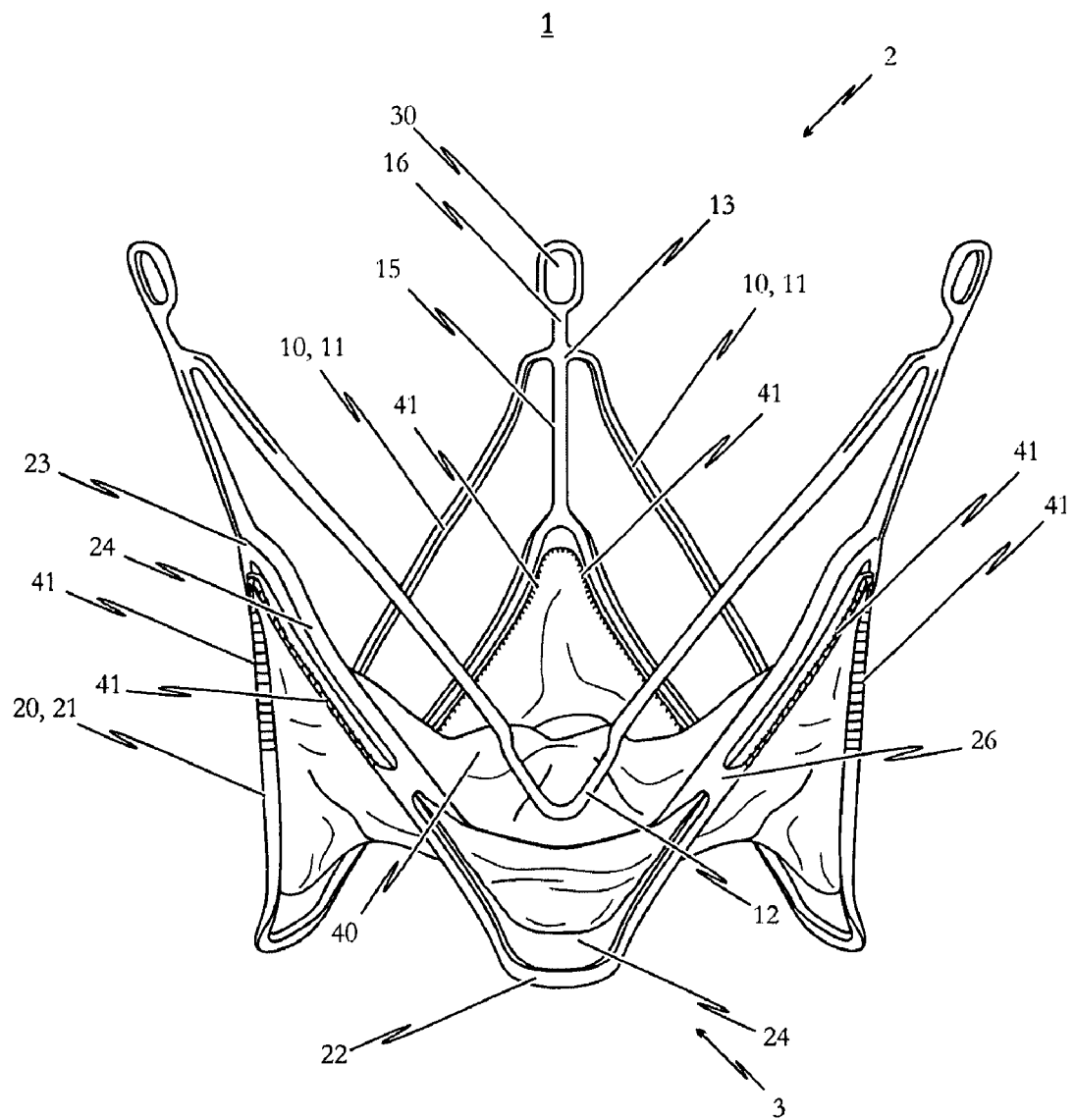
FIG. 2d illustrates a second preferred embodiment of the medical device proposed by the invention in its expanded state, with an endoprosthesis of the type illustrated in FIG. 2c and a heart valve prosthesis attached to it and opened out.
Figure 2E:
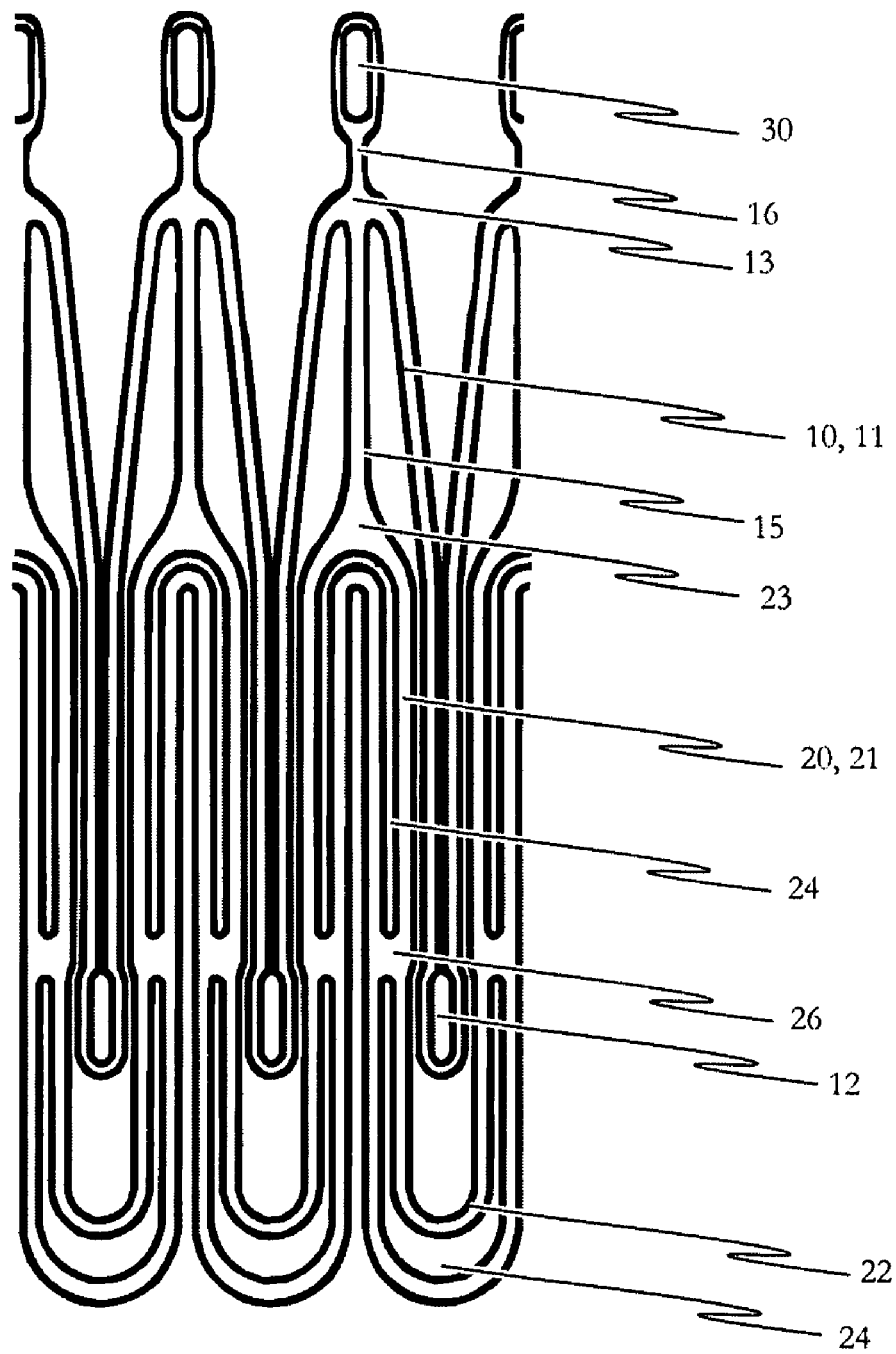
FIG. 2e is a flat projection of a cutting pattern which can be used for the production of the second preferred, self-expandable endoprosthesis in order to cut the endoprosthesis illustrated in FIG. 2a integrally from a metal tube.

FIG. 2d illustrates a second preferred embodiment of the medical device proposed by the invention in its expanded state with an endoprosthesis of the type illustrated in FIG. 2c and a heart valve prosthesis 40 attached to it and opened out. A flat projection of a cutting pattern which may be used for the production of the second preferred embodiment of the self-expandable endoprosthesis is illustrated in FIG. 2e. This cutting pattern is suitable for cutting the endoprosthesis illustrated in FIG. 2a integrally from a metal tube.

The endoprosthesis 1 based on the second preferred embodiment essentially corresponds to the first preferred embodiment described above with reference to FIGS. 1a to 1e. The second embodiment differs from the first preferred embodiment of the endoprosthesis due to the fact that the respective arms 11 of the adjacent positioning arches 10 are joined indirectly via a connecting web 16 extending essentially in the longitudinal direction of the endoprosthesis 1 to the fixing eye 30, and the respective arms 21 of the retaining arches 20 associated with the adjacent positioning arches 10 are indirectly joined via a connecting web 15 extending essentially in the longitudinal direction of the endoprosthesis 1 to the fixing eye 30. Specifically, the connecting web 15 of the retaining arches 20 merges into the connecting web 16 of the positioning arches 10 at the end portion 13 of the positioning arches 10. By selecting the respective lengths of the two connecting webs 15 and 16 accordingly, therefore, the overall length of the stent 1 can be adjusted in an easy manner.

Figure 3A:
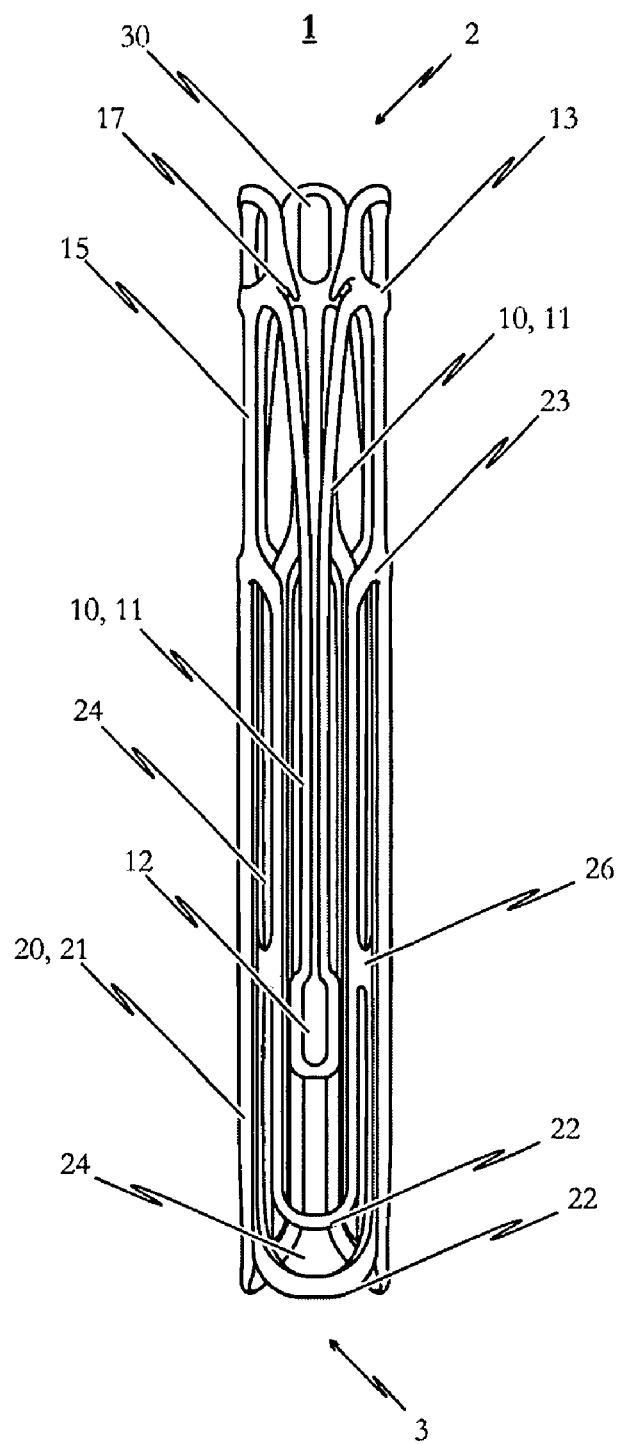
FIG. 3a shows a third, preferred embodiment of a self-expandable endoprosthesis for the medical device proposed by the invention in its first, pre-determined mode in which the medical device is in its collapsed state.
Figure 3B:
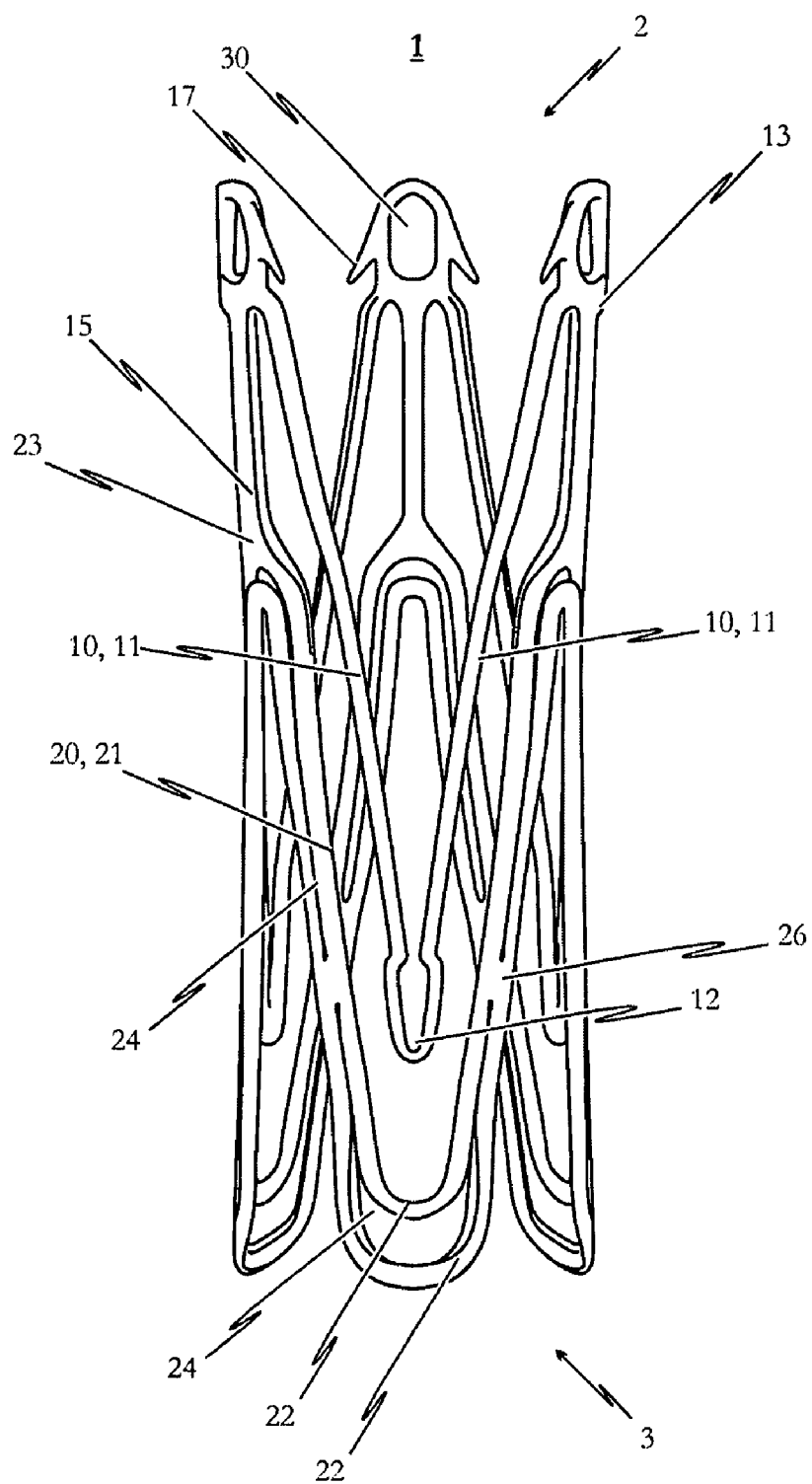
FIG. 3b shows the endoprosthesis illustrated in FIG. 3a in a state between its first, pre-definable mode and its second mode in which the medical device is in its expanded state.
Figure 3C:
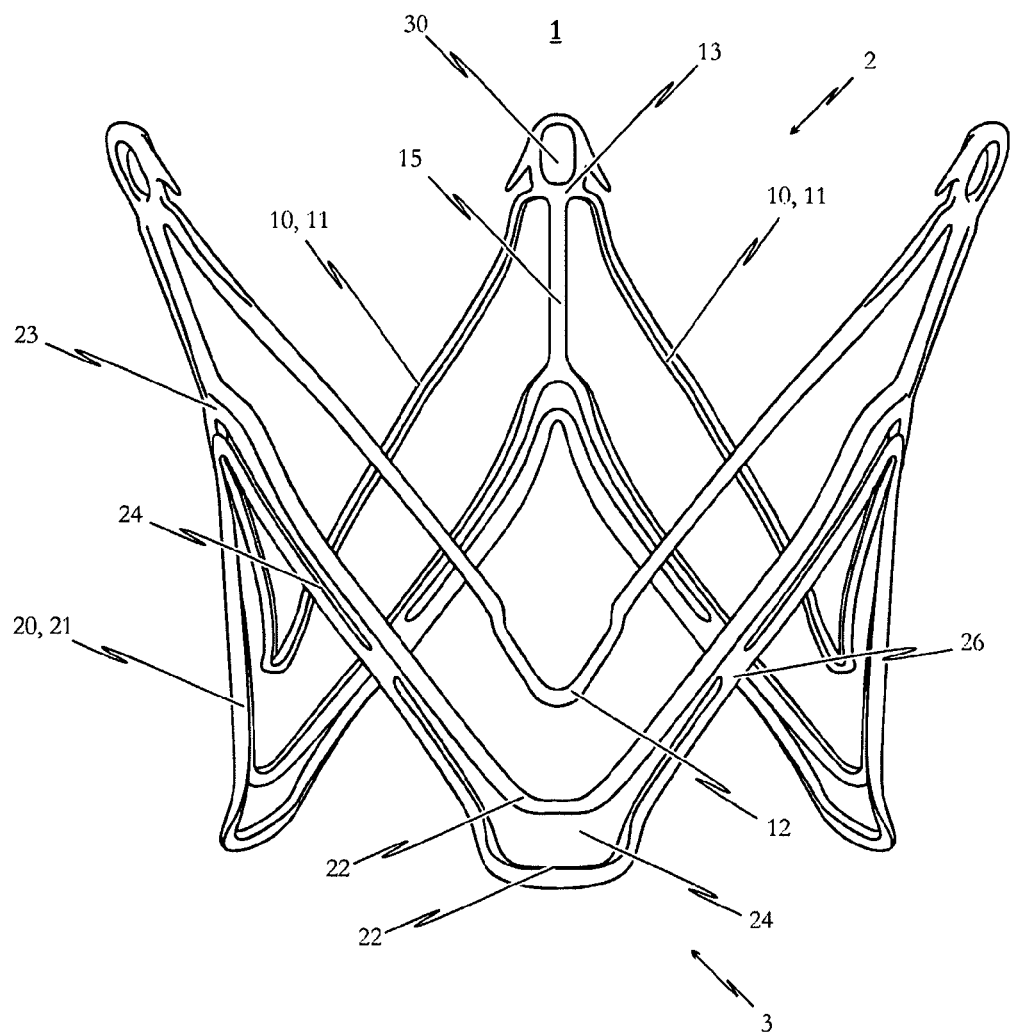
FIG. 3c shows the endoprosthesis illustrated in FIG. 3a in its second mode in which the medical device is in its expanded state.

The third preferred embodiment of a self-expandable endoprosthesis for the medical device proposed by the invention illustrated in FIGS. 3a to 3c essentially corresponds to the first preferred embodiment illustrated in FIGS. 1a to 1c; the difference, however, is that in the third preferred embodiment, the fixing eyes 30 disposed between two adjacent positioning arches 10 are provided with barbs 17, the respective tips of which point in the direction of the proximal end 3 of the endoprosthesis 1. With this modification to the design of the heart valve-stent 1 based on the first preferred embodiment, therefore, additional anchoring is provided for the system to prevent the stent 1 from being dislocated in the direction of the left ventricle.

Figure 3D:
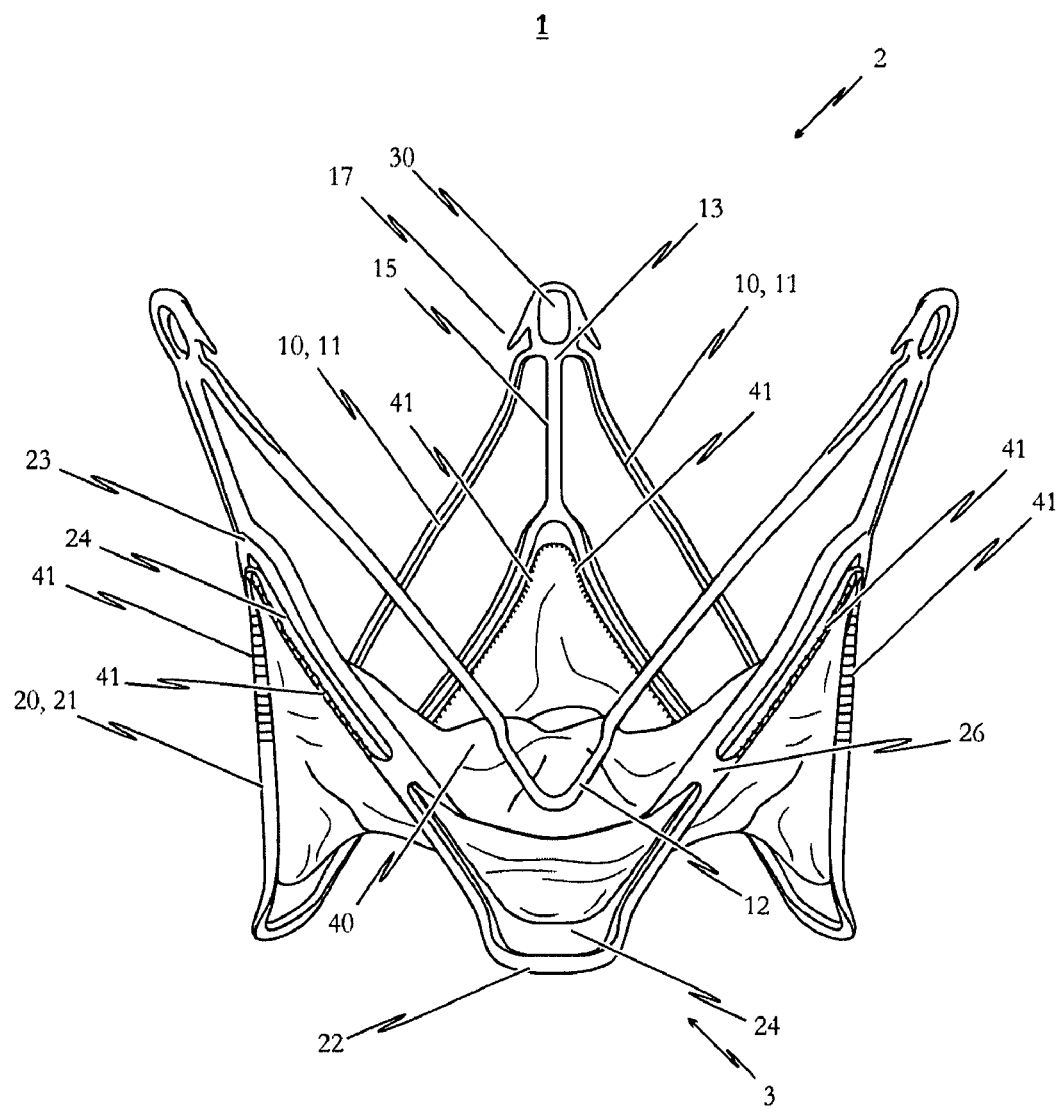
FIG. 3d illustrates a third preferred embodiment of the medical device proposed by the invention in its expanded state, with an endoprosthesis of the type illustrated in FIG. 3c and a heart valve prosthesis attached to it and opened out.

FIG. 3d illustrates a third preferred embodiment of the medical device proposed by the invention in its expanded state with an endoprosthesis of the type illustrated in FIG. 3c and a heart valve prosthesis 40 attached to it and opened out. This diagram essentially corresponds to that of FIG. 1d; the exception, however, is the fact that the barb elements 17 described above are provided on the respective fixing eyes 30.

Figure 3E:
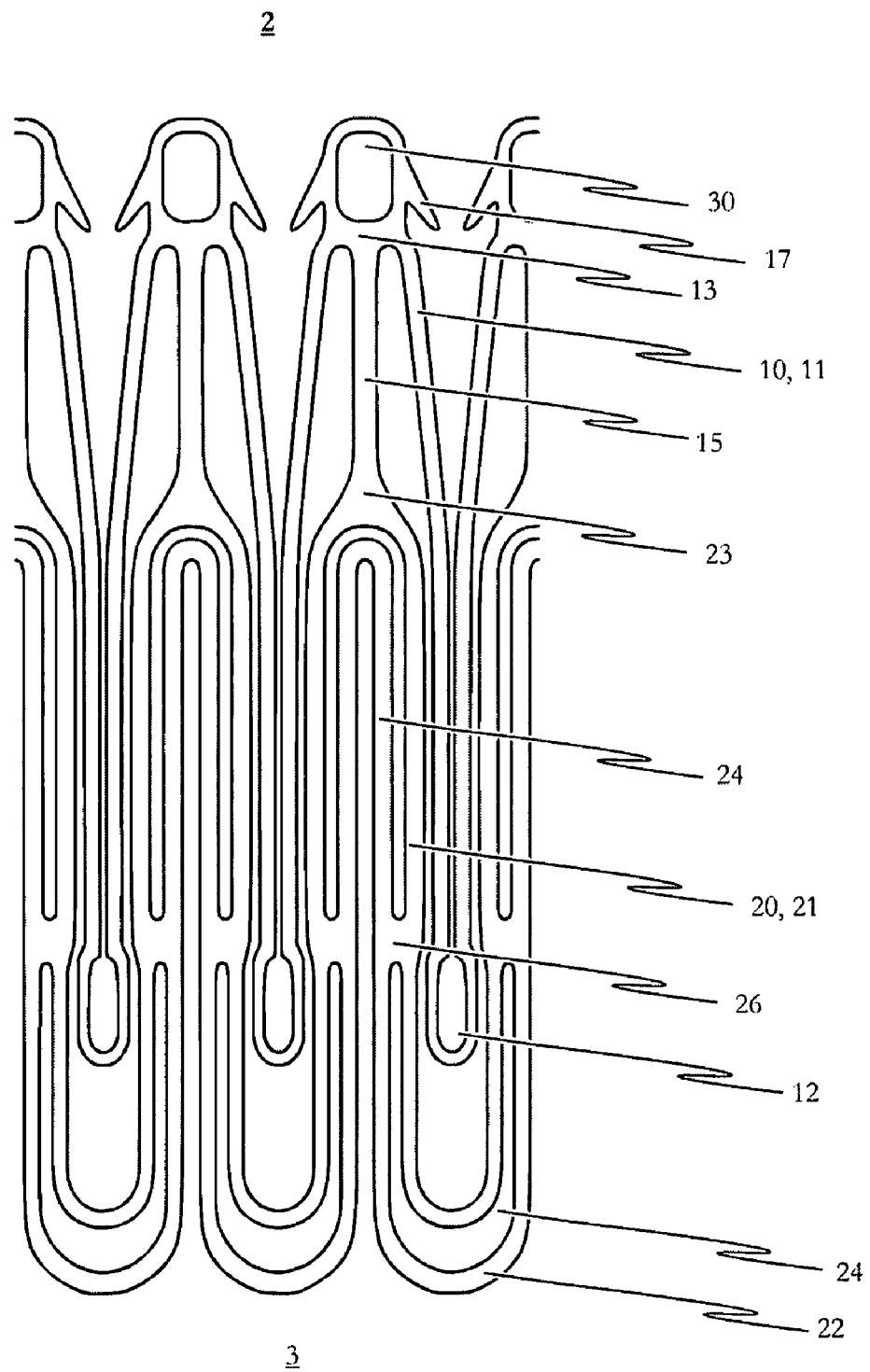
FIG. 3e is a flat projection of a cutting pattern which can be used for the production of the third preferred, self-expandable endoprosthesis in order to cut the endoprosthesis illustrated in FIG. 3a integrally from a metal tube.

A flat projection of a cutting pattern which may be used for the production of the third preferred embodiment of the self-expandable endoprosthesis 1 is illustrated in FIG. 3e. This cutting pattern is suitable for cutting the endoprosthesis illustrated in FIG. 3a integrally from a metal tube.

Figure 4A:
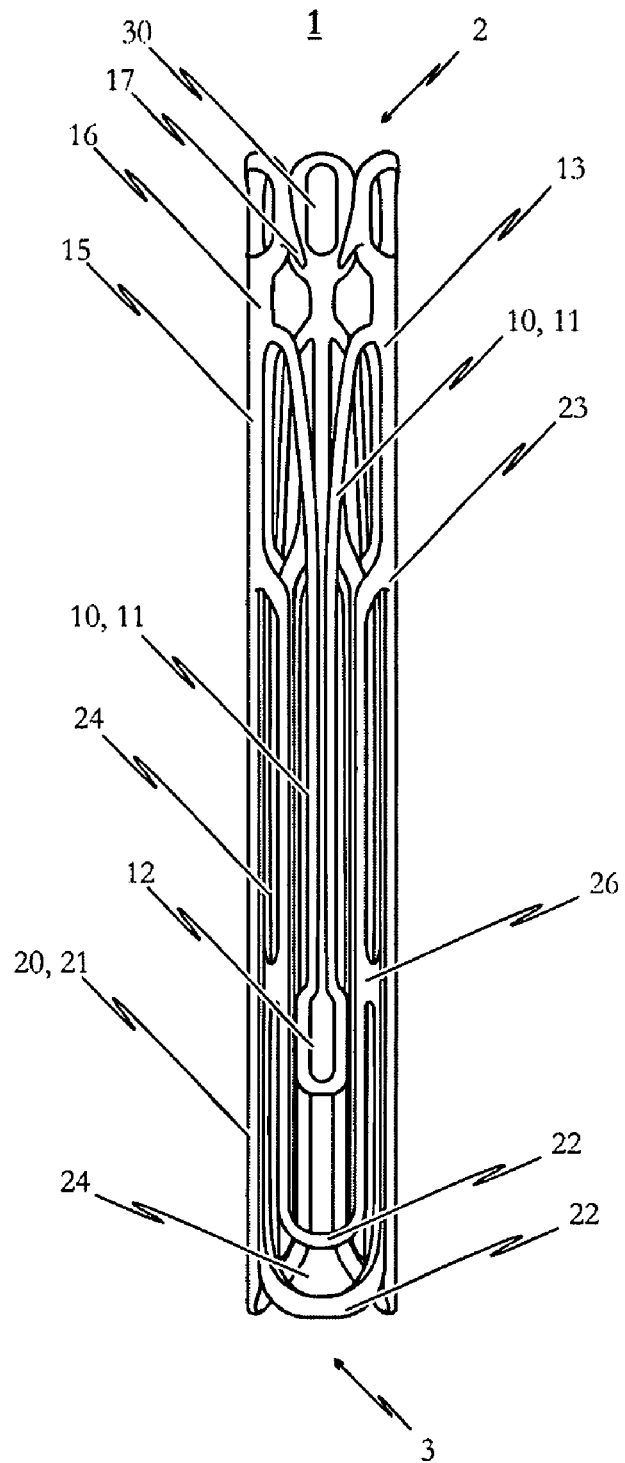
FIG. 4a shows a fourth, preferred embodiment of a self-expandable endoprosthesis for the medical device proposed by the invention in its first, pre-determined mode in which the medical device is in its collapsed state.
Figure 4B:
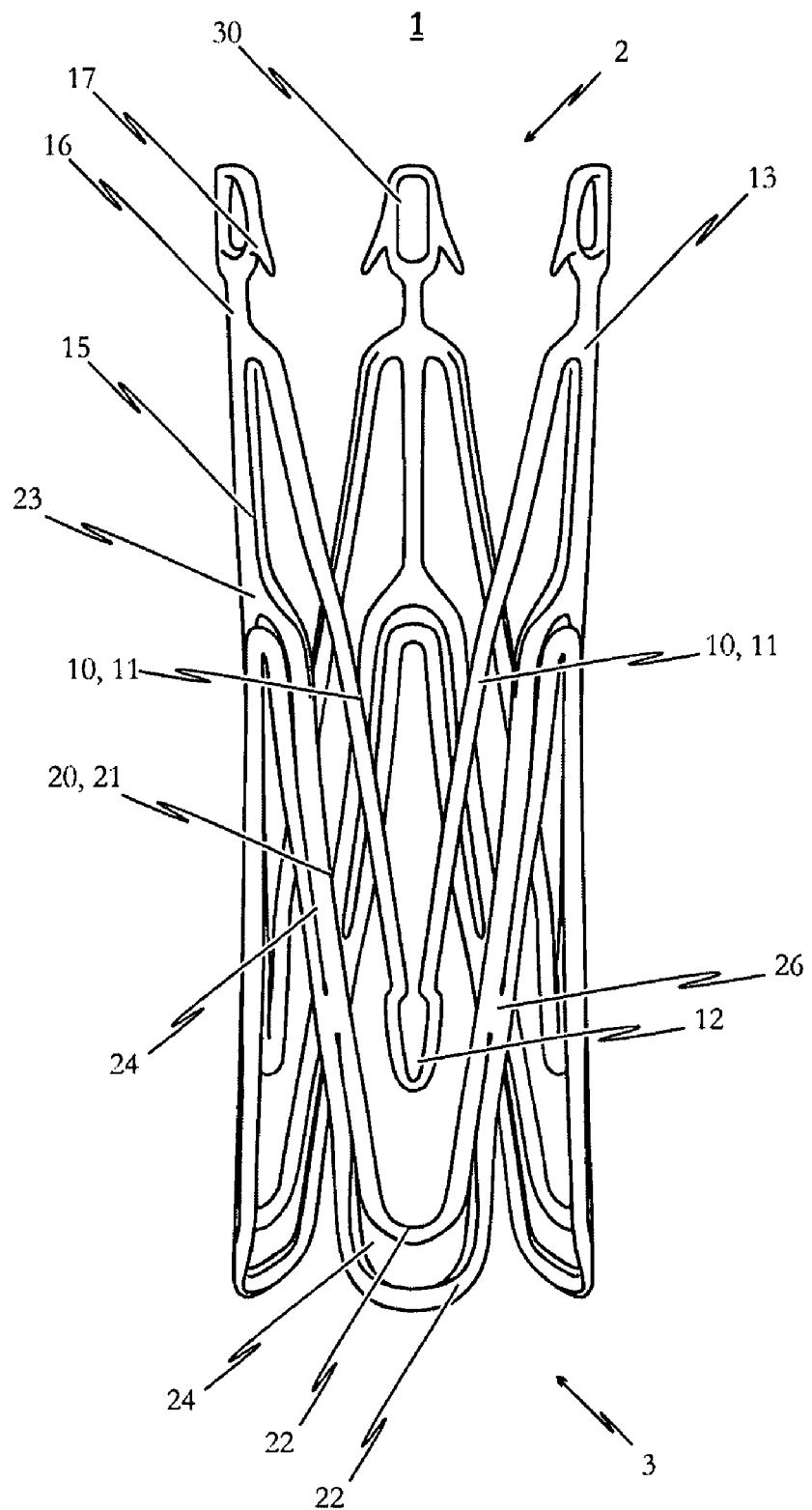
FIG. 4b shows the endoprosthesis illustrated in FIG. 4a in a state between its first, pre-definable mode and its second mode in which the medical device is in its expanded state.
Figure 4C:
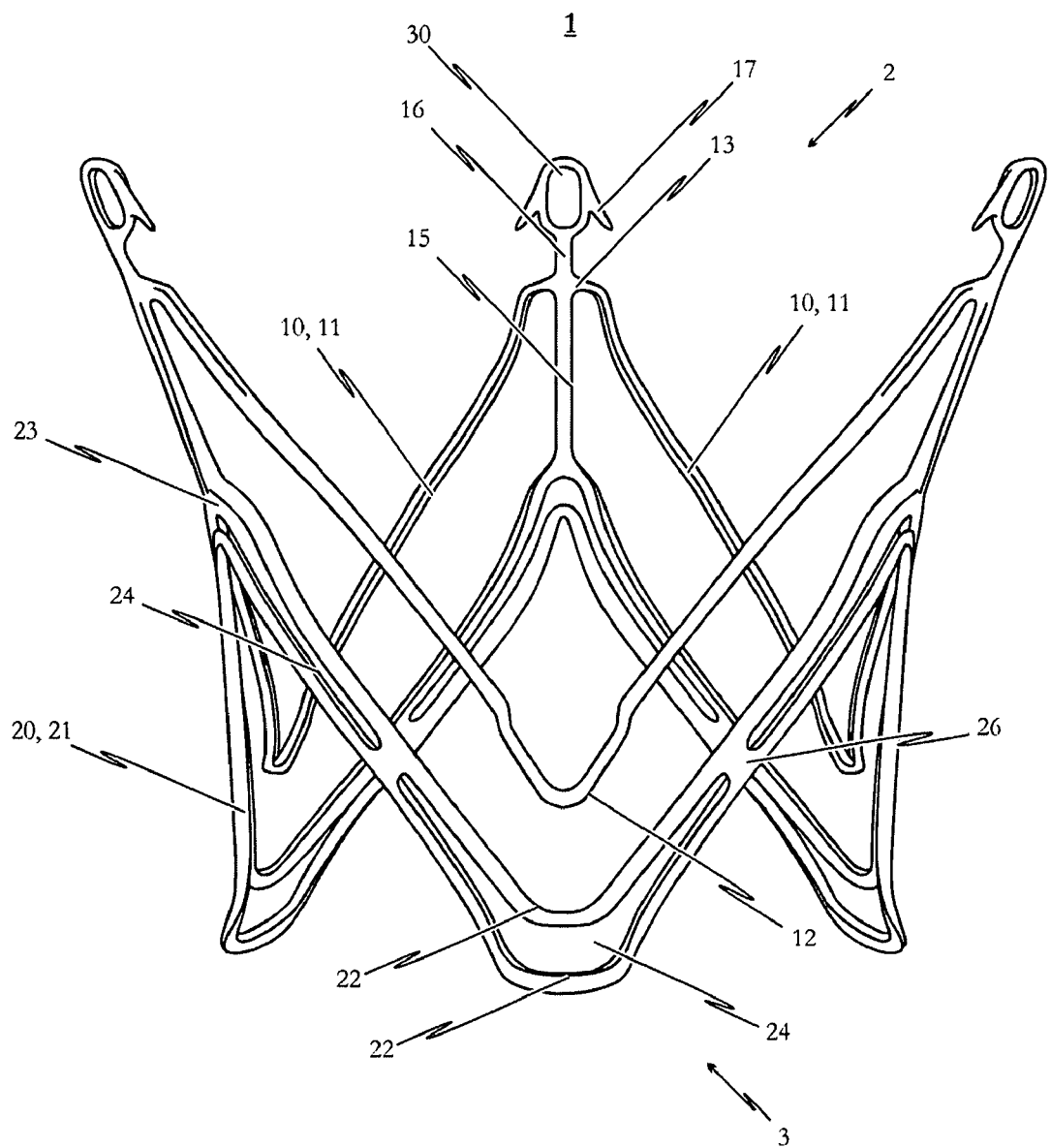
FIG. 4c shows the endoprosthesis illustrated in FIG. 4a in its second mode in which the medical device is in its expanded state.
Figure 4D:
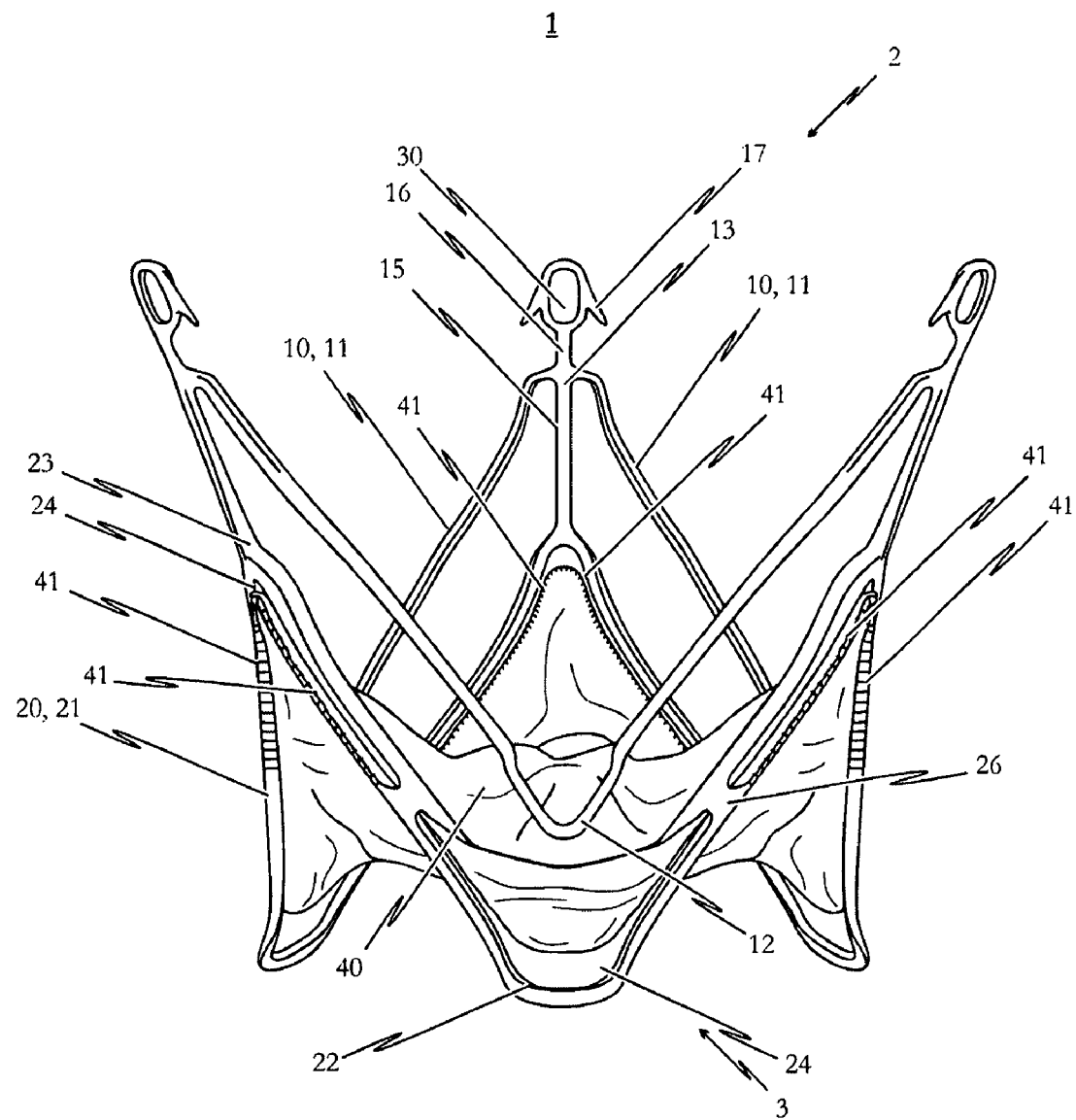
FIG. 4d illustrates a fourth preferred embodiment of the medical device proposed by the invention in its expanded state, with an endoprosthesis of the type illustrated in FIG. 4c and a heart valve prosthesis attached to it and opened out.
Figure 4E:
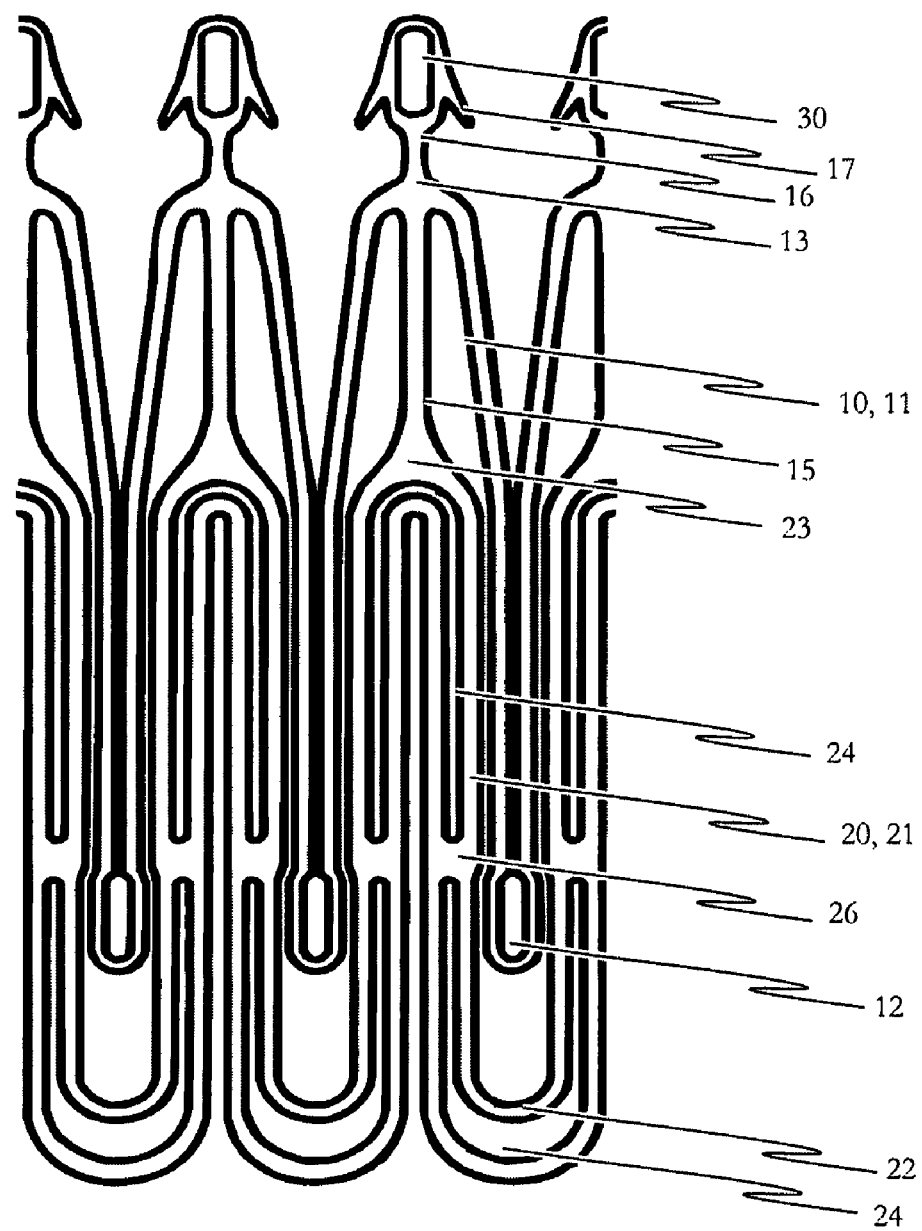
FIG. 4e is a flat projection of a cutting pattern which can be used for the production of the fourth, preferred, self-expandable endoprosthesis in order to cut the endoprosthesis illustrated in FIG. 4a integrally from a metal tube.

FIG. 4a to FIG. 4c illustrate a fourth preferred embodiment of a self-expandable endoprosthesis 1 for the medical device proposed by the invention. A fourth preferred embodiment of the medical device proposed by the invention is illustrated in its expanded state with an endoprosthesis in FIG. 4c and an opened out heart valve prosthesis 40 attached to it is illustrated in FIG. 4d, whilst FIG. 4e illustrates a flat projection of a cutting pattern, which may be used for the production of the fourth preferred embodiment of the self-expandable endoprosthesis 1. The cutting pattern illustrated in FIG. 4e is specifically suitable for cutting the endoprosthesis illustrated in FIG. 4a integrally from a metal tube.

The fourth preferred embodiment of the self-expandable prosthesis 1 corresponds to a combination of the second and third preferred embodiments described above. Specifically, the respective arms 11 of the adjacent positioning arches 10 are indirectly joined via the connecting web 16 extending essentially in the longitudinal direction of the endoprosthesis to the fixing eye 30, whilst barbs 17 are provided on the respective fixing eyes 30, the tips of which point in the direction of the proximal end 3 of the endoprosthesis 1. The advantages which can be achieved as a result of the features provided on the fourth preferred embodiment were described above and will not be reiterated at this stage.

The fifth preferred embodiment of a self-expandable endoprosthesis 1 and a medical device proposed by the invention illustrated in FIG. 5a to FIG. 5e essentially corresponds to the first preferred embodiment described with reference to FIG. 1a to FIG. 1e, except that in this instance, the respective retaining arches 21 of the endoprosthesis 1 are provided with reinforcing portions 26, which interrupt the slots 24 extending in the longitudinal direction of the retaining arches 21. The purpose of these reinforcing portions 26 is to open out the individual components of the retaining arches 21, and in particular to break the anchoring support 25 radially out of the retaining arches 20. Accordingly, a retaining portion for the stent 1 can be obtained with the reinforcing portions 26, which has no components which might explant the medical device when it is in the expanded state.

Figure 5A:
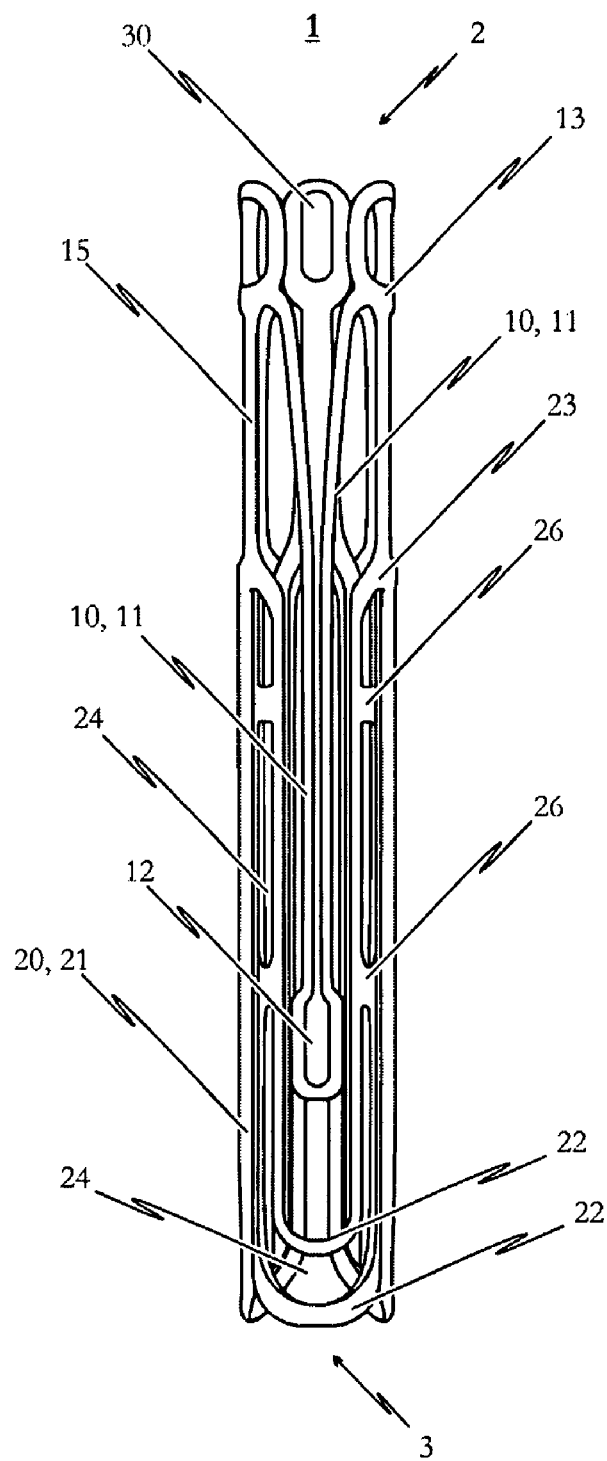
FIG. 5a shows a fifth preferred embodiment of a self-expandable endoprosthesis for the medical device proposed by the invention in its first, pre-determined mode in which the medical device is in its collapsed state.
Figure 5B:
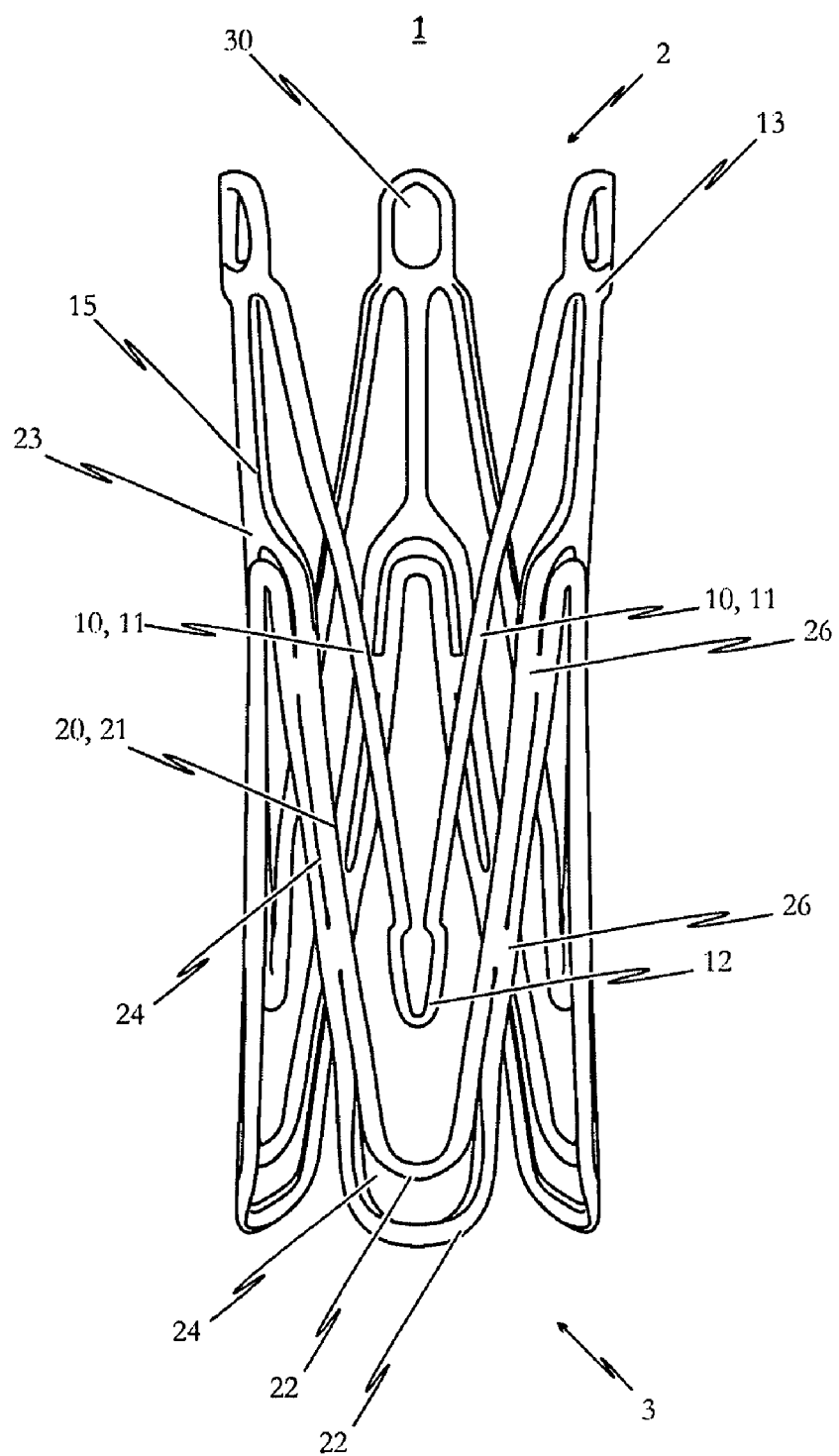
FIG. 5b shows the endoprosthesis illustrated in FIG. 5a in a state between its first, pre-definable mode and its second mode in which the medical device is in its expanded state.
Figure 5C:
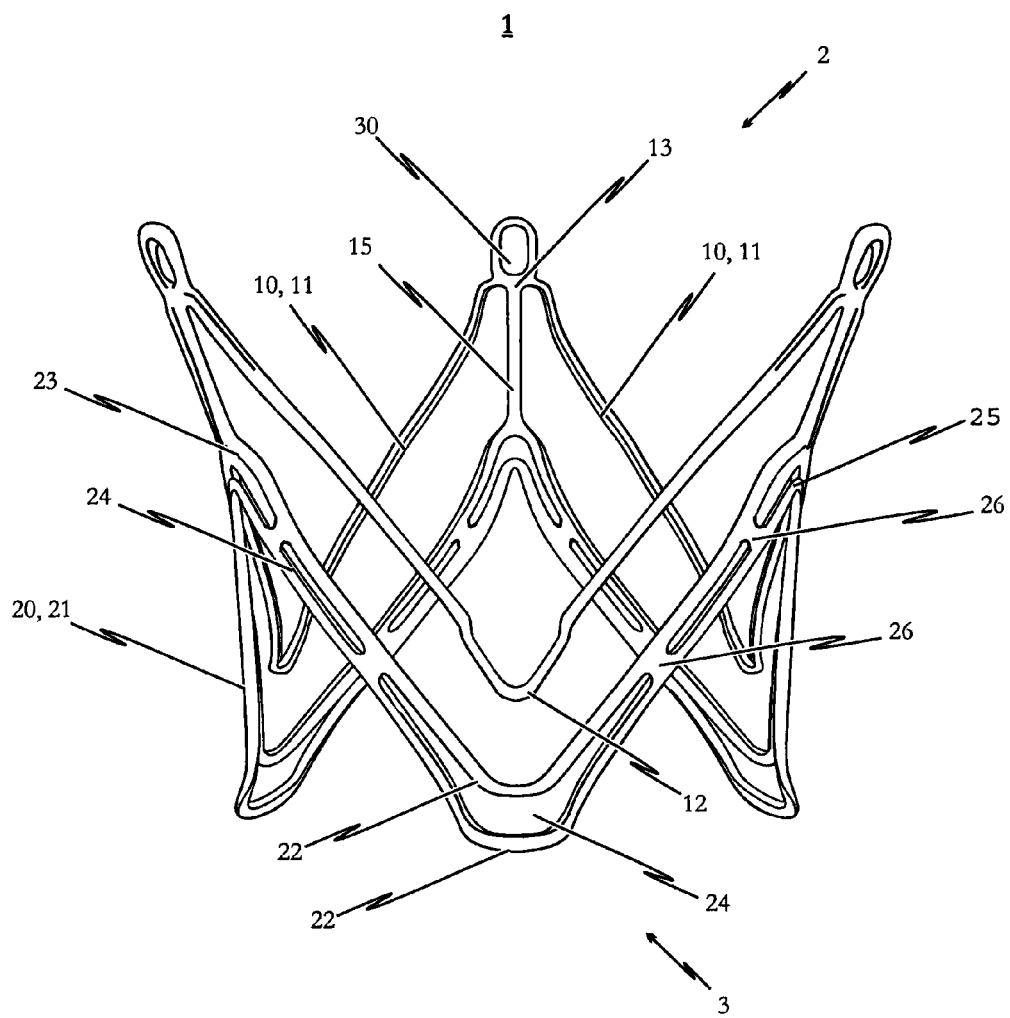
FIG. 5c shows the endoprosthesis illustrated in FIG. 5a in its second mode in which the medical device is in its expanded state.
Figure 5D:
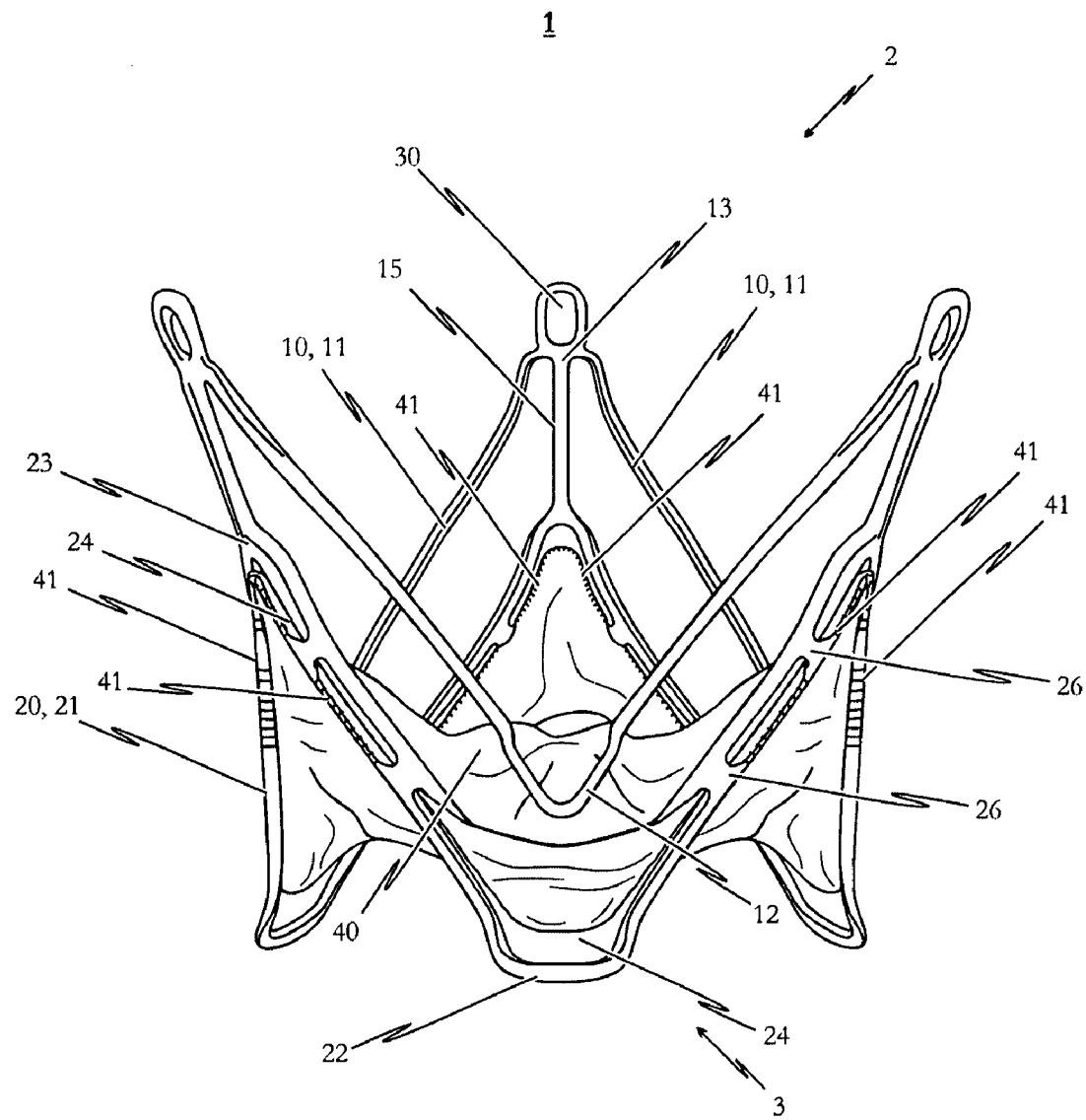
FIG. 5d illustrates a fifth preferred embodiment of the medical device proposed by the invention in its expanded state, with an endoprosthesis of the type illustrated in FIG. 5c and a heart valve prosthesis attached to it and opened out.
Figure 5E:
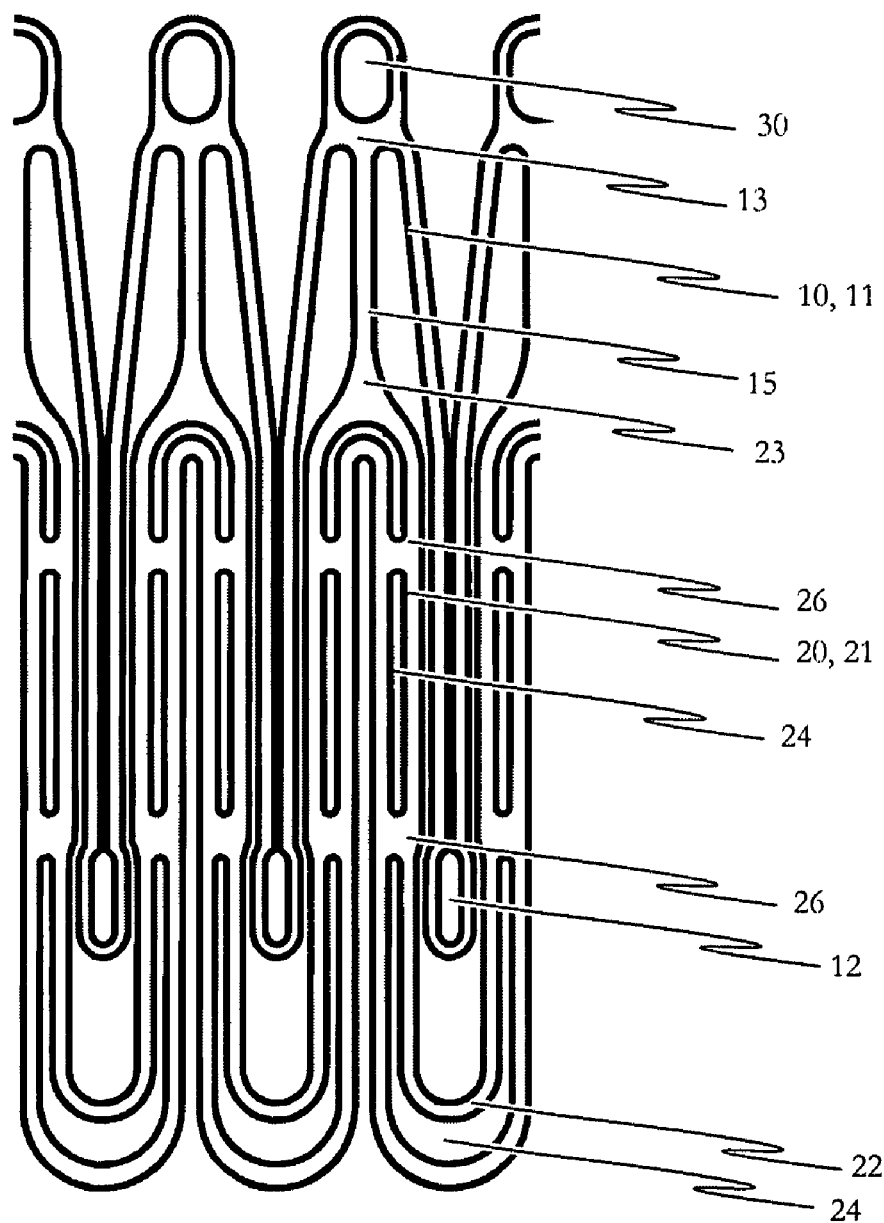
FIG. 5e is a flat projection of a cutting pattern which can be used for the production of the fifth, preferred, self-expandable endoprosthesis in order to cut the endoprosthesis illustrated in FIG. 5a integrally from a metal tube.
Figure 6A:
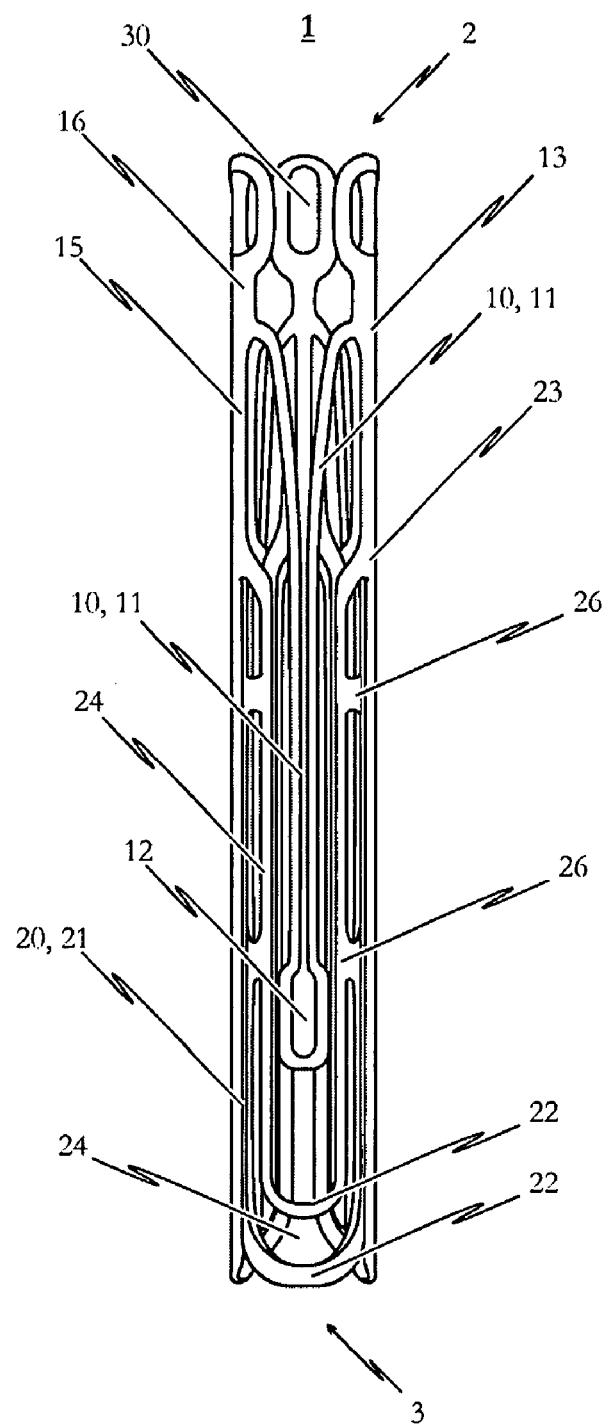
FIG. 6a shows a sixth preferred embodiment of a self-expandable endoprosthesis for the medical device proposed by the invention in its first, pre-determined mode in which the medical device is in its collapsed state.
Figure 6B:
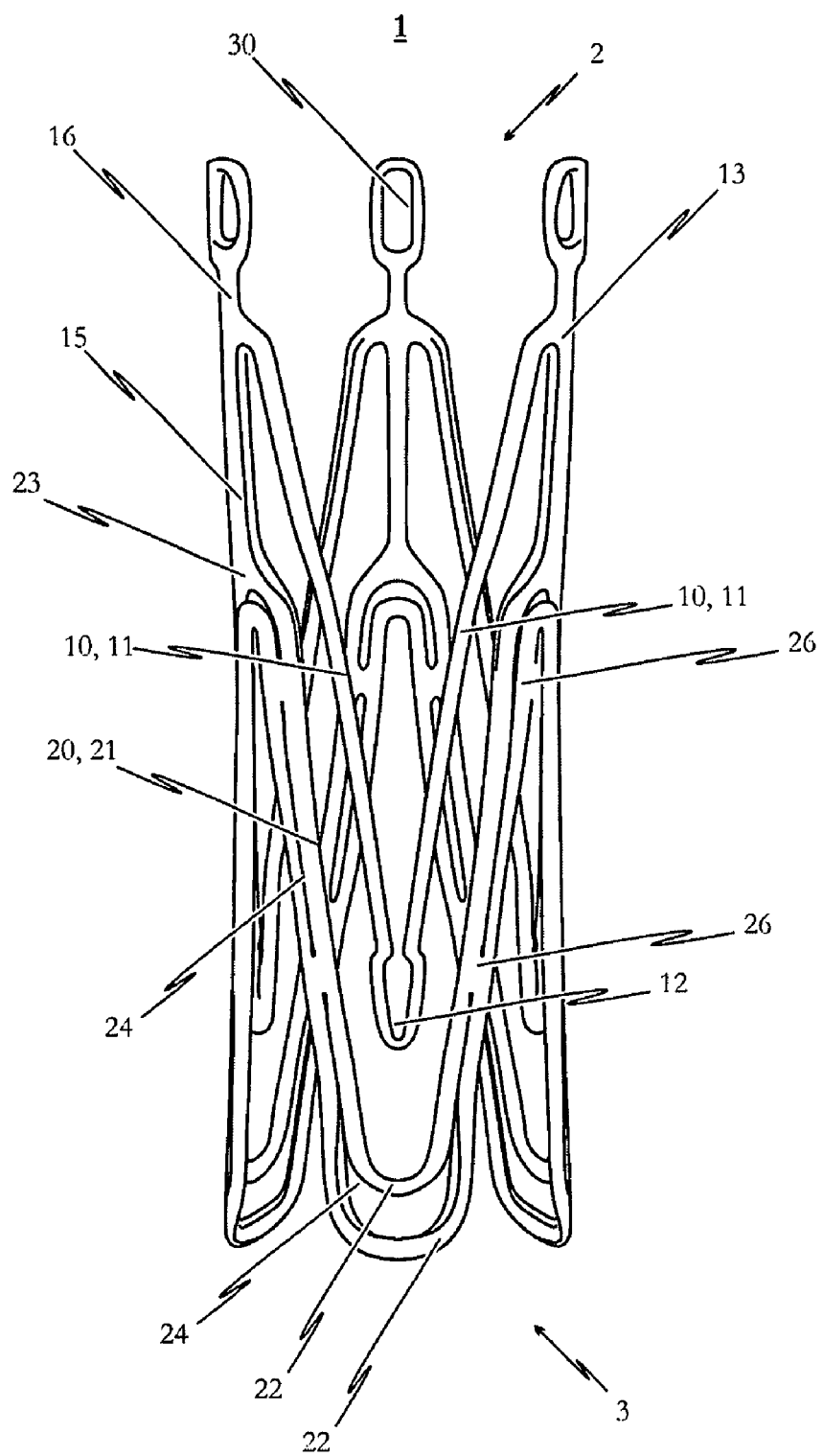
FIG. 6b shows the endoprosthesis illustrated in FIG. 6a in a state between its first, pre-definable mode and its second mode in which the medical device is in its expanded state.
Figure 6C:
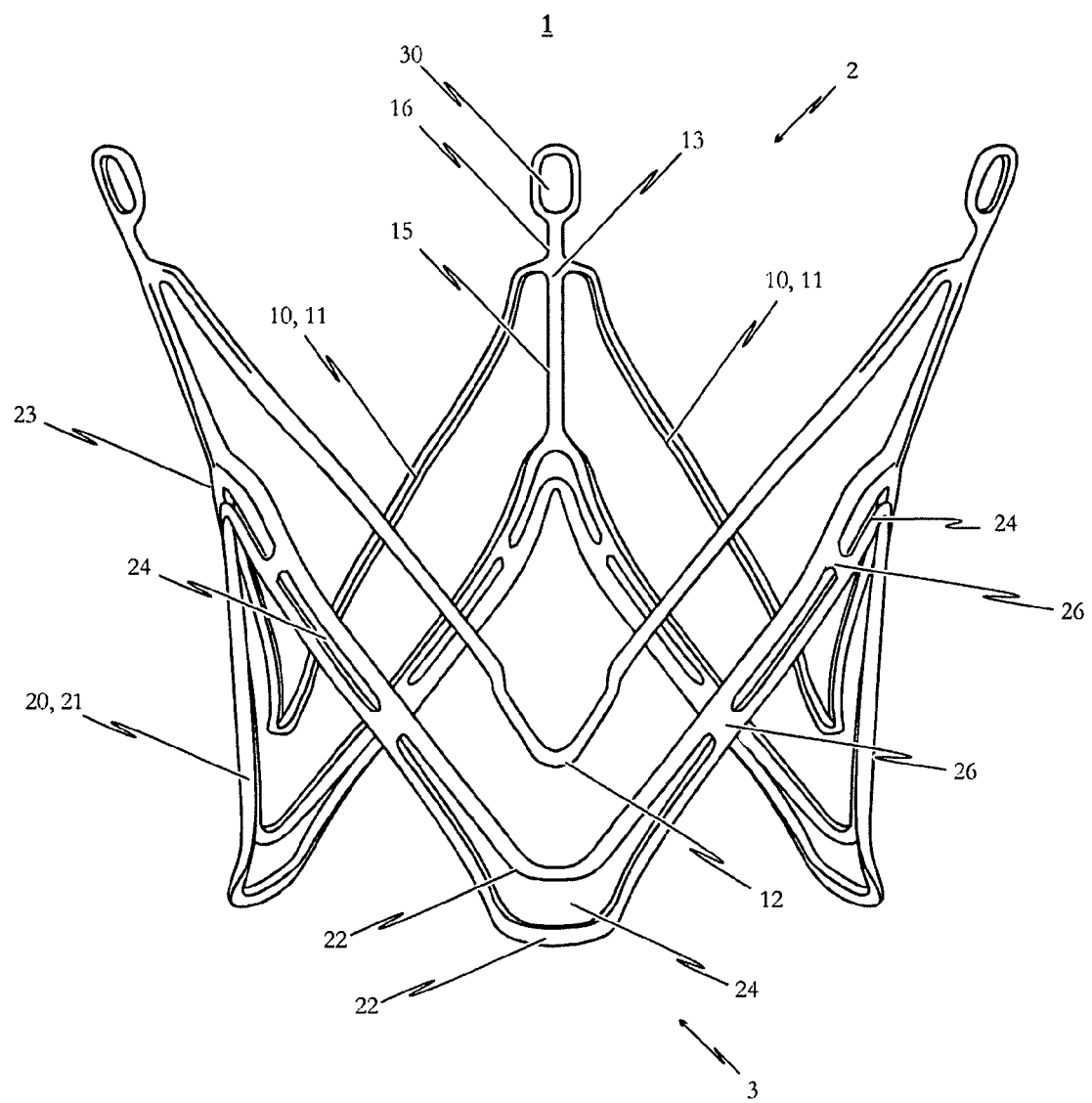
FIG. 6c shows the endoprosthesis illustrated in FIG. 6a in its second mode in which the medical device is in its expanded state.
Figure 6D:
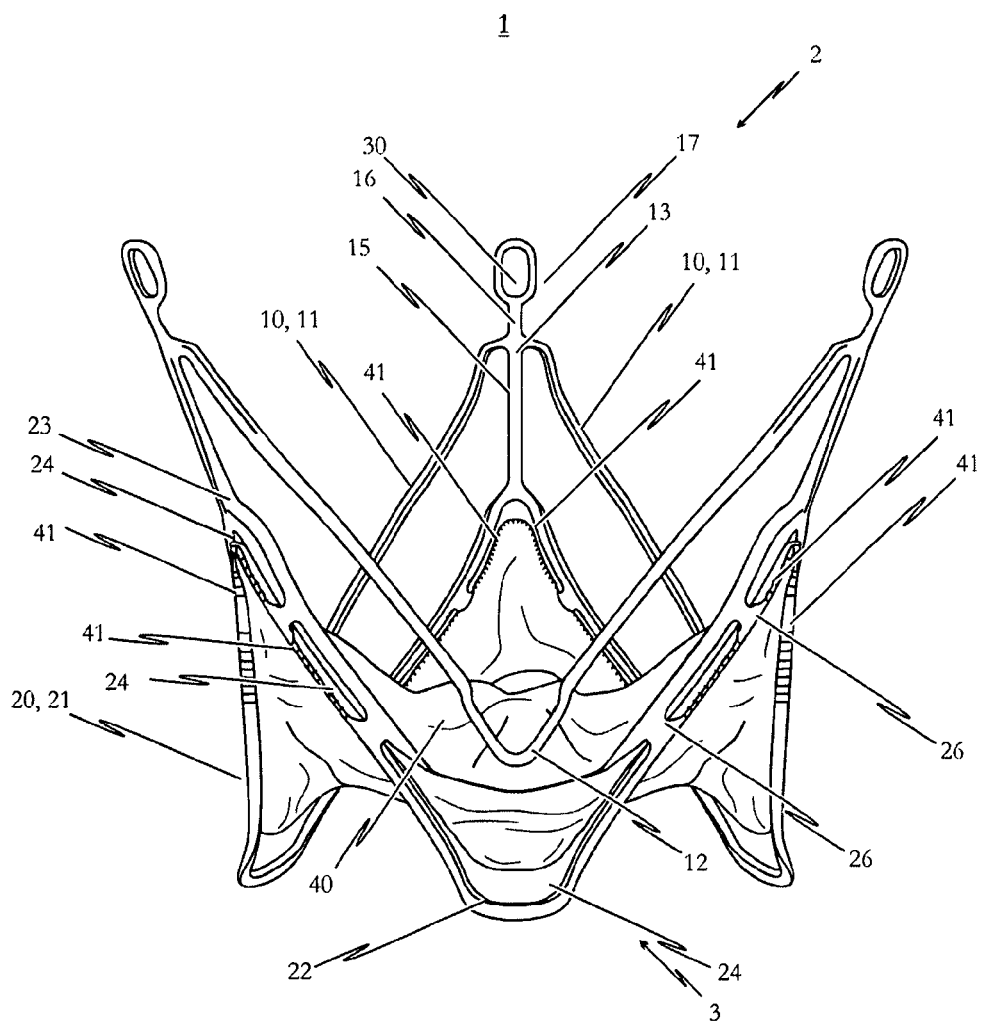
FIG. 6d illustrates a sixth preferred embodiment of the medical device proposed by the invention in its expanded state, with an endoprosthesis of the type illustrated in FIG. 6c and a heart valve prosthesis attached to it and opened out.
Figure 6E:
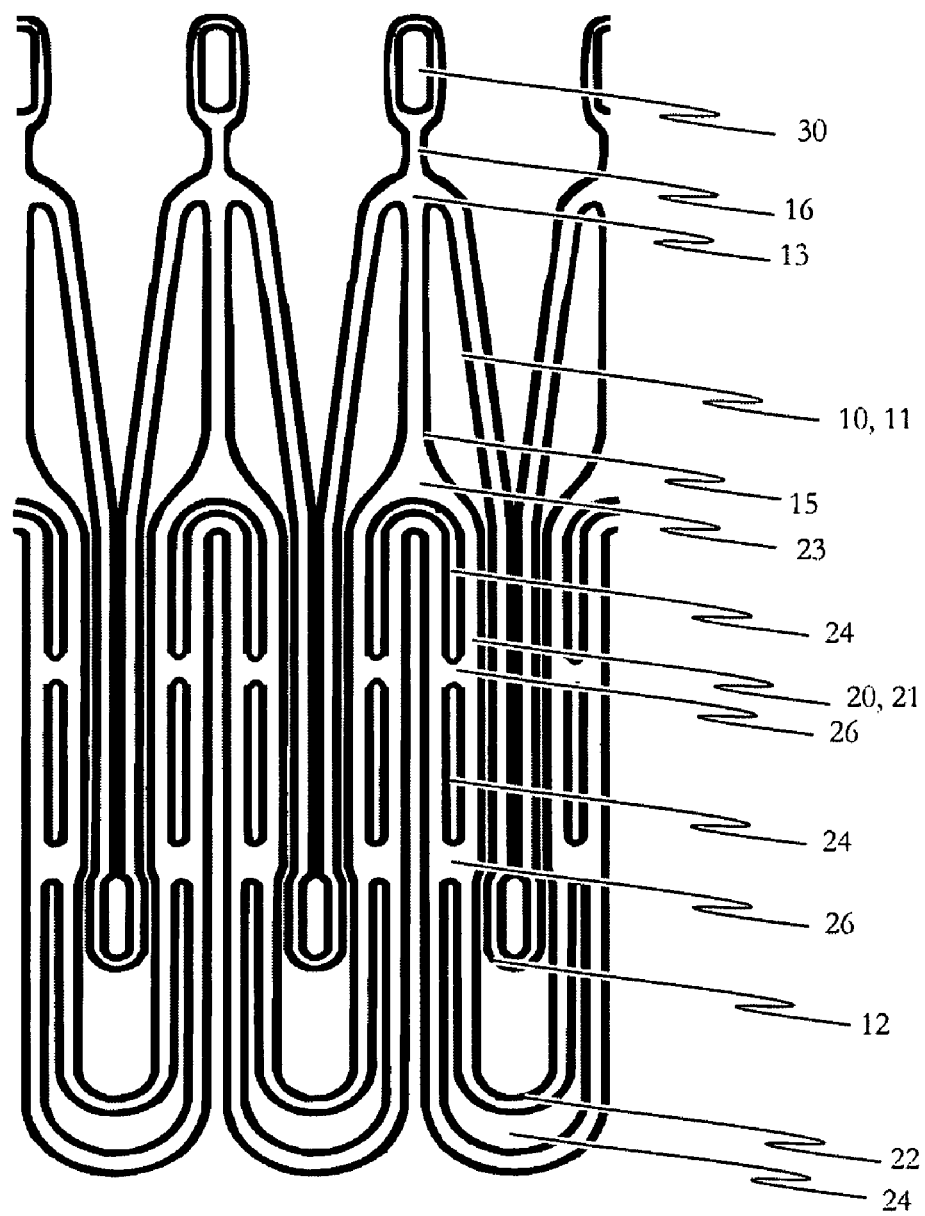
FIG. 6e is a flat projection of a cutting pattern which can be used for the production of the sixth, preferred, self-expandable endoprosthesis in order to cut the endoprosthesis illustrated in FIG. 6a integrally from a metal tube.
Figure 7A:
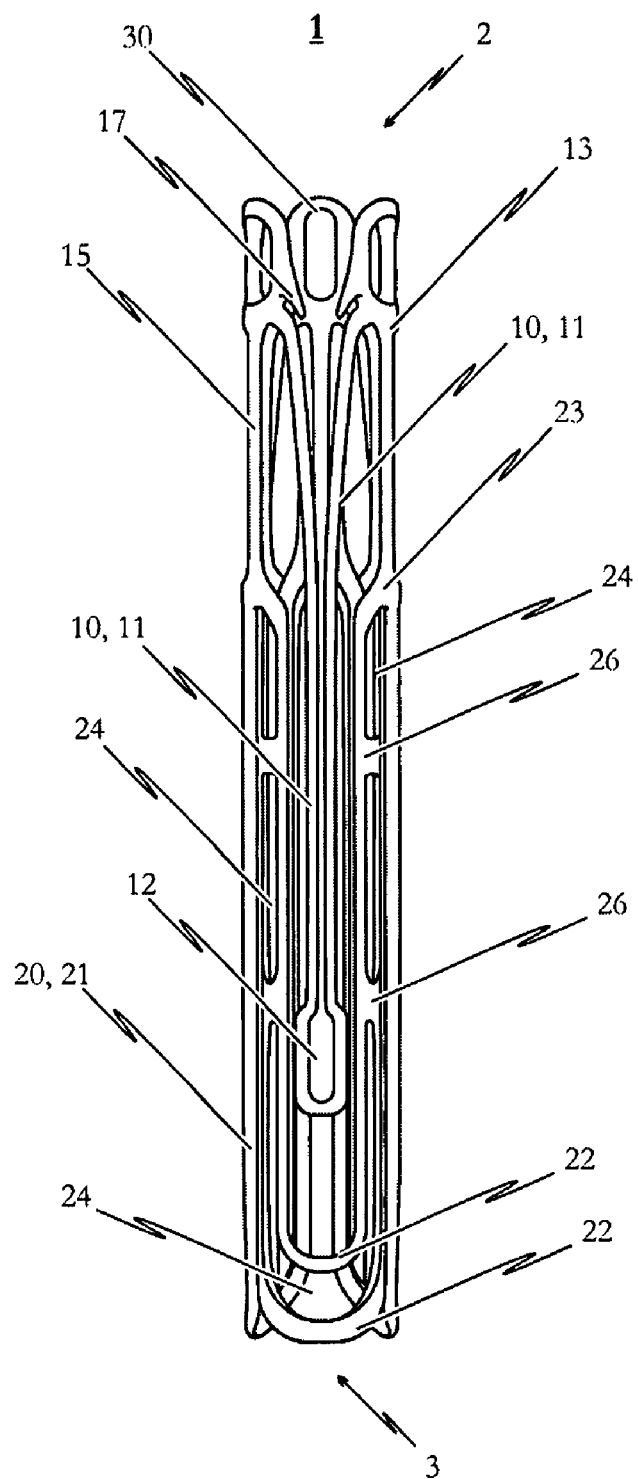
FIG. 7a shows a seventh, preferred embodiment of a self-expandable endoprosthesis for the medical device proposed by the invention in its first, pre-determined mode in which the medical device is in its collapsed state.
Figure 7B:
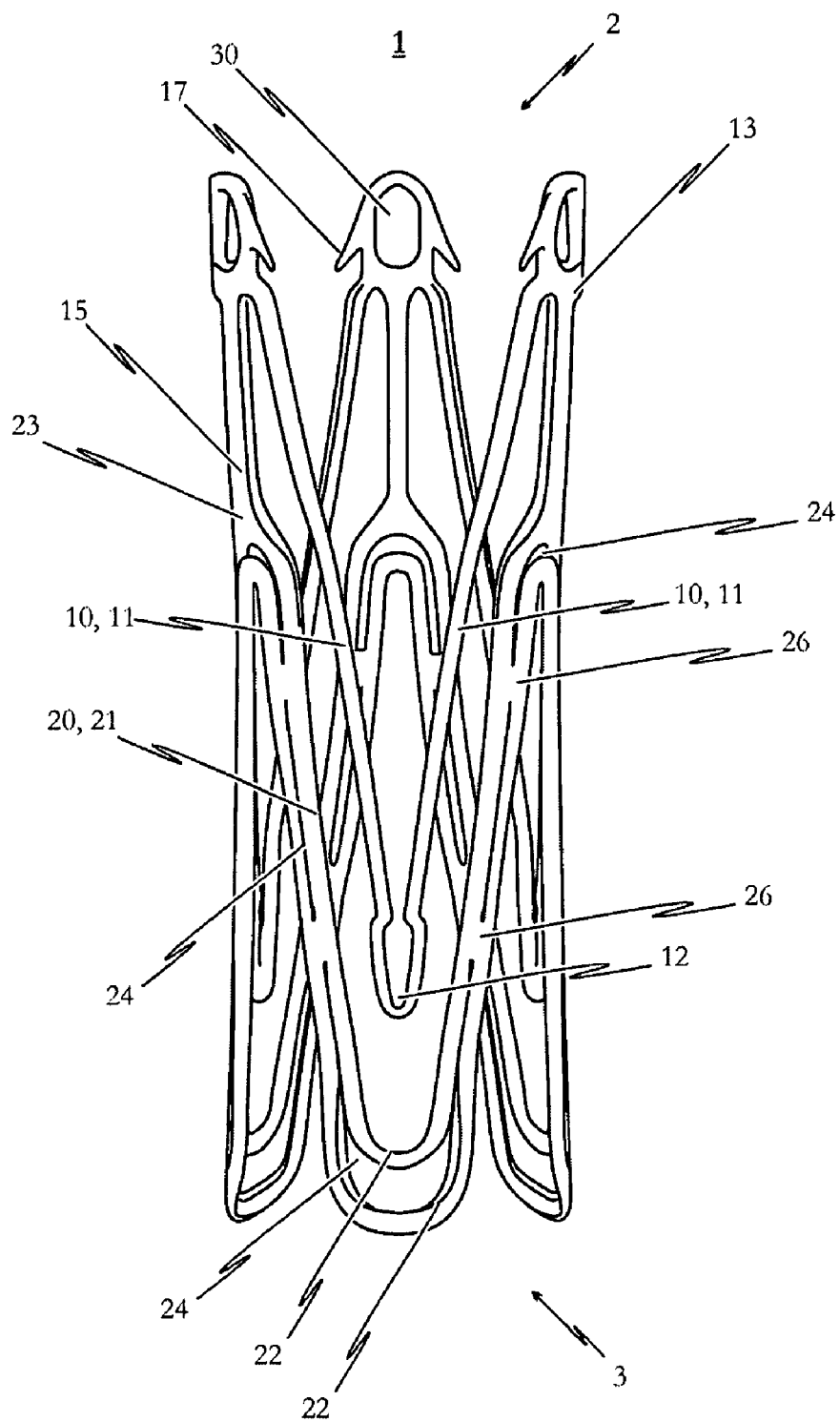
FIG. 7b shows the endoprosthesis illustrated in FIG. 7a in a state between its first, pre-definable mode and its second mode in which the medical device is in its expanded state.
Figure 7C:
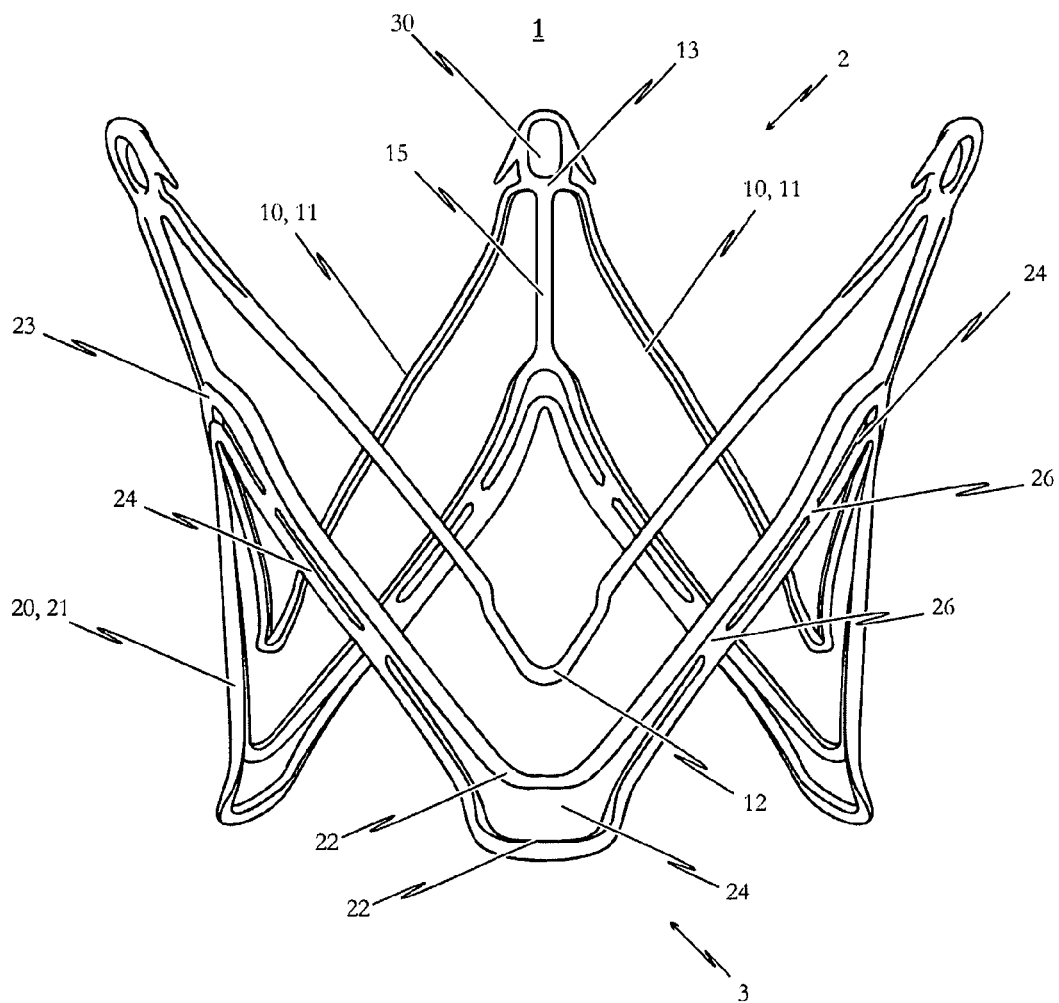
FIG. 7c shows the endoprosthesis illustrated in FIG. 7a in its second mode in which the medical device is in its expanded state.
Figure 7D:
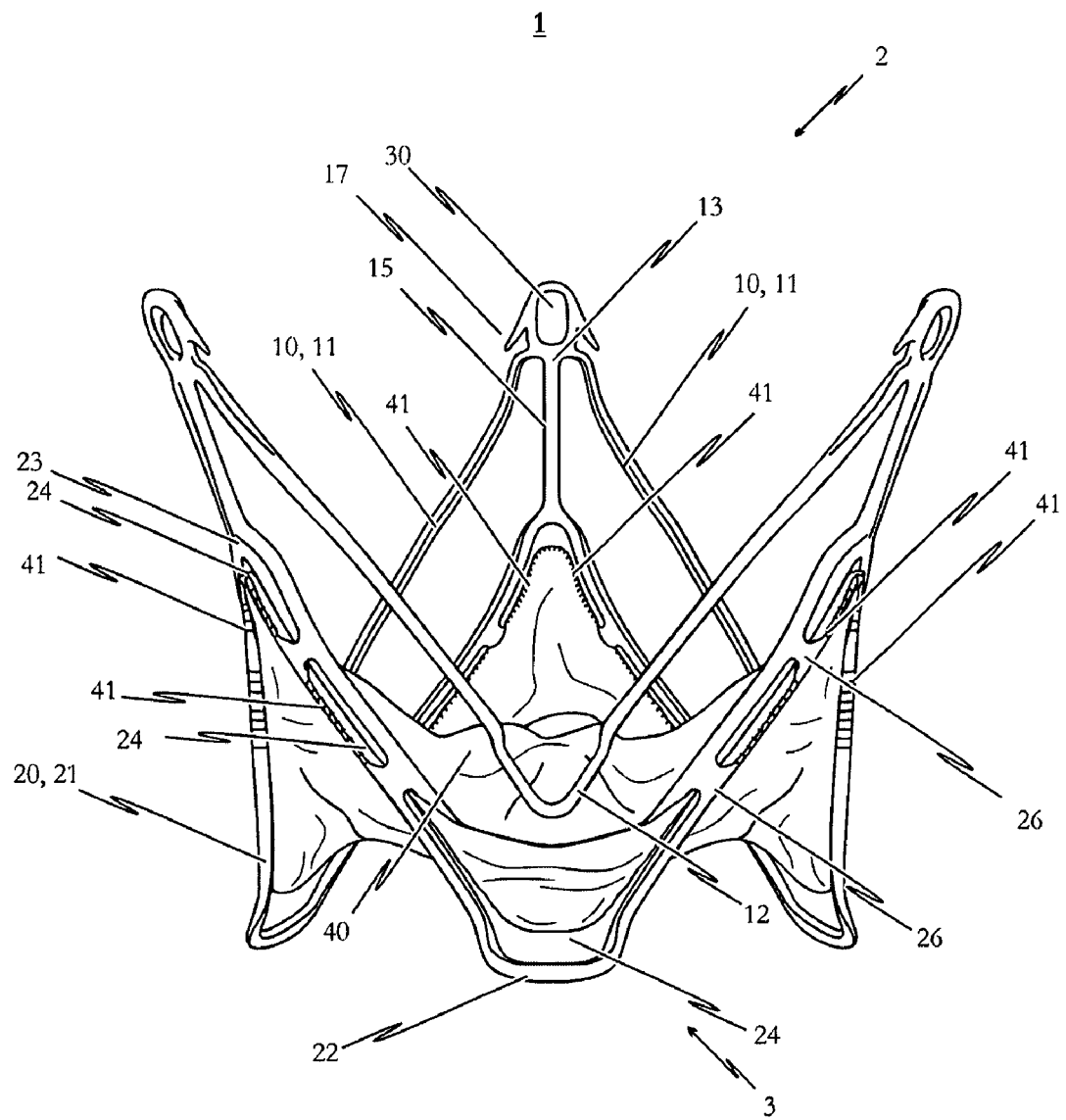
FIG. 7d illustrates a seventh preferred embodiment of the medical device proposed by the invention in its expanded state, with an endoprosthesis of the type illustrated in FIG. 7c and a heart valve prosthesis attached to it and opened out.
Figure 7E:
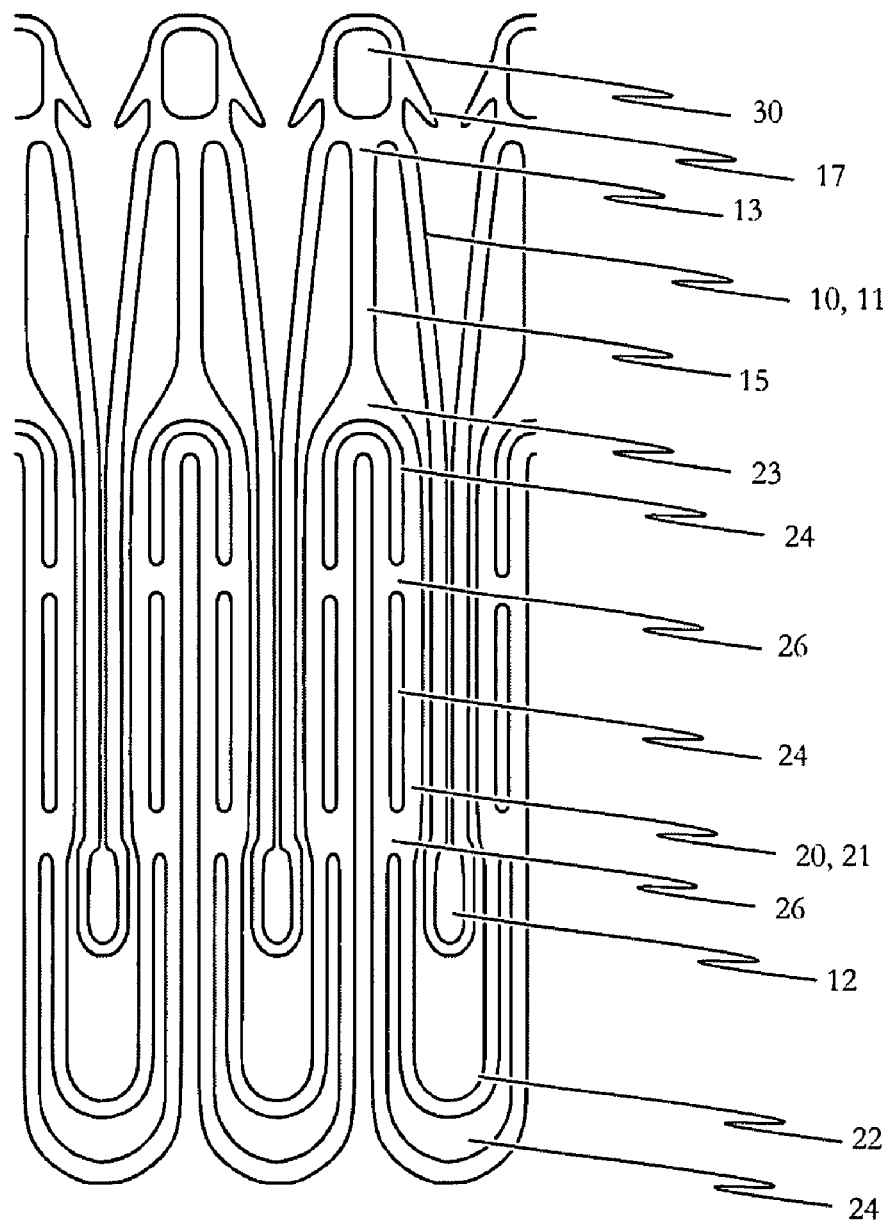
FIG. 7e is a flat projection of a cutting pattern which can be used for the production of the seventh preferred, self-expandable endoprosthesis in order to cut the endoprosthesis illustrated in FIG. 7a integrally from a metal tube.
Figure 8A:
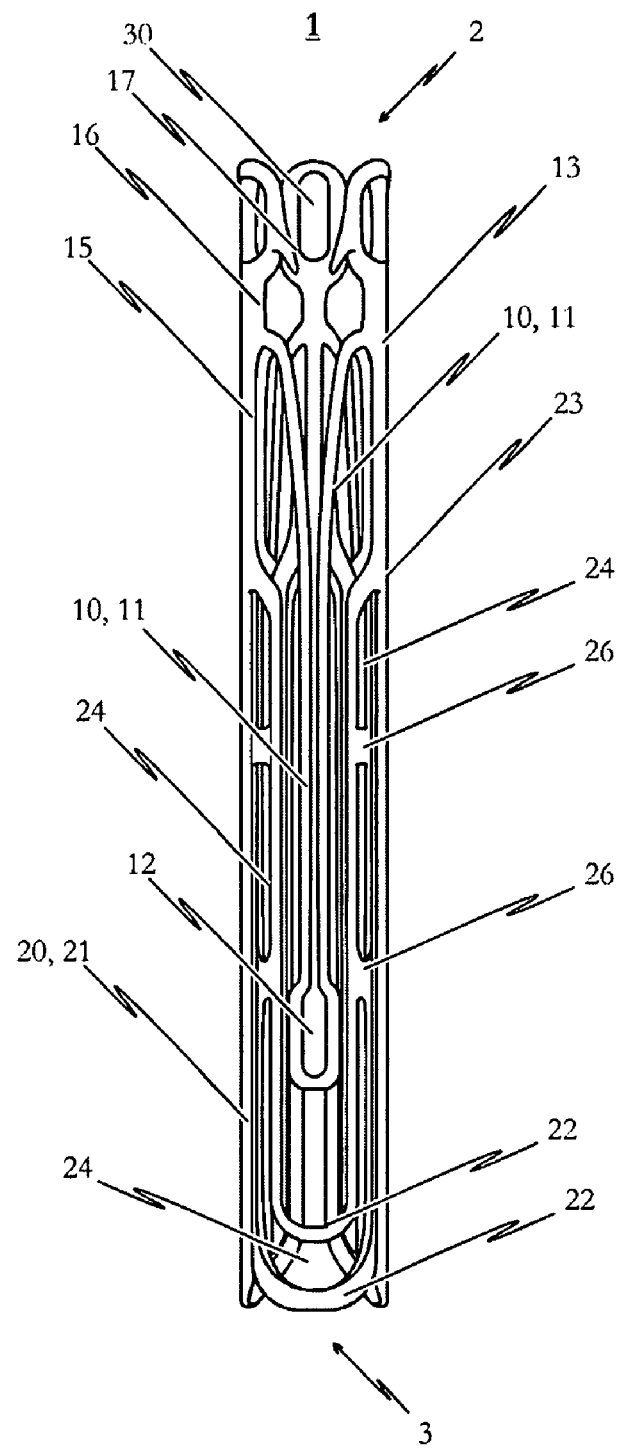
FIG. 8a shows an eighth, preferred embodiment of a self-expandable endoprosthesis for the medical device proposed by the invention in its first, pre-determined mode in which the medical device is in its collapsed state.
Figure 8B:
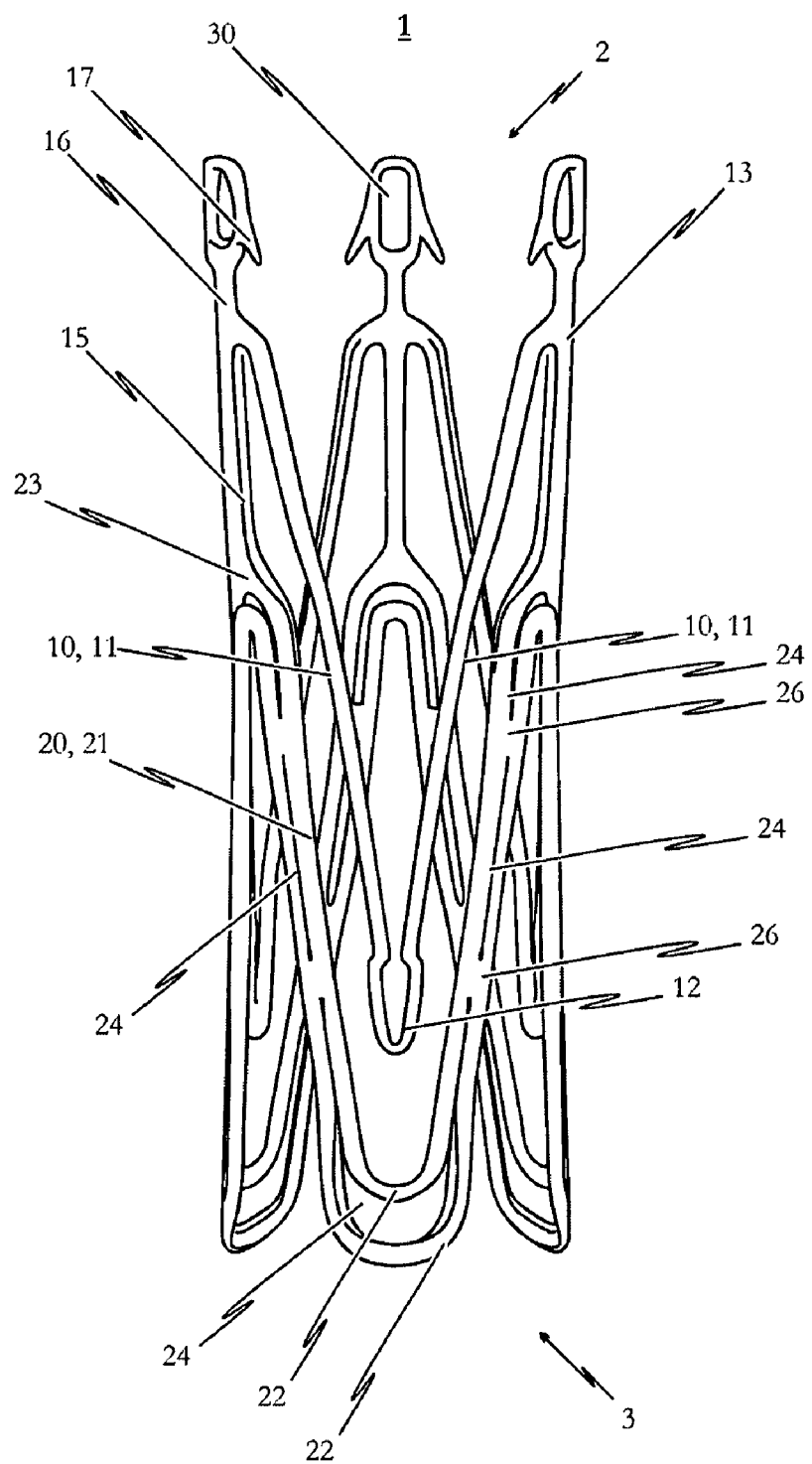
FIG. 8b shows the endoprosthesis illustrated in FIG. 8a in a state between its first, pre-definable mode and its second mode in which the medical device is in its expanded state.
Figure 8C:
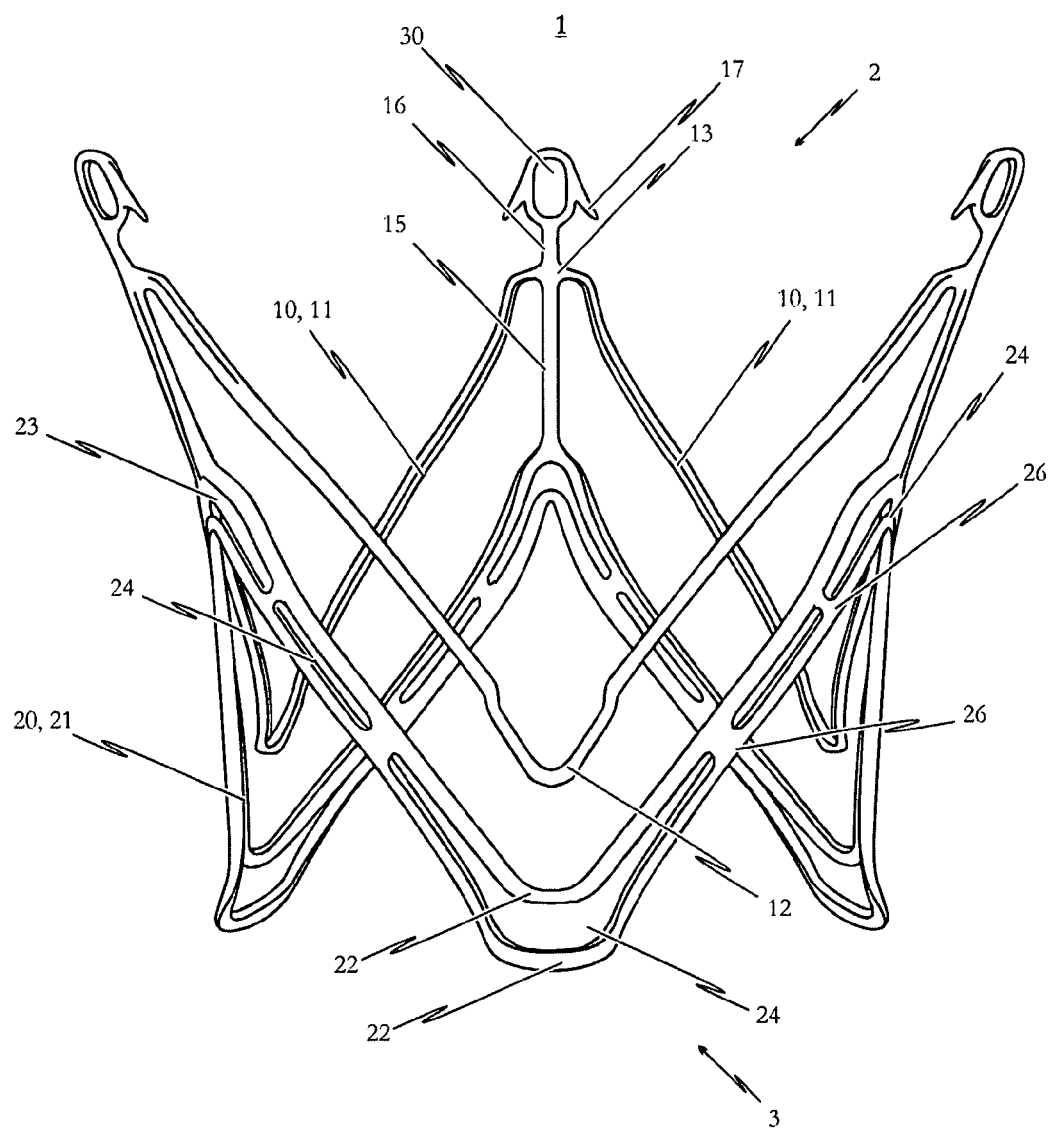
FIG. 8c shows the endoprosthesis illustrated in FIG. 8a in its second mode in which the medical device is in its expanded state.
Figure 8D:
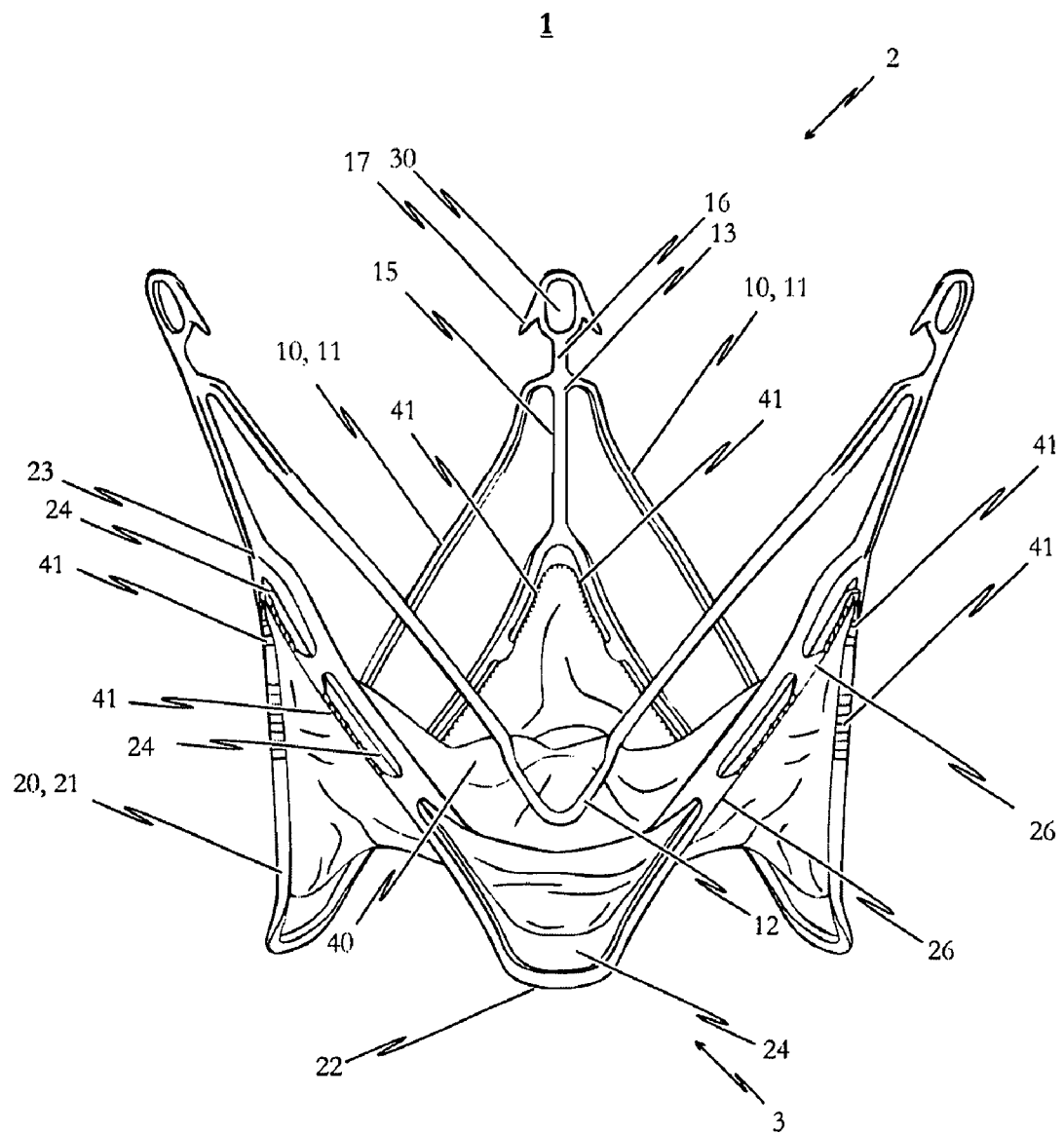
FIG. 8d illustrates an eighth preferred embodiment of the medical device proposed by the invention in its expanded state, with an endoprosthesis of the type illustrated in FIG. 8c and a heart valve prosthesis attached to it and opened out.
Figure 8E:
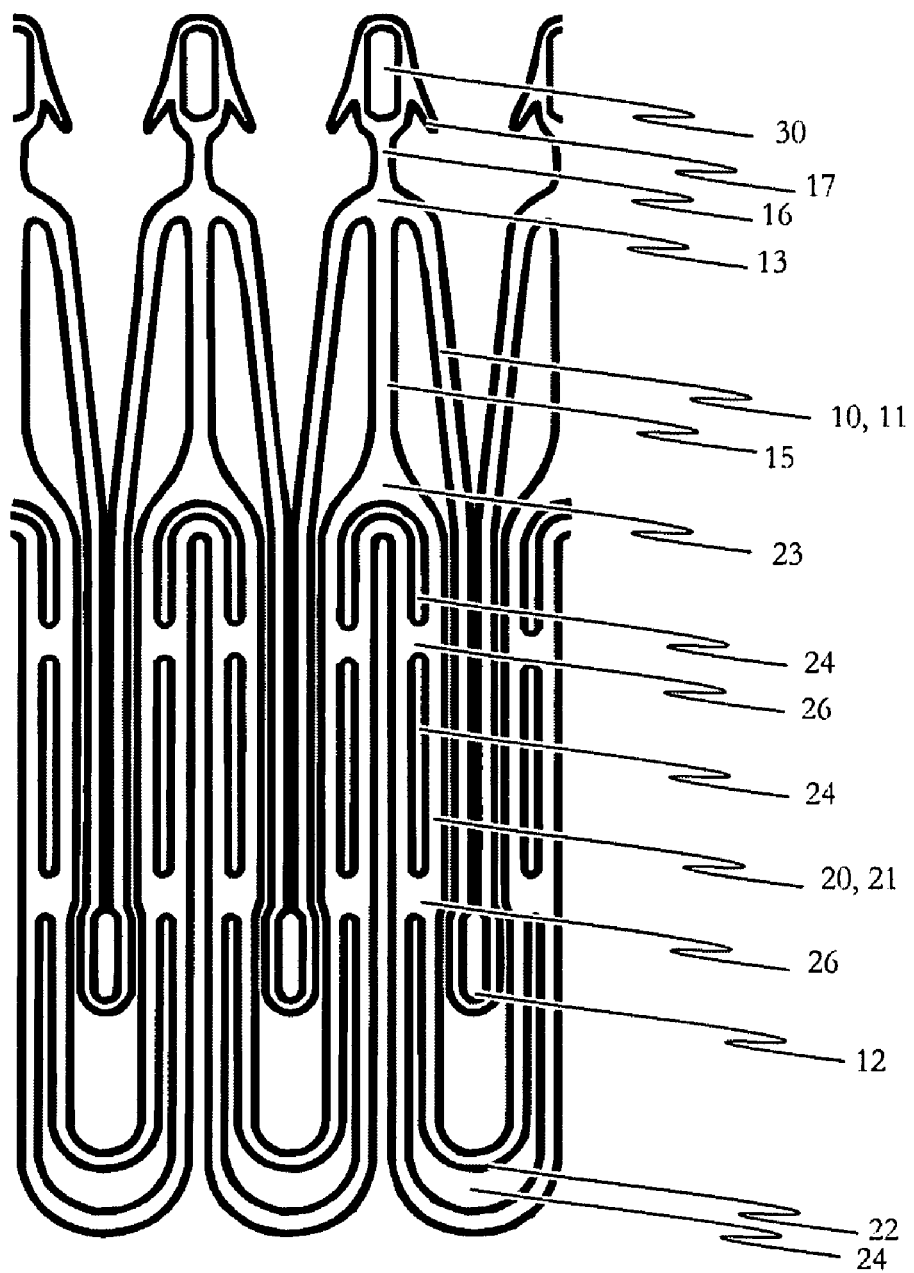
FIG. 8e is a flat projection of a cutting pattern which can be used for the production of the eighth preferred, self-expandable endoprosthesis in order to cut the endoprosthesis illustrated in FIG. 8a integrally from a metal tube.

FIG. 5e illustrates a flat projection of a cutting pattern which may be used for production of the fifth preferred embodiment of the self-expandable endoprosthesis 1 in order to cut the endoprosthesis 1 illustrated in FIG. 5a integrally from a metal tube.

The sixth preferred embodiment of the self-expandable endoprosthesis and the medical device proposed by the invention illustrated in FIGS. 6a to 6e corresponds to a combination of the second preferred embodiment illustrated in FIGS. 2a to 2e and the fifth preferred embodiment described above with reference to FIGS. 5a to 5e. Specifically, therefore, the endoprosthesis 1 based on the second preferred embodiment is provided with additional anchoring portions 26 at the respective retaining arches 21, which interrupt the slots 24 extending in the longitudinal direction of the retaining arches 21.

The seventh preferred embodiment of the endoprosthesis 1 and the medical device proposed by the invention illustrated in FIGS. 7a to 7e corresponds to a combination of the third and fifth embodiments described above, in which case the respective fixing eyes 30 are provided with barbs 17 and the respective retaining arches 21 are provided with reinforcing portions 26.

The eighth preferred embodiment of the self-expandable endoprosthesis and the medical device proposed by the invention illustrated in FIGS. 8a to 8e corresponds to a combination of the fourth and fifth embodiments, in which case the respective retaining arches 21 are provided with reinforcing portions 26 and the fixing eyes 30 provided with barbs 17 are connected to the respective arms 11 of the adjacent positioning arches 10 by means of a connecting web 16 extending essentially in the longitudinal direction of the endoprosthesis 1.

Figure 9A:
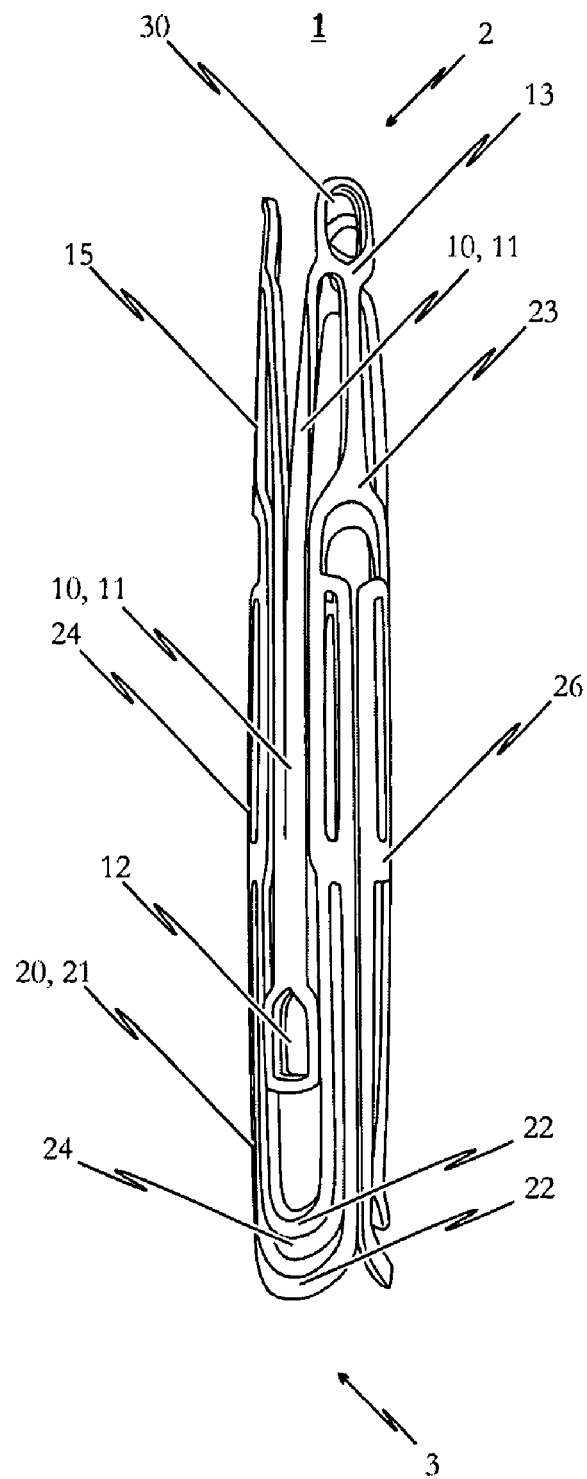
FIG. 9a shows a ninth, preferred embodiment of a self-expandable endoprosthesis for the medical device proposed by the invention in its first, pre-determined mode in which the medical device is in its collapsed state.
Figure 9B:
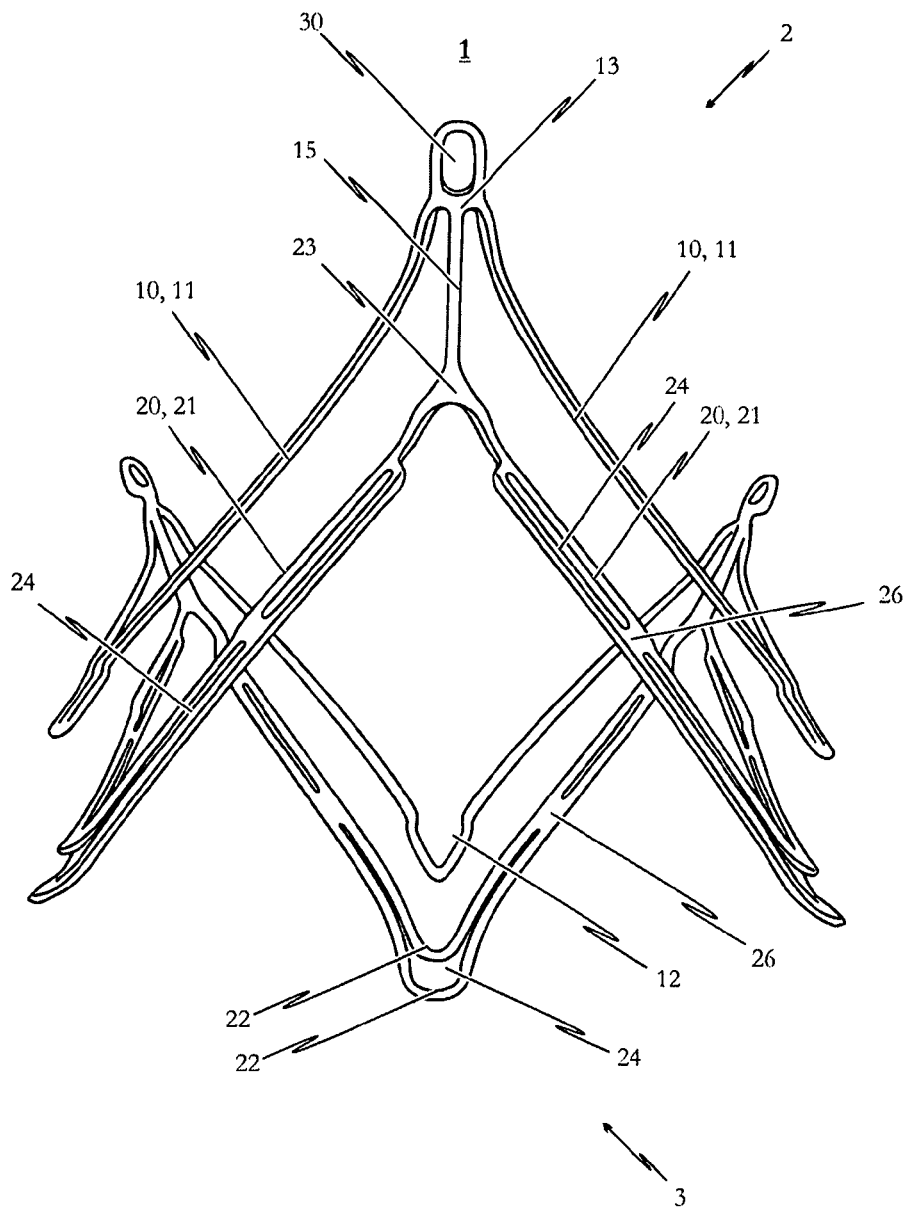
FIG. 9b is a perspective side view of a connecting web between an end portion of a positioning arch and an end portion of an associated retaining arch of the endoprosthesis illustrated in FIG. 9a in its second mode in which the medical device is in its expanded state.
Figure 9C:
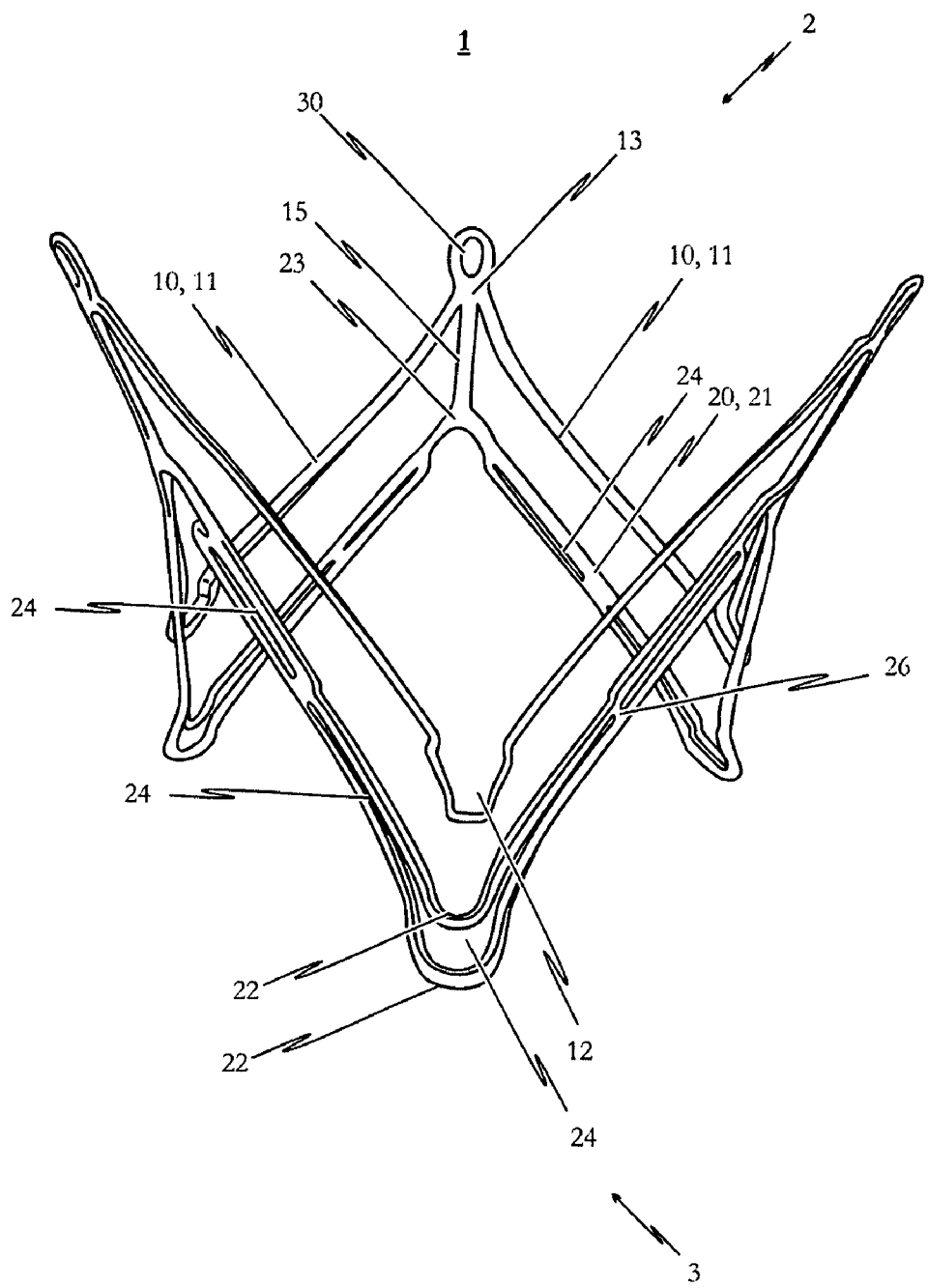
FIG. 9c is a perspective side view of a positioning arch and the associated retaining arch of the endoprosthesis illustrated in FIG. 9a in its second mode in which the medical device is in its expanded state.
Figure 9D:
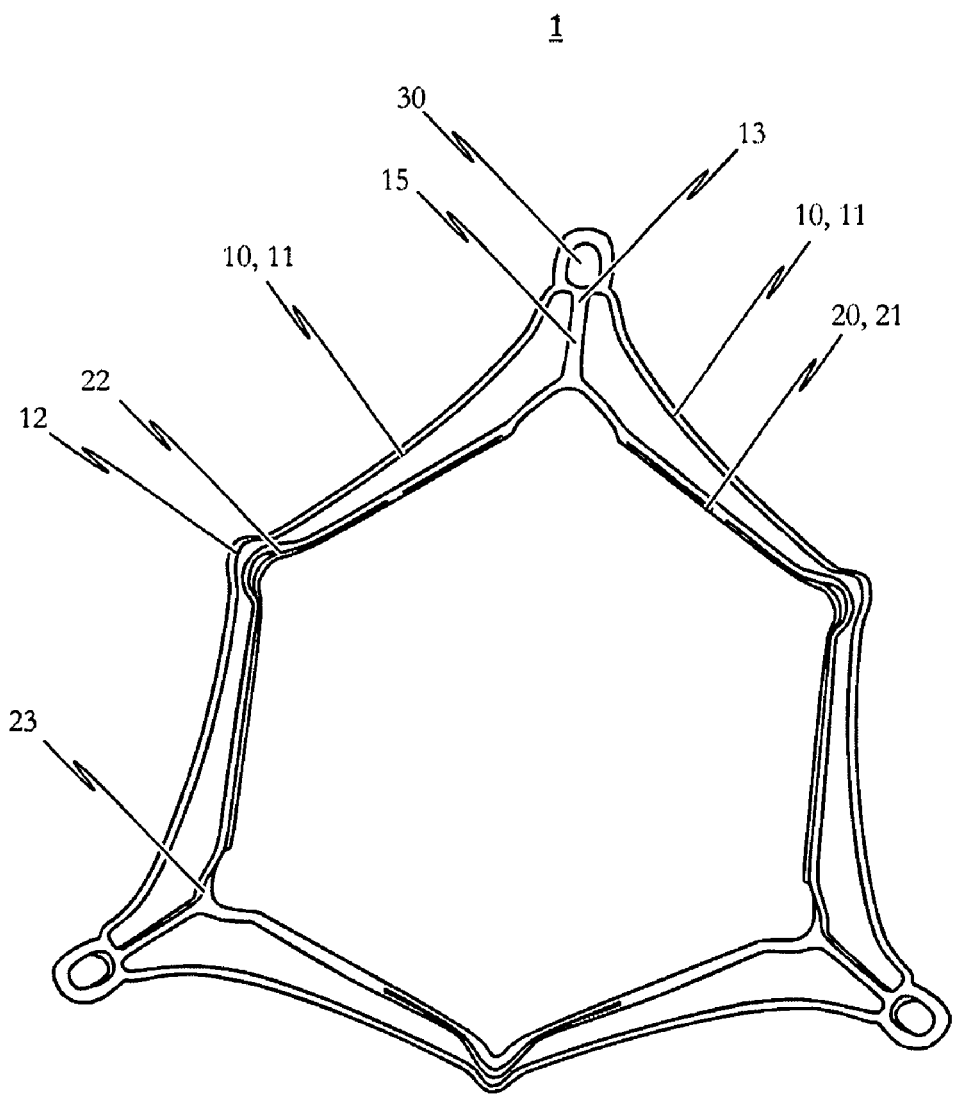
FIG. 9d is a perspective plan view of the distal region of the endoprosthesis illustrated in FIG. 9a in its second mode in which the medical device is in its expanded state.

The ninth preferred embodiment of the self-expandable endoprosthesis for the medical device proposed by the invention illustrated in FIGS. 9a to 9d is of a slightly modified shape compared with the first embodiment (see FIGS. 1a to 1c). The endoprosthesis 1 based on the ninth embodiment is illustrated in its first pre-defined mode in FIG. 9a. FIGS. 9b and 9c respectively show a perspective side view of the endoprosthesis 1 based on the ninth embodiment in its second mode. Specifically, the connecting web 15 between the end portion 13 of a positioning arch 10, 11 and the end portion 23 of an associated retaining arch 20, 21 is illustrated in FIG. 9b. FIG. 9c, on the other hand, illustrates the positioning arches 10, 11 and the associated retaining arches 20, 21 of the endoprosthesis 1 illustrated in FIG. 9a.

Figure 9E:
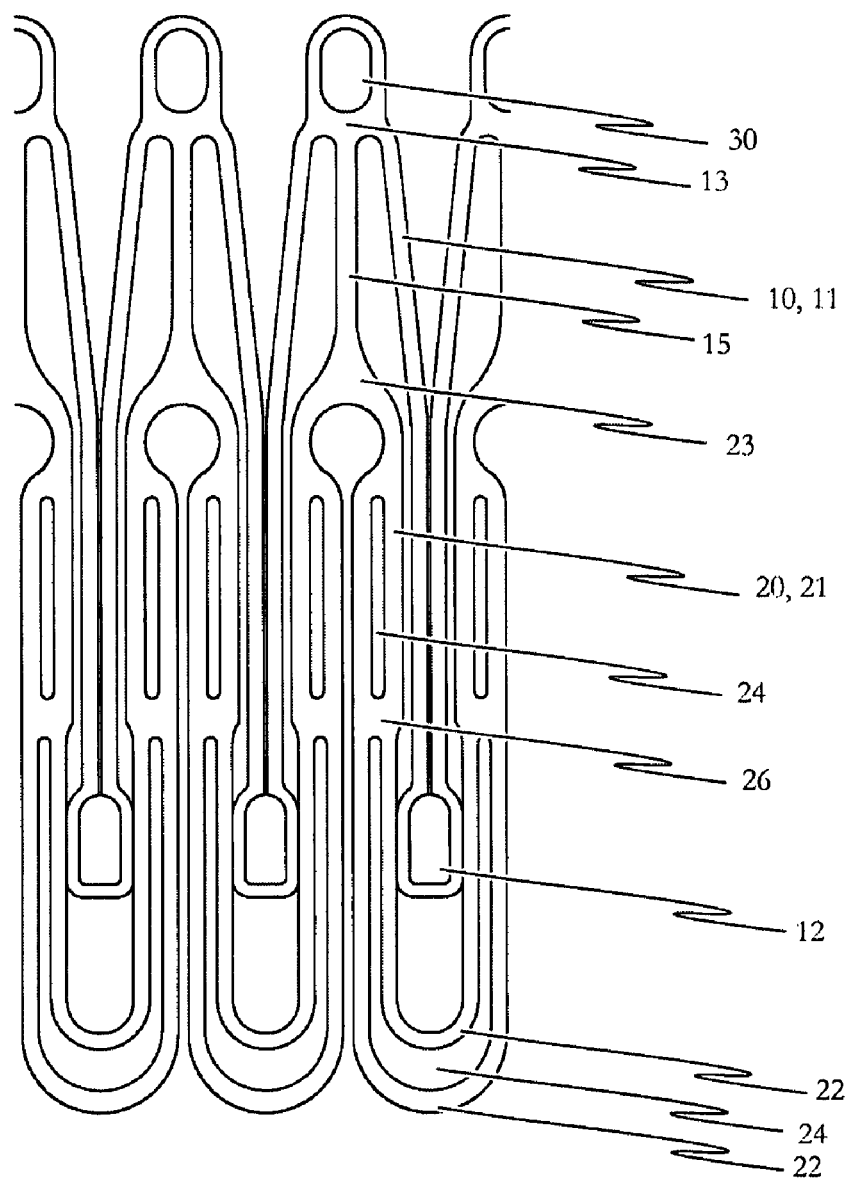
FIG. 9e is a flat projection of a cutting pattern which can be used for the production of the ninth preferred embodiment of the self-expandable endoprosthesis in order to cut the endoprosthesis illustrated in FIG. 9a integrally from a metal tube.

FIG. 9e illustrates a flat projection of a cutting pattern which may be used to produce the ninth preferred embodiment of the self-expandable endoprosthesis in order to cut the endoprosthesis illustrated in FIG. 9a integrally from a metal tube.

Unlike the first embodiment, the respective head portions 12 of the positioning arches 10 pointing towards the proximal end 3 of the endoprosthesis are of a slightly wider design at the proximal end in the ninth embodiment of the endoprosthesis 1. Although the head portions 12 of the positioning arches 10 have a slightly rectangular in shape compared with the first embodiment, all the respective corners of the head portions 12 are rounded so that the vessel wall is not damaged when the positioning arches 10 engage in the pockets of the heart valve to be replaced. The advantage of the slightly wider design of the head portions 12 of the positioning arches 10 is that the positioning arches 10 can be placed in the pockets of the native heart valve with the smallest possible clearance during the implantation operation, thereby enabling even more accurate positioning of the medical device at the implantation site.

As with the embodiments described above, a total of two positioning webs or arms 11 extend from the head portion 12 of the positioning arches 10 to the distal end 2 of the endoprosthesis 1 for every positioning arch 10 in the ninth embodiment of the endoprosthesis 1, which merge at the distal end 2 of the endoprosthesis 1 into an eye-shaped element 30. This eye-shaped element 30 serves as a fixing means for attaching the endoprosthesis 1 and hence the medical device to an introduction catheter system.

Specifically in the case of the ninth embodiment of the endoprosthesis 1, the respective fixing eyes 30 are disposed between the two arms 11 of two mutually adjacent positioning arches 10. The connecting web 15 extending essentially in the longitudinal direction of the endoprosthesis 1 opens into the transition portion 13 between the two arms 11 of two mutually adjacent positioning arches 10 where the fixing eye 30 is formed. At the proximal end of the connecting web 15, the latter merges into the respective retaining arms 21 of two mutually adjacent retaining arches 20. This design is illustrated particularly clearly in FIG. 9*d*, which shows a perspective plan view of the distal region of the endoprosthesis illustrated in FIG. 9*a* in its second mode.

By contrast with the embodiments described above, the respective retaining arms 21 of the retaining arches 20 on the transition portion 23 between the two arms 21 of two mutually adjacent retaining arches 20 are not provided with slots or elongate holes 24 in the ninth embodiment of the endoprosthesis 1. Due to the fact that only one arm web 21 actually opens into the transition portion 23 between the two arms 21 of two mutually adjacent retaining arches 20 for each retaining arch, there are advantageously no components belonging to the retaining arches 20 which project out from the respective retaining arches 20 in the radial direction when the endoprosthesis 1 is in the expanded state (see FIG. 9*b* for example). Especially when the endoprosthesis 1 is in the expanded state, no barb portion such as usually extends through the slots 24 projects out in the radial direction at the transition portions 23 between the two arms 21 of two mutually adjacent retaining arches 20, the tip of which points in the direction of the distal retaining region 2 of the endoprosthesis 1. Due to the fact that a barb portion of this type is dispensed with in the ninth embodiment, the endoprosthesis 1 can be explanted particularly easily and removed from the patient's body again.

Although the ninth embodiment of the endoprosthesis 1 does not have slots or elongate holes 24 at the respective transition portions 23 between the two arms 21 of two mutually adjacent retaining arches 20, the respective retaining arms 21 of the endoprosthesis 1 have reinforcing portions 26, which are respectively provided on portions of the retaining arms 21 that are not congruent with the transition portions 23 between the two arms 21 of two mutually adjacent retaining arches 20.

Figure 10:
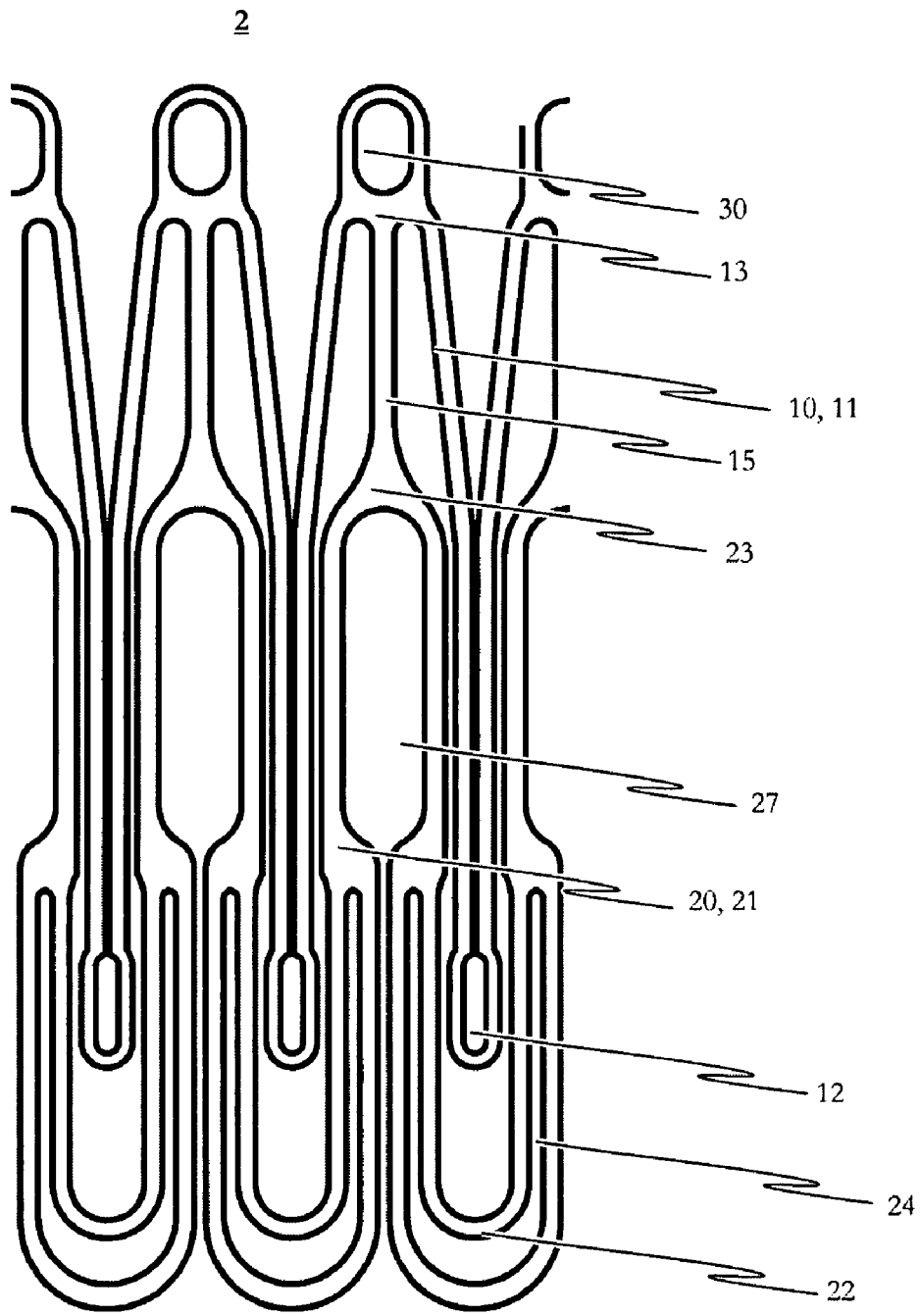
FIG. 10 is a flat projection of a cutting pattern which can be used for the production of another preferred embodiment of the self-expandable endoprosthesis in order to cut an endoprosthesis integrally from a metal tube.

FIG. 10 illustrates a flat projection of a cutting pattern, which may be used for the production of another preferred embodiment of the self-expandable endoprosthesis 1 in order to cut an endoprosthesis integrally from a metal tube. The cutting pattern illustrated in FIG. 9 differs from the cutting pattern illustrated in FIG. 1*e* due to the fact that the distally disposed slots 24 extending in the longitudinal direction of the retaining arches 21 have been omitted from the respective retaining arches 21 on the one hand, and a bigger space 27 is cut from between the adjacent retaining arches 21 in order to save on material on the other hand.

Figure 11:
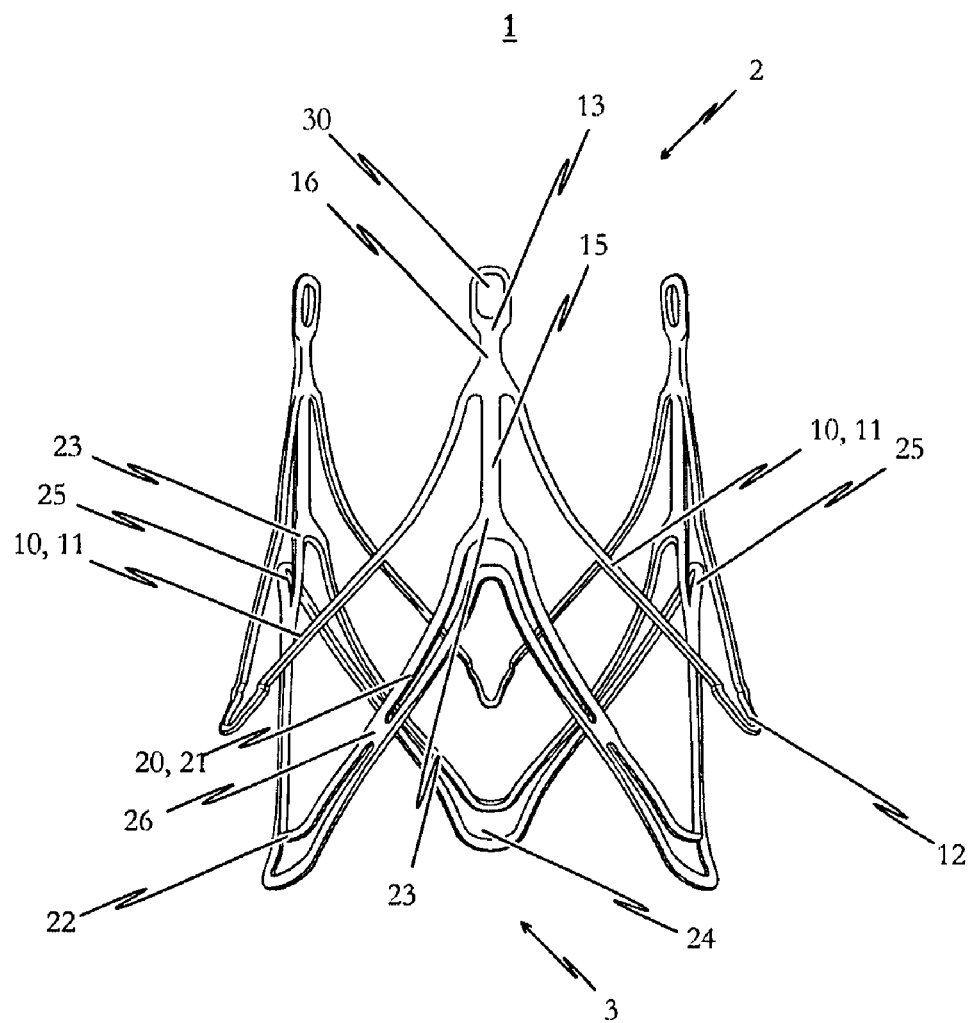
FIG. 11 shows another preferred embodiment of a self-expandable endoprosthesis for the medical device proposed by the invention in its second mode in which the medical device is in its expanded state.

FIG. 11 illustrates another preferred embodiment of a self-expandable endoprosthesis 1 for an alternative design of the medical device proposed by the invention. Specifically, the endoprosthesis 1 of the other preferred embodiment illustrated in FIG. 11 has assumed its second mode in which the medical device is in its expanded state and contains a different embodiment of the endoprosthesis 1 for the medical device proposed by the invention. Specifically, this is an endoprosthesis 1 which is in its second mode, i.e. after triggering the shape memory effect.

The endoprosthesis 1 illustrated in FIG. 11 differs from the endoprosthesis 1 illustrated in FIG. 1*c* due to the fact that in the case of the stent 1 illustrated in FIG. 11, an interconnecting web 16 extending essentially in the longitudinal direction of the endoprosthesis 1 is provided between the fixing eyes 30 and the transition portion 13 between the positioning arms 11 of two adjacent positioning arches 10, and the total length of the endoprosthesis 1 and hence the medical device is made longer. In order to ensure optimum ability to manoeuvre the medical device in the collapsed state, however, it is of advantage if the endoprosthesis 1 has as short a longitudinal extension as possible, especially if the implantation route to the heart valve leads through the arch of the aorta, in which case it is of advantage if the medical device is as short as possible (and the endoprosthesis 1 is also as short as possible) so that it can overcome this bend.

The endoprosthesis 1 illustrated in FIG. 11 also differs from the endoprosthesis of the embodiments described above due to the fact that when the endoprosthesis 1 is in the expanded state, a barb portion 25 projects through the slots 24 in the radial direction at the respective transition portions 23 between the two arms 21 of two mutually adjacent retaining arches 20, the tip of which points in the direction of the distal retaining region 2 of the endoprosthesis 1.

A more detailed description will be given below with reference to FIGS. 12*a* and 12*b*, explaining how the medical device proposed by the invention is used to treat a condition of heart valve insufficiency.

The medical device proposed by the invention, and in particular the endoprosthesis 1 with the heart valve prosthesis 40 contained in it, is designed to be introduced into the patient's body either backwards or transapically, i.e. coming from the heart apex, via a special catheter, positioned percutaneously orthotopically in vivo and assume the function of an insufficient or narrowed heart valve. FIG. 12*a* provides a schematic illustration of one possible implantation operation for the medical device proposed by the invention, whereby the medical device in this instance is introduced into the patient's body backwards using a special catheter. FIG. 12*b* provides a schematic view of the medical device proposed by the invention in the implanted state.

Figure 12A:
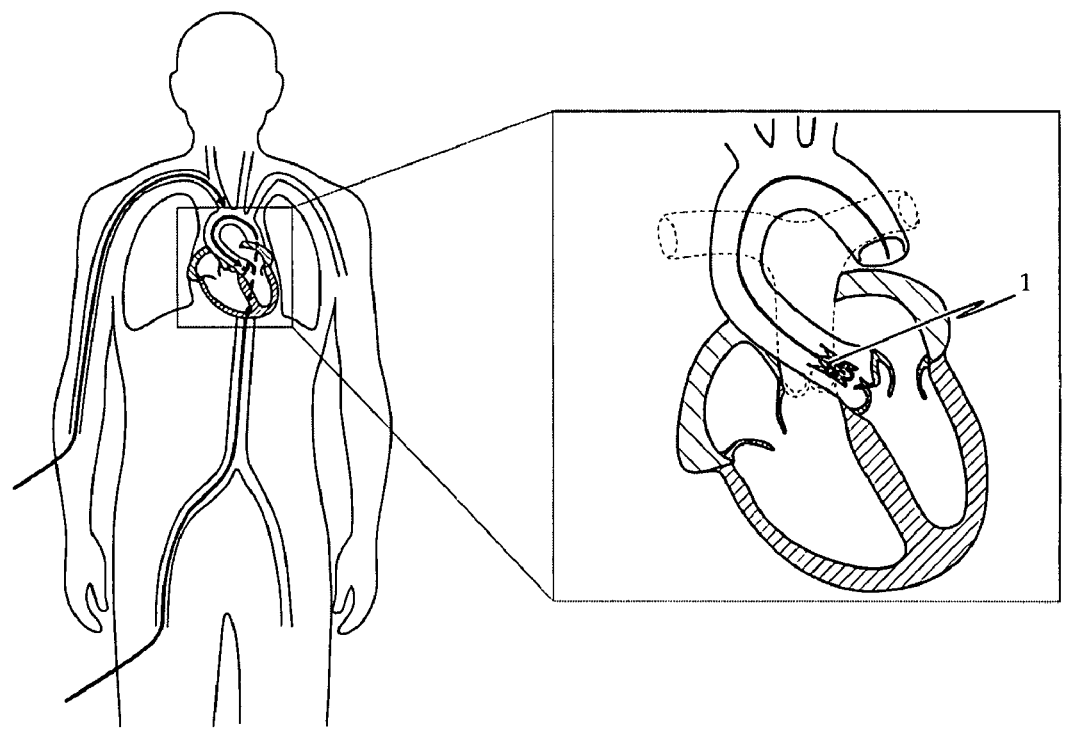
FIG. 12a is a schematic view intended to illustrate one possible implantation operation of the medical device proposed by this invention.

In the case of the implantation route illustrated in FIG. 12*a*, the special catheter system, which is not specifically illustrated, containing the medical device with the heart valve prosthesis 40 and the endoprosthesis 1 serving as an anchoring stent are introduced by puncturing the A. femoris communis (inguinal artery). This catheter system is preferably moved forward to the aortal valve position assisted by angiographic (vessel display) and echocardiographic (ultrasound) control, where the actual heart valve implantation then takes place.

Alternatively, a special catheter system can be pushed transapically from the heart apex through the left ventricle to the aortal valve, where a similar implantation of the endoprosthesis 1 with the heart valve prosthesis 40 is possible using a catheter tube modified accordingly.

As the special catheter system is being fed forwards, the medical device is preferably appropriately cooled, for example by rinsing the special catheter system with an appropriate coolant, such as a salt solution. When the medical device has been moved forward to the desired implantation site, cooling is interrupted, as a result of which the endoprosthesis 1 of the medical device is warmed to the body temperature (36° C.) of the patient, thereby triggering the shape memory effect of the endoprosthesis material.

Due to the triggering of the self-expanding property of the endoprosthesis 1, radial forces develop which act on the individual components of the endoprosthesis 1 and in particular on the respective positioning arches 10, 11 and retaining arches 20, 21 of the endoprosthesis 1. Since the endoprosthesis 1 of the medical device is still disposed in the introduction catheter system as before, the radial forces which develop once the critical switching temperature is exceeded and act on the individual components of the endoprosthesis 1 are still compensated by the introduction port of the introduction catheter system so that—in spite of the shape memory effect having been triggered—the endoprosthesis 1 of the medical device is forcibly held in its first (collapsed) shape.

By releasing the endoprosthesis 1 from the introduction catheter system in appropriate steps, the positioning arches 10, 11 of the endoprosthesis 1 are then moved out though the introduction port of the introduction catheter system. The positioning arches 10, 11 open out due to the radial forces acting in the radial direction. The opened positioning arches 10, 11 are then positioned in the pockets 50 of the native heart valve 51.

The other components of the endoprosthesis 1 and the medical device are then released through the introduction port of the introduction catheter system. As illustrated in FIG. 12*b*, the retaining arches 20, 21 open in the radial direction at the same time and thus cause the heart valve prosthesis 40 attached to the to the retaining arches 20, 21 by means of a thread 41, etc., for example, top open out in the manner of an umbrella. However, the radial forces acting on the retaining arches 20, 21 also act on the distal retaining region 2 of the endoprosthesis 1, causing the endoprosthesis 1 to be pressed in the radial direction against the vessel wall, which on the one hand guarantees a reliable anchoring of the medical device at the implantation site and on the other hand ensures a reliable seal of the heart valve prosthesis 40 at the proximal retaining region 3 of the endoprosthesis 1.

Figure 12B:
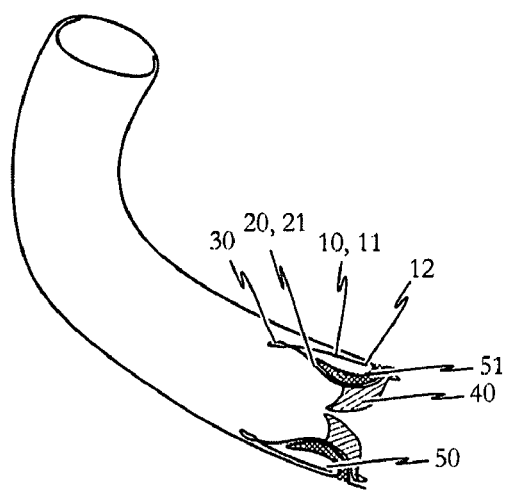
FIG. 12b is a schematic view of the medical device proposed by the invention in the implanted state.

When the medical device is in the implanted state illustrated in FIG. 12*b*, the heart valve prosthesis 40 is opened out at the proximal retaining region 3 of the endoprosthesis 1 whilst the old (insufficient) heart valve 51 is pressed against the vessel wall due to the self-expanding property of the endoprosthesis 1. The distal retaining region of the endoprosthesis 1 affords additional mechanical support for the system and reliable anchoring.

As may specifically be seen from FIG. 12*b*, when the endoprosthesis 1 is in the expanded state, the respective positioning arms 21 of the positioning arches 20 locate in the pockets of the diseased heart valve and thus guarantee secure and error-free positioning of the medical device. The pocket flaps of the diseased heart valve are clamped between the positioning arches 10 and the retaining arches 20 due to the expansion of the endoprosthesis 1, which further assists in achieving optimum positioning and a stable anchoring of the heart valve prosthesis 40 disposed at the proximal retaining region 3 of the endoprosthesis 1. Optimum lateral sealing of the implanted valve prosthesis 40 is guaranteed at the same time.

The system is afforded additional mechanical support and reliable anchoring can also be achieved by providing barbs 17 on the fixing eyes 30 disposed at the distal retaining region 2 of the endoprosthesis 1 and/or by appropriate anchoring supports 25. When the endoprosthesis 1 is in the expanded state, the anchoring supports 25 stand proud of the co-operating arm 21 of the retaining arches 20, and their tips point in the direction of the distal end 2 of the endoprosthesis 1.

In principle, the special design of the endoprosthesis 1 offers the possibility of gripping the endoprosthesis 1 subsequently by means of the fixing eyes 30 and collapsing the medical device by the longitudinal extension of the endoprosthesis 1 so that the medical device can be removed from the patient's body again by means of a catheter tube.

Due to the modular integration of retaining elements (fixing eyes) on the self-expandable endoprosthesis 1, it can also be explanted again by means of a special catheter once it has been implanted. To this end, the distal retaining region 2 of the endoprosthesis 1 is pulled into a catheter by several retaining points using guide wires. This being the case, in the reverse of the implantation operation, the endoprosthesis 1 is pulled from its expanded state into the collapsed state and released from the anchoring in the pockets of the actual heart valve.

In summary, it remains to be said that the solution proposed by the invention is based on a metal endoprosthesis 1 with a heart valve prosthesis which can be stitched to it or is stitched to it, designed for use in treating diseases of the heart valve which make replacement of the old heart valve necessary. The heart valve stent 1 (endoprosthesis) may be introduced in the inverted position and thus positioned orthotopically in vivo percutaneously and assume the function of the insufficient or defective native heart valve. The radial forces created due to the self-expanding property of the endoprosthesis 1 guarantee reliable anchoring in the region of the aorta.

Specifically, a medical instrument comprising an endoprosthesis 1 for positioning and securing a heart valve prosthesis in the aorta of the patient is described, and a specially developed endoprosthesis 1 made from a base of Nitinol is provided as a means of accommodating a heart valve prosthesis for implantation in the aorta. The ready-to-use medical device proposed by the invention consists of the components comprising the self-expandable Nitinol stent 1 with the valve-supporting segment 20, valve and system for introducing it to the desired site in the body.

In terms of design, the endoprosthesis 1 has three positioning arches for positioning and fixing the medical device in the vessel of the patient and retaining webs for accommodating/attaching the heart valve prosthesis by means of a thread, for example. From a functional point of view, the endoprosthesis 1 exerts high radial forces in its second mode to ensure that the medical device is anchored in the aorta. Eyes 30 are preferably provided on the distal retaining region of the endoprosthesis 1 or medical device, which can be releasably engaged with corresponding components of an introduction catheter system.

The material used to trigger the shape memory effect of the endoprosthesis has a switching temperature between 20° C. and 36° C. and is preferably 22° C. In the cooled state, therefore, the medical device can be introduced into the patient's body by means of a 21 F introduction system.

As regards the exact dimensions of the endoprosthesis 1, it is designed to accommodate heart valve prostheses with a valve diameter of 21 mm to 25 mm, in which case the distal retaining region 2 of the endoprosthesis 1 in particular has a diameter that is approximately 10% to 15% bigger than this in order to ensure that the medical device is reliably anchored.

The medical device proposed by the invention has an endoprosthesis which is readily visible by X-ray, which can be achieved by applying markers at the proximal and/or distal region of the endoprosthesis if necessary.

The materials used for the endoprosthesis 1 are materials that have been tried and tested for implantation purposes, for example Nitinol and Tantal. As regards the dimensions of the endoprosthesis, two different stent sizes are currently preferred, which are set out in the table below together with the diameter of the proximal retaining region and the distal retaining region.

| Stent size | Diameter of the proximal retaining region | Diameter of the distal retaining region |
| --- | --- | --- |
| Stent No. 1 | 21 to 25 mm | 32 to 34 mm |
| Stent No. 2 | 26 to 31 mm | 35 to 38 mm |

By applying an appropriate finishing treatment, in particular tempering, other dimensions of the stent can be achieved—starting from the two currently preferred stent sizes.

The invention is not restricted to the features described in connection with the preferred embodiments illustrated in the drawings. All combinations of the features described in the specification would be conceivable.

The invention claimed is:

1. Medical device for treating a native heart valve having a plurality of native valve leaflets, comprising:
an endoprosthesis having a plurality of positioning arches configured to be respectively positioned within a plurality of pockets of the native heart valve on a first side of the plurality of native valve leaflets and a plurality of retaining arches configured to be positioned on a second side of the plurality of native valve leaflets such that the plurality of native valve leaflets are positioned radially inward of at least a portion of the plurality of positioning arches and positioned radially outward of at least a portion of the plurality of retaining arches when the medical device is implanted, wherein each retaining arch is associated with a corresponding positioning arch and has a distal end portion axially aligned, along a longitudinal direction of the endoprosthesis, with and joined to a distal end portion of the corresponding positioning arch; and
a prosthetic valve attached to the plurality of retaining arches such that at least part of the prosthetic valve extends from the plurality of retaining arches transversely across an interior of the endoprosthesis.

2. Medical device as claimed in claim 1, in which each positioning arch includes a substantially U-shaped or V-shaped structure.

3. Medical device as claimed in claim 1, in which each retaining arch includes a substantially U-shaped or V-shaped structure.

4. Medical device as claimed in claim 1, in which the distal end portion of the corresponding positioning arch is joined to the distal end portion of the corresponding retaining arch by a connecting web extending substantially in the longitudinal direction of the endoprosthesis.

5. Medical device as claimed in claim 1, in which the endoprosthesis further includes at least one eye-shaped element at the distal end of the endoprosthesis, the at least one eye-shaped element configured to be engaged with an introduction catheter system.

6. Medical device as claimed in claim 5, in which the at least one eye-shaped element is fixedly connected to and disposed substantially between two adjacent positioning arches.

7. Medical device as claimed in claim 6, in which the at least one eye-shaped element is disposed substantially between two adjacent retaining arches and fixedly connected to respective arms of the two adjacent retaining arches via a connecting web, the connecting web extending substantially in the longitudinal direction of the endoprosthesis.

8. Medical device as claimed in claim 6, in which the two adjacent positioning arches are indirectly joined by a connecting web extending substantially in the longitudinal direction of the endoprosthesis to the at least one eye-shaped element.

9. Medical device as claimed in claim 6, in which the at least one eye-shaped element includes at least one barb having a tip pointing in the direction of the proximal end of the endoprosthesis.

10. Medical device as claimed in claim 1, in which each of the plurality of retaining arches includes a pair of arms, the device further including a plurality of anchoring arches disposed circumferentially between and directly connected to respective arms of two adjacent retaining arches.

11. Medical device as claimed in claim 10, in which each of the anchoring arches includes a substantially U-shaped or V-shaped structure, which is closed at a distal end and including arms extending therefrom toward a proximal end and being joined to respective arms of two adjacent retaining arches.

12. Medical device as claimed in claim 1, in which each of the respective retaining arches includes a pair of arms having slots provided therein.

13. Medical device as claimed in claim 12, in which each of the respective retaining arches includes a reinforcing portion which interrupts a respective slot.

14. Medical device as claimed in claim 1, in which the endoprosthesis includes a first collapsed mode when the medical device is being introduced into the patient's body and a second expanded mode when the medical device is in the implanted state.

15. Medical device as claimed in claim 14, in which the endoprosthesis has a concave shape tapering in the direction of the proximal end of the endoprosthesis when the endoprosthesis is in the second mode.

16. Medical device as claimed in claim 15, in which the distal end of the endoprosthesis has a diameter that is approximately 10% to 25% bigger than the diameter of the proximal end of the endoprosthesis when the endoprosthesis is in the second mode.

17. Medical device as claimed in claim 15, in which the proximal end of the endoprosthesis has a diameter of between approximately 22 mm and approximately 33 mm in the second mode.

18. Medical device as claimed in claim 15, in which the proximal end of the endoprosthesis has a diameter of between approximately 25 mm and approximately 31 mm.

19. Medical device as claimed in claim 14, in which the endoprosthesis has an external diameter of approximately 5.0 mm and a length between approximately 33.0 mm and approximately 40.0 mm when in the first mode.

20. Medical device as claimed in claim 14, in which the endoprosthesis has a length between approximately 34.0 mm and approximately 39.0 mm when in the first mode.

21. Medical device as claimed in claim 1, in which the endoprosthesis is made from a shape memory material so that the endoprosthesis can be expanded from a collapsed shape to an expanded shape under the effect of an external stimulus.

22. Medical device as claimed in claim 21, in which the external stimulus is a settable switching temperature.

23. Medical device as claimed in claim 22, in which the switching temperature is approximately 22° C.

24. Medical device as claimed in claim 1, in which the plurality of positioning arches are expandable from a first collapsed mode to a second expanded mode independently from the plurality of retaining arches.

25. Medical device as claimed in claim 1, in which the endoprosthesis is integrally cut from a metal tube.

26. Medical device as claimed in claim 1, in which the plurality of positioning arches are configured to expand from a collapsed mode to an expanded form.

27. Medical device as claimed in claim 1, in which the endoprosthesis is configured to at least partially clamp the native valve leaflets when implanted.

28. Medical device as claimed in claim 1, wherein the prosthetic valve is sutured to the plurality of retaining arches.

29. Medical device as claimed in claim 1, wherein radially outer most portions of the endoprosthesis are defined by the plurality of positioning arches and the plurality of retaining arches.

30. Medical device as claimed in claim 1, wherein an apex of each of the plurality of positioning arches is substantially axially aligned along the longitudinal direction of the endoprosthesis with an apex of a corresponding retaining arch.

31. A medical device for treating a native heart valve having a plurality of native valve leaflets, comprising:
an endoprosthesis having a plurality of positioning arches configured to be respectively positioned within a plurality of pockets of the native heart valve on a radially outward side of the plurality of native valve leaflets;
the endoprosthesis having a plurality of retaining arches configured to be positioned on a radial inward side of the plurality of native valve leaflets;
the endoprosthesis having a plurality of connecting webs joining the plurality of positioning arches directly to the plurality of retaining arches; and
a prosthetic valve attached to the plurality of retaining arches and extending from the plurality of retaining arches transversely across an interior of the endoprosthesis;
wherein each positioning arch includes a pair of arms connected to one another forming a distal open end and a proximal closed end, each arm connected at a distal end thereof to a respective connecting web, such that each positioning arch defines a single apex between two adjacent connecting webs;
wherein each retaining arch includes a pair of arms connected to one another forming a distal open end and a proximal closed end, each arm connected at a distal end thereof to a respective connecting web, such that each retaining arch defines a single apex between two adjacent connecting webs.

32. The medical device as claimed in claim 31, in which each positioning arch includes a substantially U-shaped or V-shaped structure.

33. The medical device as claimed in claim 31, in which each retaining arch includes a substantially U-shaped or V-shaped structure.

34. The medical device as claimed in claim 31, further including slots formed in each of the respective arms of the plurality of retaining arches.

35. The medical device as claimed in claim 34, further including a reinforcing portion formed in each of the respective arms of the plurality of retaining arches that interrupts a respective slot.

36. The medical device as claimed in claim 31, in which the endoprosthesis includes a first collapsed mode when the medical device is being introduced into the patient's body and a second expanded mode when the medical device is in the implanted state.

37. The medical device as claimed in claim 36, in which the endoprosthesis has a concave shape tapering in the direction of the proximal end of the endoprosthesis when the endoprosthesis is in the second mode.

38. The medical device as claimed in claim 31, in which the plurality of positioning arches are configured to expand from a collapsed mode to an expanded mode independently from the plurality of retaining arches.

39. The medical device as claimed in claim 31, in which the endoprosthesis is configured to at least partially clamp the native valve leaflets radially between the positioning arches and retaining arches.

40. The medical device as claimed in claim 31, wherein the prosthetic valve is sutured to the plurality of retaining arches.

41. The medical device as claimed in claim 31, wherein the radially outer most portions of the endoprosthesis are defined by the plurality of positioning arches and the plurality of retaining arches.

42. The medical device as claimed in claim 31, wherein an apex of each of the plurality of positioning arches is substantially axially aligned along the longitudinal direction of the endoprosthesis with an apex of a corresponding retaining arch.

43. A medical device for treating a native heart valve, comprising an endoprosthesis having a plurality of positioning arches configured to be respectively positioned within a plurality of pockets of a native heart valve and a plurality of retaining arches;
wherein each positioning arch includes a pair of arms defining a distal open end and a proximal closed end;
wherein each retaining arch includes a pair of arms defining a distal open end and a proximal closed end;
wherein the endoprosthesis includes a first collapsed mode when the medical device is being introduced into a patient's body and a second expanded mode when the medical device is implanted;
wherein the proximal closed end of each of the plurality of positioning arches is positioned, along an axial direction of the endoprosthesis, closer to the proximal closed end of a respective retaining arch than the distal open end of the respective retaining arch when the endoprosthesis is implanted;
wherein each of the plurality of positioning arches is axially aligned along the longitudinal direction of the endoprosthesis with a corresponding retaining arch; and
wherein a heart valve prosthesis is directly attached to the plurality of retaining arches.

44. The medical device as claimed in claim 43, in which each positioning arch includes a substantially U-shaped or V-shaped structure.

45. The medical device as claimed in claim 43, in which each retaining arch includes a substantially U-shaped or V-shaped structure.

46. The medical device as claimed in claim 43, further including slots formed in each of the respective arms of the plurality of retaining arches.

47. The medical device as claimed in claim 46, further including a reinforcing portion formed in each of the respective arms of the plurality of retaining arches that interrupts a respective slot.

48. The medical device as claimed in claim 43, in which the endoprosthesis has a concave shape tapering in the direction of the proximal end of the endoprosthesis when the endoprosthesis is in the second mode.

49. The medical device as claimed in claim 43, in which the plurality of positioning arches are configured to expand from a collapsed mode to an expanded form independently from the plurality of retaining arches.

50. The medical device as claimed in claim 43, in which the endoprosthesis is configured to at least partially clamp the native valve leaflets radially between the positioning arches and retaining arches.

51. The medical device as claimed in claim 43, wherein the heart valve prosthesis is sutured to the plurality of retaining arches.

52. The medical device as claimed in claim 43, wherein the heart valve prosthesis extends from the plurality of retaining arches transversely across an interior of the endoprosthesis.

53. The medical device as claimed in claim 43, wherein radially outer most portions of the endoprosthesis are defined by the plurality of positioning arches and the plurality of retaining arches.

\* \* \* \* \*

UNITED STATES PATENT AND TRADEMARK OFFICE
CERTIFICATE OF CORRECTION

| | | |
|---|---|---|
| PATENT NO. | : 7,896,915 B2 | |
| APPLICATION NO. | : 11/785072 | |
| DATED | : March 1, 2011 | |
| INVENTOR(S) | : Volker Guyenot et al. | |

It is certified that error appears in the above-identified patent and that said Letters Patent is hereby corrected as shown below:

In the Specification, col. 3, line 36, "sate" should read --state--.

Signed and Sealed this
Twenty-fourth Day of May, 2011

David J. Kappos
*Director of the United States Patent and Trademark Office*